United States Patent
McCarthy

(10) Patent No.: US 9,662,228 B2
(45) Date of Patent: May 30, 2017

(54) METHOD FOR ALIGNING AN ACETABULAR CUP

(71) Applicant: Howmedica Osteonics Corp., Mahwah, NJ (US)

(72) Inventor: Thomas Francis McCarthy, Neshanic Station, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 461 days.

(21) Appl. No.: 14/459,642

(22) Filed: Aug. 14, 2014

(65) Prior Publication Data

US 2015/0088146 A1 Mar. 26, 2015

Related U.S. Application Data

(63) Continuation-in-part of application No. 14/038,033, filed on Sep. 26, 2013, now Pat. No. 9,248,002.

(51) Int. Cl.
| | |
|---|---|
| *A61F 2/46* | (2006.01) |
| *A61B 34/20* | (2016.01) |
| *A61B 34/10* | (2016.01) |

(52) U.S. Cl.
CPC ............ *A61F 2/4609* (2013.01); *A61B 34/10* (2016.02); *A61B 34/20* (2016.02); *A61B 2034/101* (2016.02)

(58) Field of Classification Search
CPC ... A61B 2034/101; A61B 34/10; A61B 34/20; A61F 2/4609
See application file for complete search history.

(56) References Cited

U.S. PATENT DOCUMENTS

| | | |
|---|---|---|
| 5,037,424 A | 8/1991 | Aboczsky |
| 5,571,111 A | 11/1996 | Aboczky |
| 6,395,005 B1 | 5/2002 | Lovell |
| 6,405,072 B1 | 6/2002 | Cosman |
| 6,428,547 B1 | 8/2002 | Vilsmeier et al. |

(Continued)

OTHER PUBLICATIONS

Babisch et. al. The Rationale for Tilt-Adjusted Acetabular Cup Navigation. The Journal of Bone and Joint Surgery (Impact Factor: 3.23). Feb. 2008; 90(2):357-65.

(Continued)

*Primary Examiner* — Samuel Hanna
(74) *Attorney, Agent, or Firm* — Lerner, David, Littenberg, Krumholz & Mentlik, LLP

(57) ABSTRACT

A method is used for aligning an acetabular cup insertion instrument by taking a single lateral view pre-operative digital x-ray of a standing patient's pelvis. The natural pelvic tilt angle is determined by locating an anterior pelvic plane (APP) which is defined by first, second and third points on the anterior of the pelvis and determining the angle between the APP and a coronal plane perpendicular to the surface on which the patient is standing. The patient is then placed on a surface of an operating room table in a supine position. A position tracking device is placed on the patient's pelvis to track movement. Thereafter an operating room navigation or orientation system is used to relocate the APP defined by the first, second and third points. A cup insertion instrument having a position tracking device thereon is oriented using the navigation or orientation system.

8 Claims, 49 Drawing Sheets

(56) References Cited

U.S. PATENT DOCUMENTS

| | | |
|---|---|---|
| 6,701,174 B1 | 3/2004 | Krause et al. |
| 6,990,368 B2 | 1/2006 | Simon et al. |
| 7,039,225 B2 | 5/2006 | Tanaka et al. |
| 7,194,295 B2 | 3/2007 | Vilsmeier |
| 7,837,621 B2 | 11/2010 | Krause et al. |
| 7,877,131 B2 | 1/2011 | Jansen et al. |
| 8,170,641 B2 | 5/2012 | Belcher |
| 8,206,405 B2 | 6/2012 | Beverland et al. |
| 8,394,036 B2 | 3/2013 | Kozak |
| 8,449,551 B2 | 5/2013 | Amiot et al. |
| 2002/0077540 A1 | 6/2002 | Kienzle |
| 2004/0087852 A1 | 5/2004 | Chen et al. |
| 2005/0065617 A1 | 3/2005 | Moctezuma de la Barrera et al. |
| 2009/0105714 A1* | 4/2009 | Kozak .................. A61F 2/4657 606/102 |
| 2011/0313424 A1 | 12/2011 | Bono et al. |
| 2012/0172884 A1 | 7/2012 | Zheng et al. |

OTHER PUBLICATIONS

Berthonnaud et al., "Accessing 3D Location of Standing Pelvis: Relative Position of Sacral Plateau and Acetabular Cavities versus Pelvis," Radiology Research and Practice, vol. 2012, 10 pages, 2012.

Callanan et al., The John Charnley Award: risk factors for cup malpositioning: quality improvement through a joint registry at a tertiary hospital, Clin Orthop Relat Res., 469(2):319-29, Feb. 2011, abstract.

Egglie et al., Value of preoperative planning in total hip arthroplasty, Journal of Bone and Joint Surgery, vol. 80-B, No. 3, May 1998.

Lazennec et al., Pelvis and total hip arthroplasty acetabular component orientations in sitting and standing positions: measurements reproductibility with EOS imaging system versus conventional radiographies, Orthop Traumatol Surg Res., 97(4):373-80, May 12, 2011, abstract.

Miller, EOS Imaging System is an Emerging New Technology, www.bioclinica.com, 1 page, Dec. 5, 2012.

Murray, The definition and measurement of acetabular orientation, J Bone Joint Surg Br., 75(B):228-32, 1993.

\* cited by examiner

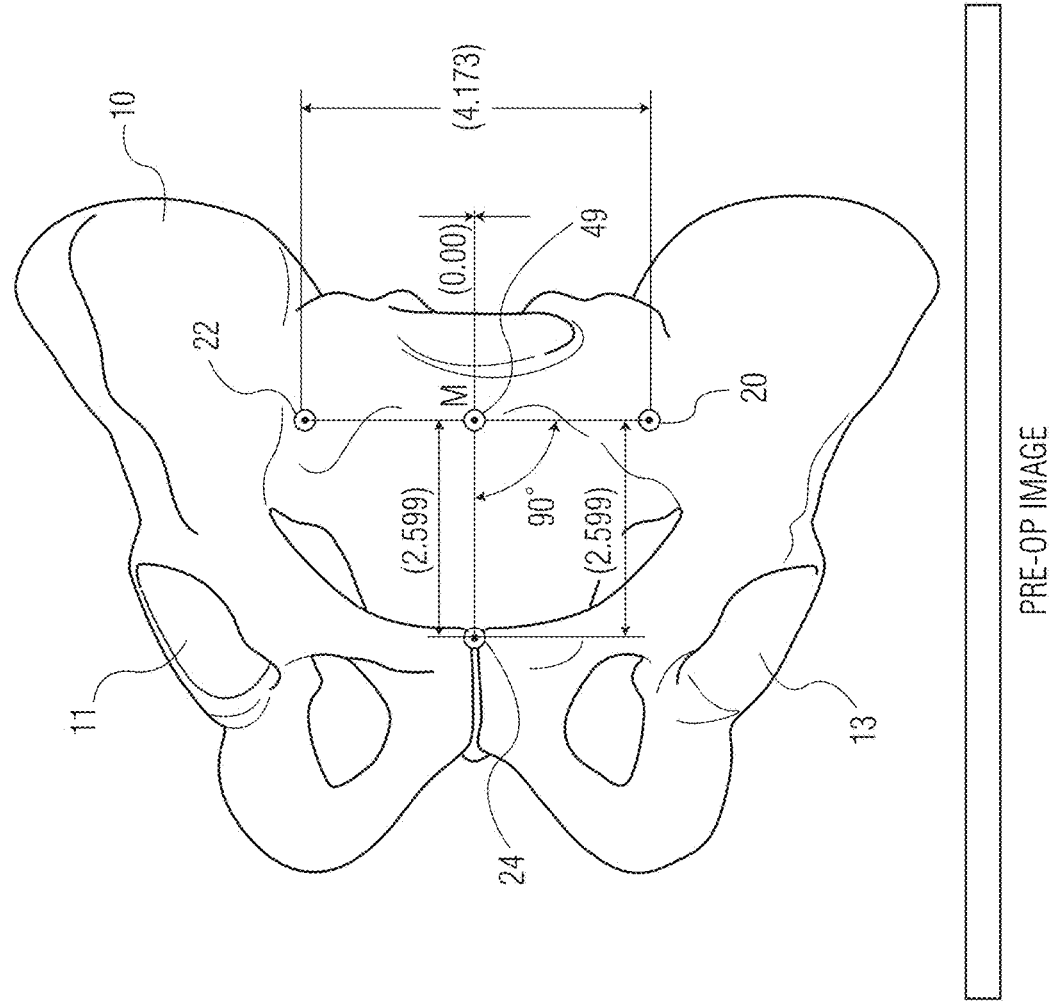

INTRA-OP IMAGE

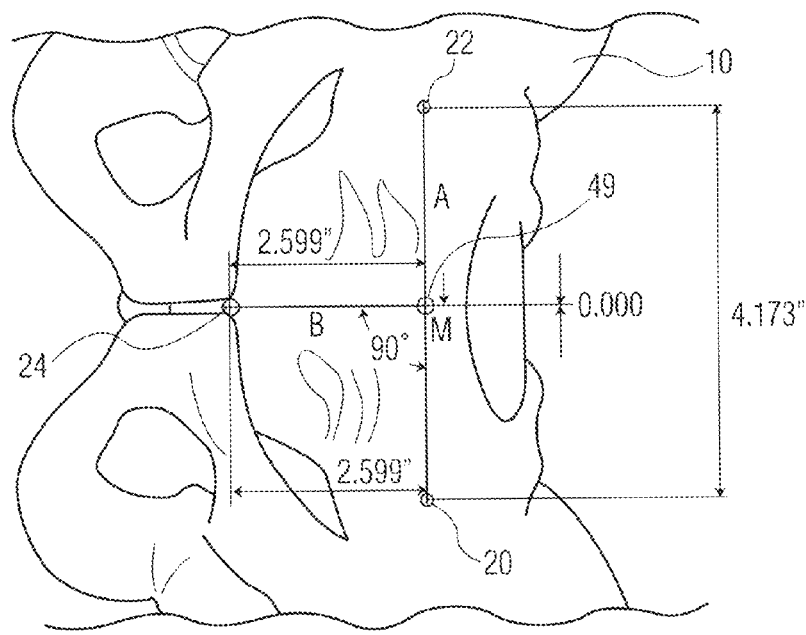
STANDING IMAGE    FIG. 12B
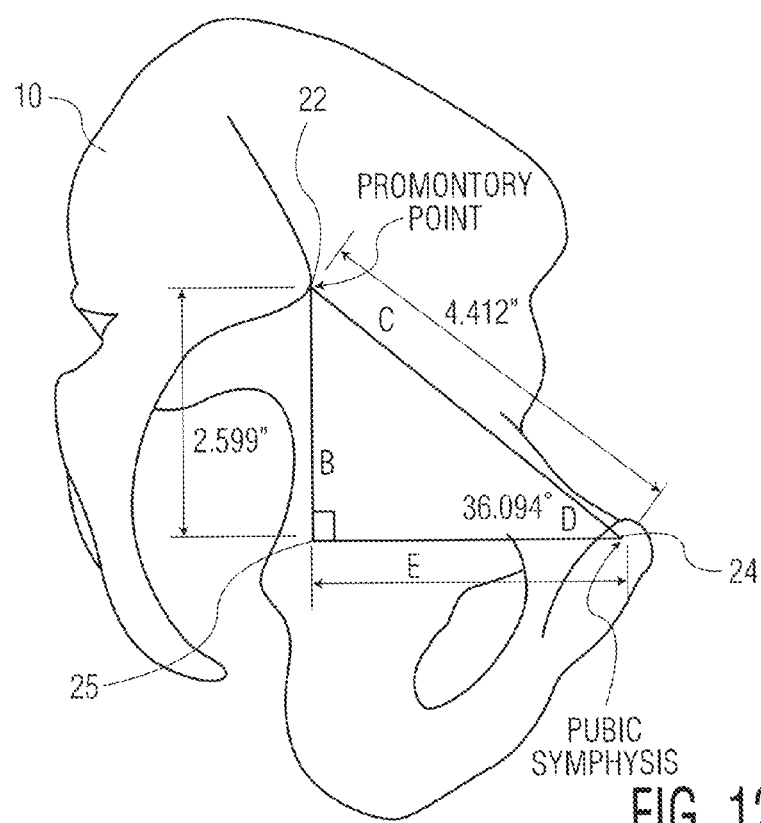
FIG. 12C

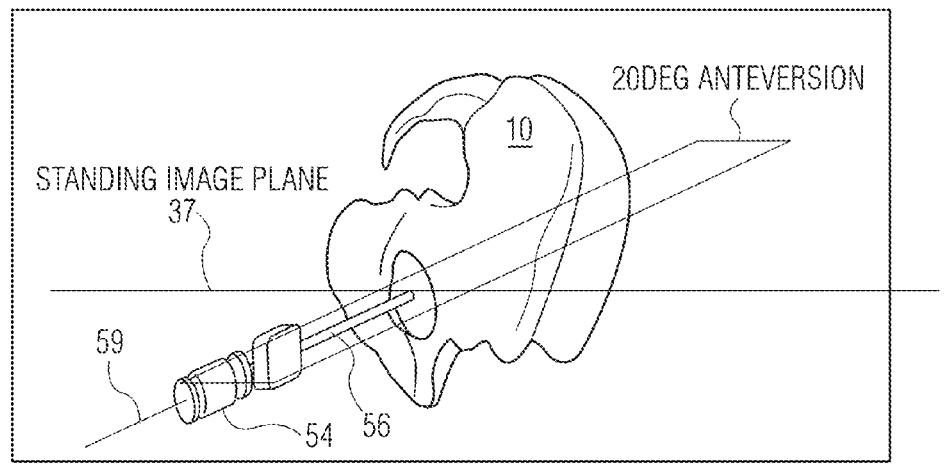
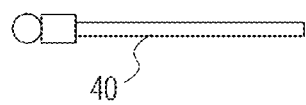
FIG. 13
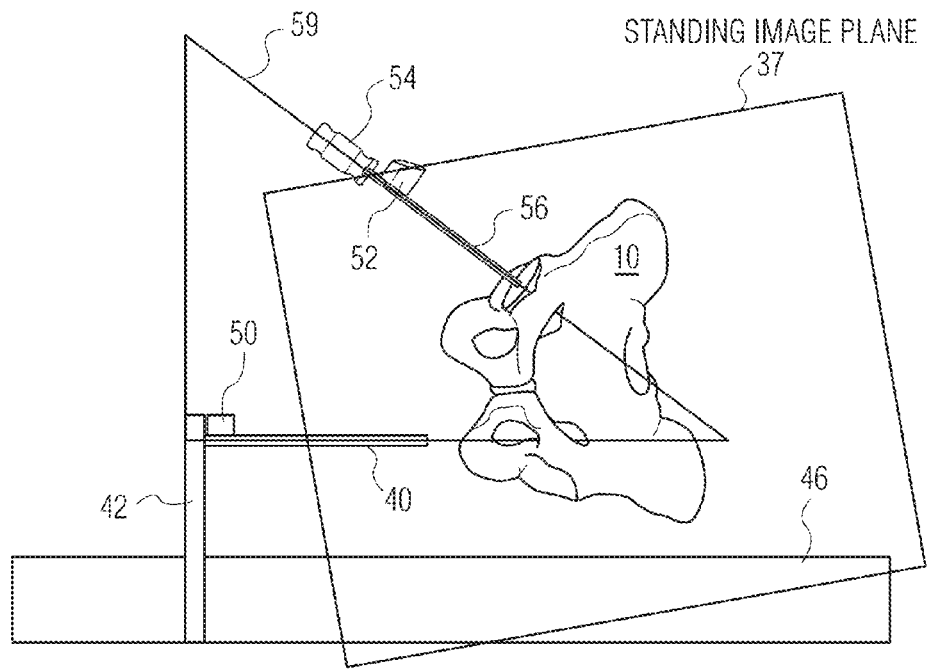
FIG. 13A

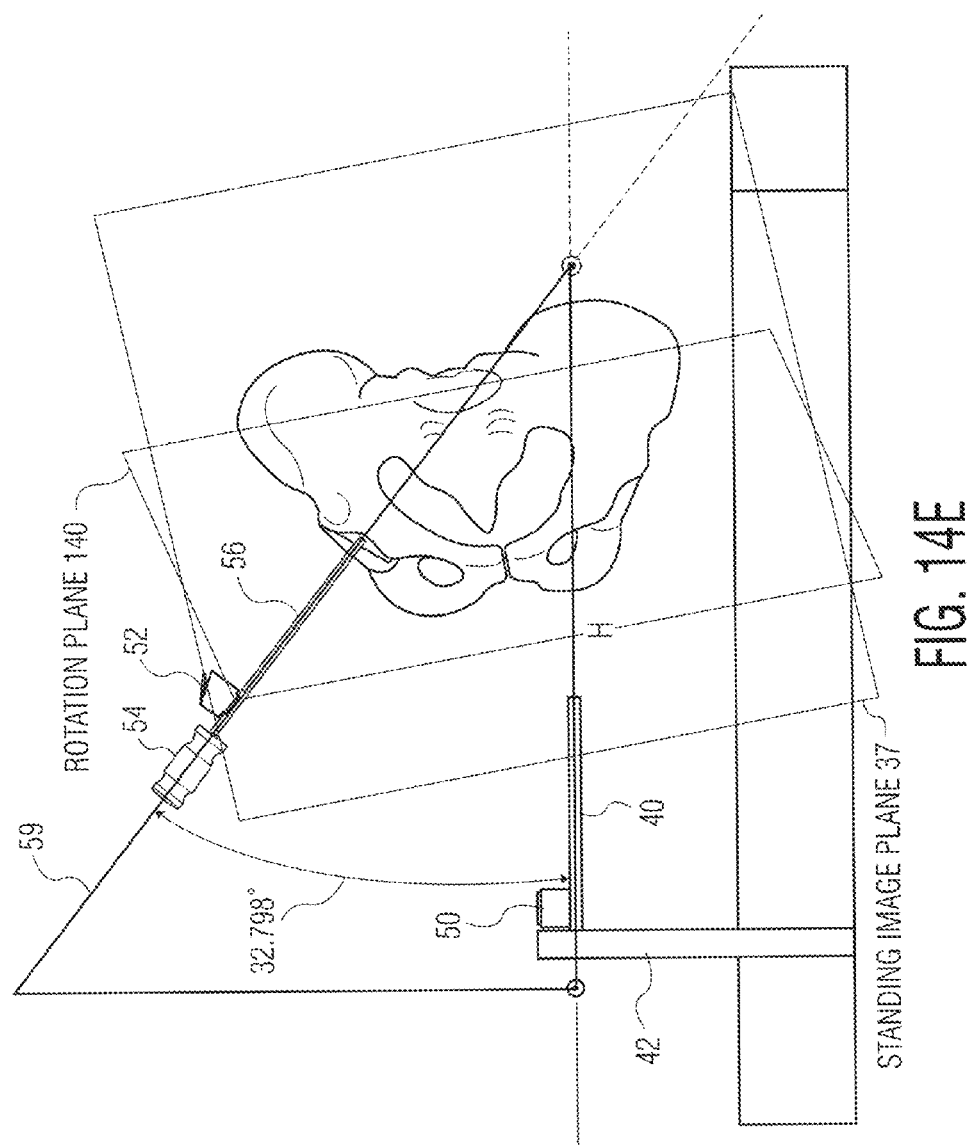

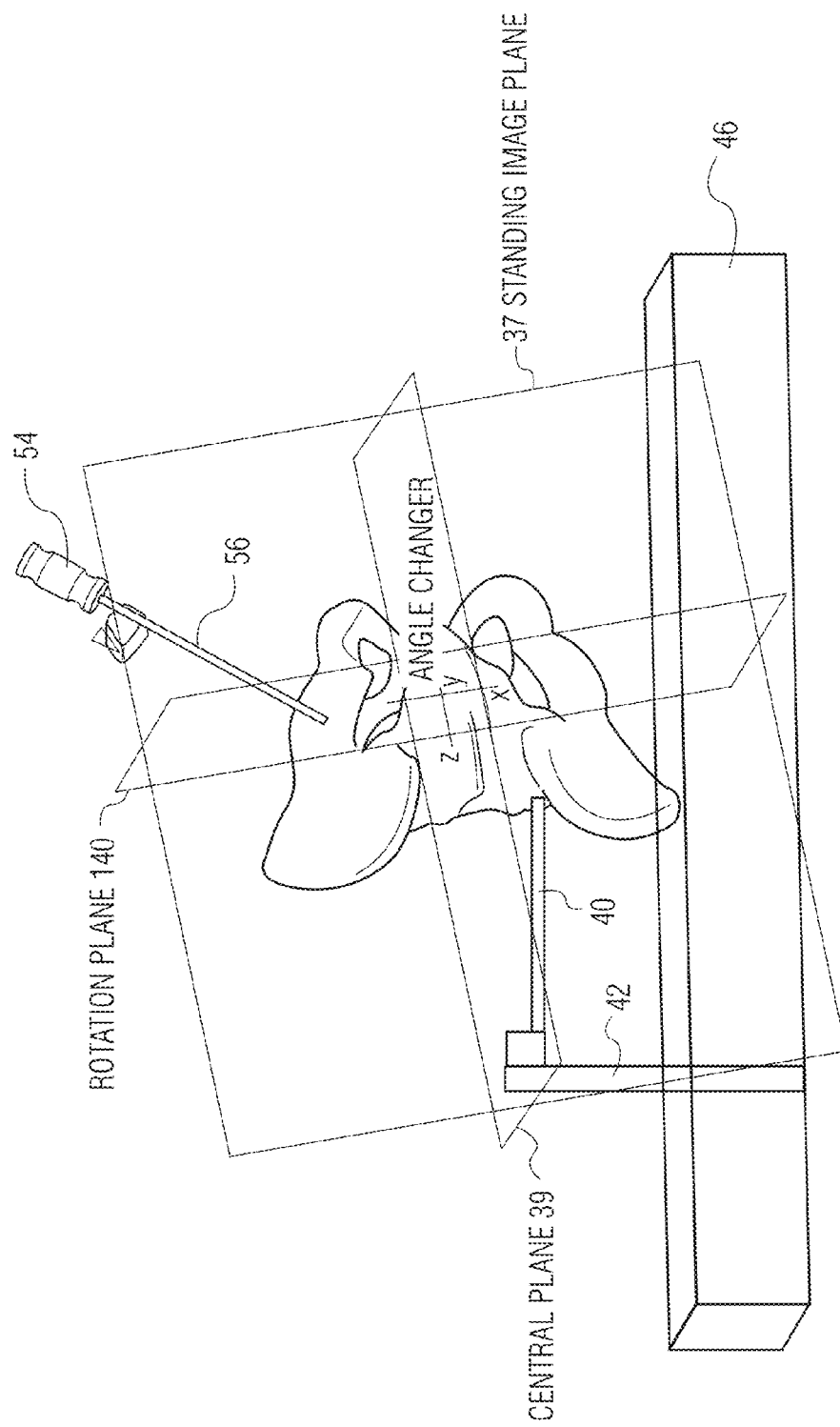

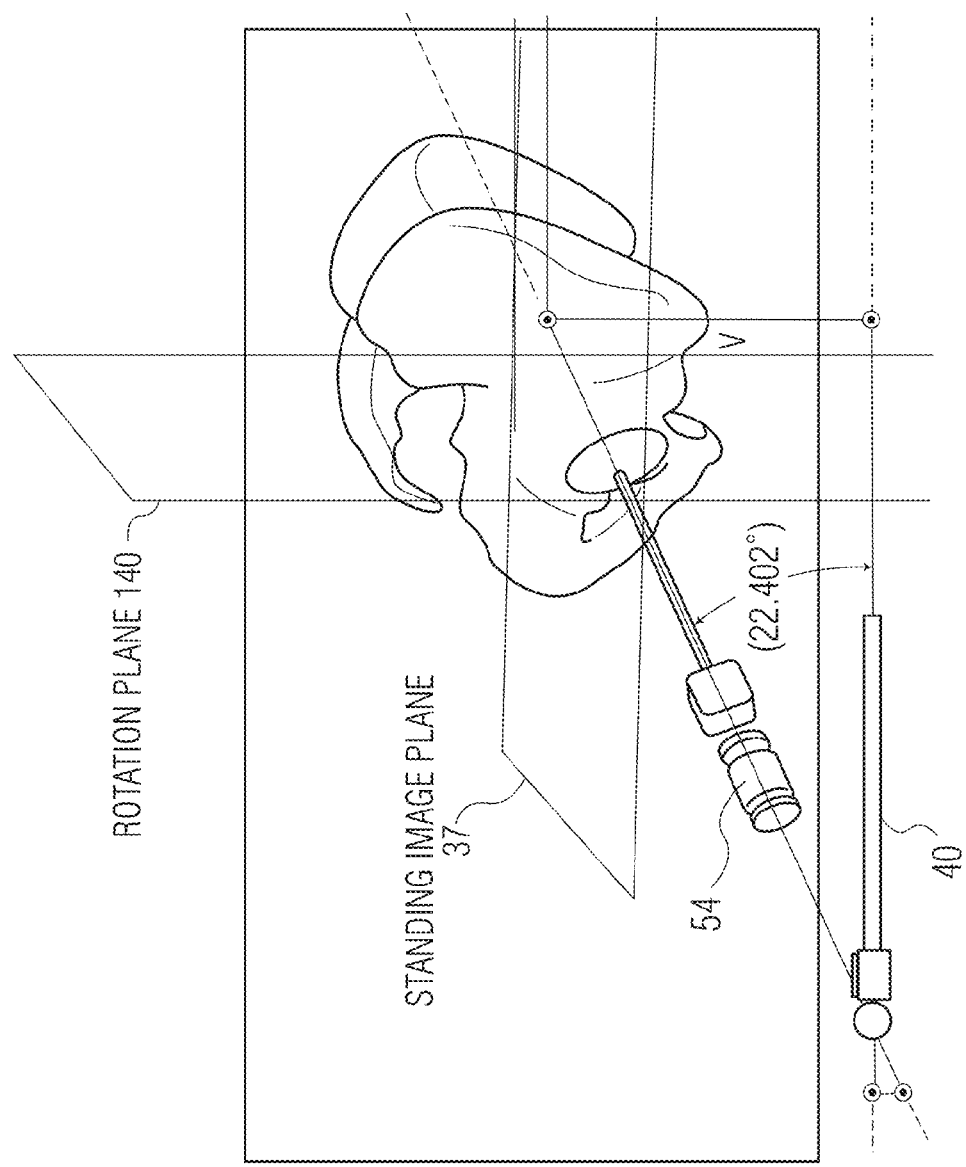

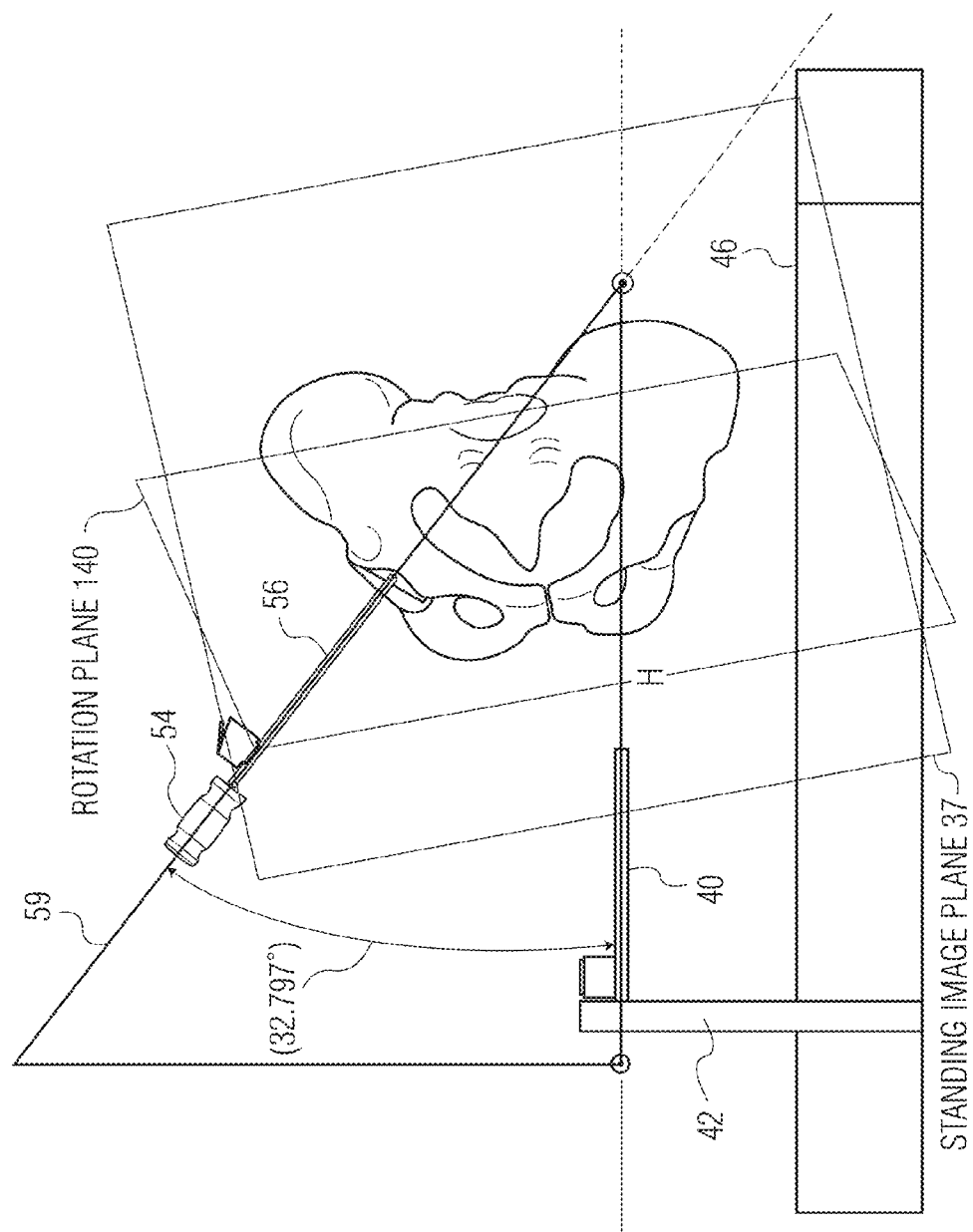

METHOD FOR ALIGNING AN ACETABULAR CUP

CROSS-REFERENCE TO RELATED APPLICATIONS

This application is a continuation-in-part of U.S. patent application Ser. No. 14/038,033, filed Sep. 26, 2013, now U.S. Pat. No. 9,248,002 B2; the disclosure of which is incorporated herein by reference.

BACKGROUND OF THE INVENTION

Hip surgery requires the implantation of a femoral stem and an acetabular cup. The femoral stem has a spherical head that attaches to the neck of the stem and is free to articulate within a bearing insert that is fitted into the shell of an acetabular cup. Should the stem and cup not be positioned/aligned accurately, the neck of the stem may impinge on the lip of the insert resulting in a levering action that could allow the femoral head to cam out of the insert resulting in a permanent dislocation of the head. The impingement can also lead to excessive component wear and possibly failure.

In addition, a malpositioned cup can result in excessive liner wear even without impingement. A shell with a high abduction (inclination) angle can have joint forces concentrated near the cup liner rim, thereby increasing the wear rate due to concentrated forces.

Reducing or eliminating the chance for neck/insert impingement and high inclination angles is critical to eliminating dislocation and wear, which can ultimately result in a revision surgery to correct compound alignment (abduction and anteversion).

A recent study by H. Malchau et al., Clin. Orthop. Relat. Res. (2011) 469; 319-329 reviewed the implanted acetabular cup position post implantation in relation to the pelvic anatomy. The study of 1823 patients revealed that the cup position varied widely in reference to their described target zone.

One main reason for such variation is that the exact position of the patient's pelvis is not known in relation to the operating room (OR) table. Surgeons must rely on their experience to know how to position the cup, however the cup may not be implanted in the intended orientation. This is especially true with respect to less experienced surgeons.

Alignment of an acetabular cup can be achieved with an alignment guide that attaches to an insertion rod for facilitating the insertion of the acetabular cup into the acetabulum. The alignment guide preferably references the surgical table on which the patient rests. Conventionally, it is assumed that the patient's pelvis is parallel to the table, and that the surgical table is parallel to the floor. Based on such assumptions, the ordinary position (in most patients) for the acetabular cup is 45° of inclination (abduction) and 20° of anteversion. For a discussion of angles of anteversion and also inclination or abduction of the acetabular cup when installed in the acetabulum, see, for example, "The Definition and Measurement of Acetabular Orientation", The Journal of Bone and Joint Surgery, 75-B; pp. 228-32, (1993).

It has been found based on post-operative x-rays, however, that despite the alignment guide being parallel to the floor during insertion, of the acetabular cup, the resultant inclination or anteversion of the acetabulum in relation to the alignment guide is often different than expected and, thus, the acetabular cup has been installed at a less than ideal position. The pelvic position changes in relation to the operating room table which is not recognized during the procedure for example.

Presently most orthopedic companies offer instrumentation to direct reaming for acetabular cups and cup impaction which is an antenna-like device that attaches to either the reamer shaft or the cup impaction tool. Such cup alignment instruments are shown in, for example, U.S. Pat. Nos. 5,037,424, 5,571,111 and 6,395,005. When an x-shaped "antenna" is used a cup impactor that is oriented 45 degrees to the floor and 20 degrees to the long axis of the patient. The 'X' shape on the antenna is set parallel to the floor, and one leg of the 'X' set in line with the long axis of the body. One leg is for a left leg operation, and the other for a right leg operation.

Some of the drawbacks of this type of instrument are that the pelvis usually shifts when the patient is laid on the operating room table. If the pelvis does not shift, and the surgeon wants a 45/20 cup position, then the surgeon could use the instrument as is and get the perfect 45/20 alignment within the bone. However, most times the pelvis does shift in three possible planes: tilt, obliquity, and rotation. The surgeon does not know in which direction or by how much and therefore must use his experience or intuition to apply a correction factor to the direction of cup impaction. The actual cup orientation after impaction is not usually known until after the operation is complete and a post-operative x-ray is taken, and the patient is in recovery, and therefore at a time when changes to cup orientation are not possible without reoperation.

Another drawback is that the current antenna/impactor combination is set at set angles. For example a 45/20 degree abduction/anteversion orientation. If the surgeon determines that orientation of 40° to the floor and 15° to the long axis of the patient's femur is best for the patient, the set angles are of little use, or again the surgeon has to estimate a correct alignment. The orientation of the antenna/impactor combination in practice is set visually. The antenna shaft is set vertically, with the antenna 'X' cross bars parallel to the floor. The 20 degree orientation to the patient long axis is visual as well. Many surgeons do not use the antenna at all.

Some major prosthetic hip joint companies offer a navigation option to surgeons. This system uses cameras in the operating room and optical trackers on instrumentation. From a clinical perspective, the major drawbacks for navigation are that the technique involves placing invasive pins having the tracker thereon in the patient pelvis and femur. The pins are placed in the pelvis and the femur, through the skin and screwed into the bone. Using pins results in multiple separate wounds and increases the possibility of infection. This technique is also time intensive. Pins must be placed and pointers with trackers on them are used multiple times to register anatomy. This technique has a learning curve. The software and technique require extensive training and practical experience. Some systems require a pre-op CT scan which is costly.

A more recent development is digital imaging which produces an x-ray like image on a digital receiver. Once digitized, the digital image can be used to identify points in order for the system to calculate lengths and angles which could be used by the surgeon to help to identify how the pelvis is oriented to the operating room table. The surgeon can take pre-operative and intra-operative x-rays and pick points on the screen to calculate lengths and angles. This is a relatively new technology with a relatively small amount of users.

The x-rays can be visually observed for comparison. The system can aid the user by allowing the user to plan by designating the desired cup inclination and version angles pre-operatively as well as taking dimensions that will help to designate leg length and femoral stem offset corrections. Taking dimensions that will measure the cup inclination and version angles of the actual implanted cup intra-operatively as well as taking dimensions that show that actual leg length and offset of the trials or implants.

However, they do not aid the user by figuring out how the pelvis has shifted on the table as there is no algorithm to do this. A pelvis may have tilted by 15 degrees, yet the cup angle measurement only measures the cup angle at the plane that the x-ray is taken. If the pelvis has tilted by 15 degrees, then the correct cup placement would not be 45°/20° to the intra-op x-ray image, but should be adjusted to account for the tilt.

These current digital imaging systems do not have an algorithm that tries to compare pre-operative and intra-operative images to calculate how the intra-operative pelvic position changes in orientation to a pre-operative image. Furthermore, the current digital systems don't calculate the cup impaction angles that would account for these changes. Instead the cup needs to be first impacted into the bone prior to taking the image, and reoriented if not in the desired position. Reorienting the shell could compromise the fit and security of the cup to the acetabular bone cavity. Multiple reorientations could possibly compromise the fit to the point that a secure fit is no longer achieved. In this situation, the surgeon may have to remove the shell, ream up to the next size shell, and start over. The removal of further acetabular bone is not ideal as this could compromise the overall strength of the remaining bone, and reduce the amount of bone for any future revisions. Current digital imaging techniques require successive intra-operative images, exposing the patient and the surgical team to higher levels of radiation than with a single image.

BRIEF SUMMARY OF THE INVENTION

The present invention uses a pre-operative lateral x-ray image to determine the pelvic tilt angle that is natural for each patient. In the preferred embodiment, the pre-operative lateral x-ray is taken while the patient is standing. The invention describes using a pre-operative lateral x-ray image in conjunction with an intra-operative orientation technology. The pre-operative pelvic tilt angle is used in conjunction with the orientation technology to determine how the pelvis may have shifted during surgery and allow the surgeon to adjust accordingly and implant the cup at the pre-determined orientation. Below summarizes two embodiments, one preferred embodiment for the patient in the lateral decubitus position (laying on their side), and the other for the patient in the supine position.

In the first embodiment of the present invention, the patient is in the lateral decubitus position for the surgery, uses a combination of digital imaging and orientation technology to improve upon the limitations described above, along with an algorithm that determines the amount of pelvic movement in the three planes (obliquity, tilt, rotation) that is used as input for the orientation technology. The preferred embodiment to calculate pelvic tilt obliquity and rotation inoperatively which no other system does. Most pre-operative x-ray images are taken laying down (supine), and hence placing the pelvis in an unnatural position. A standing x-ray is the gold standard as the amount of pelvic tilt when standing is what is right for that individual. This invention serves to recreate the natural standing x-ray tilt and, if desired, obliquity and rotation amount intra-operatively by adjusting the orientation of reaming and cup impaction, and performing these functions at the pre-op plan angles determined by the user (e.g. at 40° inclination and 15° anteversion).

The invention uses a method for aligning an acetabular cup including: taking a pre-operative preferably standing anterior/posterior view digital x-ray image and a lateral view standing digital x-ray image of the pelvis of a patient. A desired cup abduction and anteversion angle is determined based on two standing x-ray images. At least three points on the digital anterior/posterior digital x-ray image and at least two points on the lateral digital x-ray image are identified. The lengths and angles between each of the points on both the anterior/posterior digital image and the lateral digital image are calculated. A patient is positioned on an operating table in an operating room. The preferred operating table has a reference element thereon. In the preferred embodiment, the operating room has a navigation system (orientation technology) therein, the preferred operating table has a navigation tracker mounted in a known position with respect to the operating table. Alternately, the reference system could reference the floor or other fixed point including the operating room table. At least one pelvic digital x-ray image of the patient positioned on the operating table is taken with the x-rays including the reference element. At least three points are identified on the intra-operative x-ray image. In the preferred embodiment, the points corresponding to the points on the pre-operative x-ray image. The lengths and angles between each of the at least three points on the intra-operative digital images are then calculated. An intra-operative angular deviation of the acetabular cup insertion instrument from the desired abduction and anteversion angle i.e. calculated by comparing the dimensional differences between the points on the pre-operative standing x-ray images and the at least one intra-operative x-ray image. The insertion instrument is then aligned to a calculated angular position, based on the intra-operative deviation, using the navigation camera and a navigation tracker mounted on the insertion instrument.

The at least three points on the anterior/posterior pre-operative and intra-operative images are preferably the right and left promontory points and the pubic symphysis. The at least two points on the intra-operative lateral image are preferably the left or right promontory and the public symphysis. However, other points can be used. Additional points may be selected from the group consisting of acetabular teardrops, the obturator foramen and the base of the left and right ischial rings, the points being identified on the pre-operative and intra-operative images. The angle between a line connecting the ischial ring points and the reference element indicates any obliquely change between the pre-operative, preferably standing pelvic anterior/posterior x-ray image and the at least one intra-operative x-rays. The reference element may be a radiopague or radiolucent bar extending parallel to the operating table surface, the radiolucent bar having two radiopaque markers thereon. Alternately, the radiolucent bar has three radiopaque markers, each marker located at an apex of a triangle. The radiopague bar could be made of metal preferably with a thin cross-section in the direction of the x-ray beam. The bar could be metal or aluminum which is semi-transparent to an x-ray beam. The pre-operative determination of the desired cup abduction and anteversion angles based on the standing x-ray are about 30 to 50 degrees and 10 to 30 degrees respectively. The calculations are performed by a computer using digital image analysis software receiving input from a digital x-ray machine and an operating room navigation tracking system. Pelvic tilt may be calculated by comparing the distance between the promontory points and the pubic symphysis on both the pre-operative standing x-rays and the at least one intra-operative x-ray.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. The sagittal plane, being a plane parallel to the sagittal suture, divides the body into left and right portions. The median plane is in the midline; i.e. it would pass through midline structures such as the navel or spine, and all other sagittal planes are parallel to it. The coronal or frontal plane divides the body into dorsal and ventral (back and front, or posterior and anterior) portions. The transverse plane, also known as an axial plane or cross-section, divides the body into cranial and caudal (head and tail) portions.

The second embodiment of the present invention whereas the patient is in the supine position, uses a combination of a pre-operative lateral x-ray image and orientation technology to improve upon the limitations described above.

The various aspects of the present invention are accomplished by a method for aligning an acetabular cup insertion instrument using only a single digital x-ray. A single lateral view pre-operative digital x-ray of standing patient's pelvis is taken and the natural pelvic tilt angle is determined by locating an anterior pelvic plane (APP) defined by first, second and third points on the anterior of the pelvis. Alternatively, two points could be taken on the lateral x-ray if the left and right ASIS points are aligned. In this case, a single point defines both the left and right ASIS. The other point being the public symphysis. The angle between the APP and a coronal plane perpendicular to the surface on which the patient is standing is then determined. The patient is then placed on a surface of an operating room table in a supine position. A position tracking device is placed on the patient's pelvis to track movement of the pelvis during surgery. Thereafter relocating the APP defined by the first, second and third points is again located. Thereafter the coronal plane is located by using the determined natural pelvic tilt angle and APP plane, an acetabular cup insertion instrument having a position tracking device thereon is oriented at a predetermined abduction angle with respect to the sagittal plane, and anteversion angle with respect to the coronal plane.

The first, second and third points may be the pubic symphysis, the left anterior superior iliac spine and the right anterior superior iliac spine.

A position tracking device may be used to intraoperatively locate the pubic symphysis and the left and right anterior superior iliac spines.

A sagittal plane is defined through a mid-point between the left and right anterior superior iliac spines and perpendicular to the coronal plane.

A cup insertion instrument is then oriented at a predetermined abduction angle with respect to the sagittal plane and a predetermined version angle with respect to the coronal plane.

The predetermined desired cup abduction and anteversion angles are about 30 to 50 degrees and preferably between 10 to 30 degrees respectively.

The orientation of the cup insertion instruments is directed by a computer using digital image analysis software receiving input from the single digital x-ray and the operating room position tracking system. Note that the lateral image pelvic tilt angle can be determined from a standard non-digital x-ray and angle value then used in the calculations.

Further aspects of the invention are achieved by a method for aligning an acetabular cup insertion instrument using only a single digital x-ray. The single x-ray is a single standing lateral view pre-operative digital x-ray of a standing patient's pelvis. The patient's natural pelvic tilt angle may be determined by locating an anterior pelvic plane (APP) defined by points at the pubic symphysis, the left anterior superior iliac spine and the right anterior superior iliac spine. The angle between the APP and a coronal plane is then determined. The patient is then placed on a surface of an operating room table in a supine position. Thereafter, using an operating room navigation system position tracking device the pubic symphysis, the left anterior superior iliac sine and the right anterior superior iliac sine points are located.

The predetermined angles are an abduction angle and an anteversion angle and the predetermined desired cup abduction and anteversion angles are preferably about 30 to 50 degrees and 10 to 30 degrees respectively.

Once the anteversion and abduction angles are known, the orientation of the cup insertion instruments may be directed by a computer using digital image analysis software receiving input from the single digital x-ray and the operating room position tracking system.

DETAILED DESCRIPTION

Figure 1A:
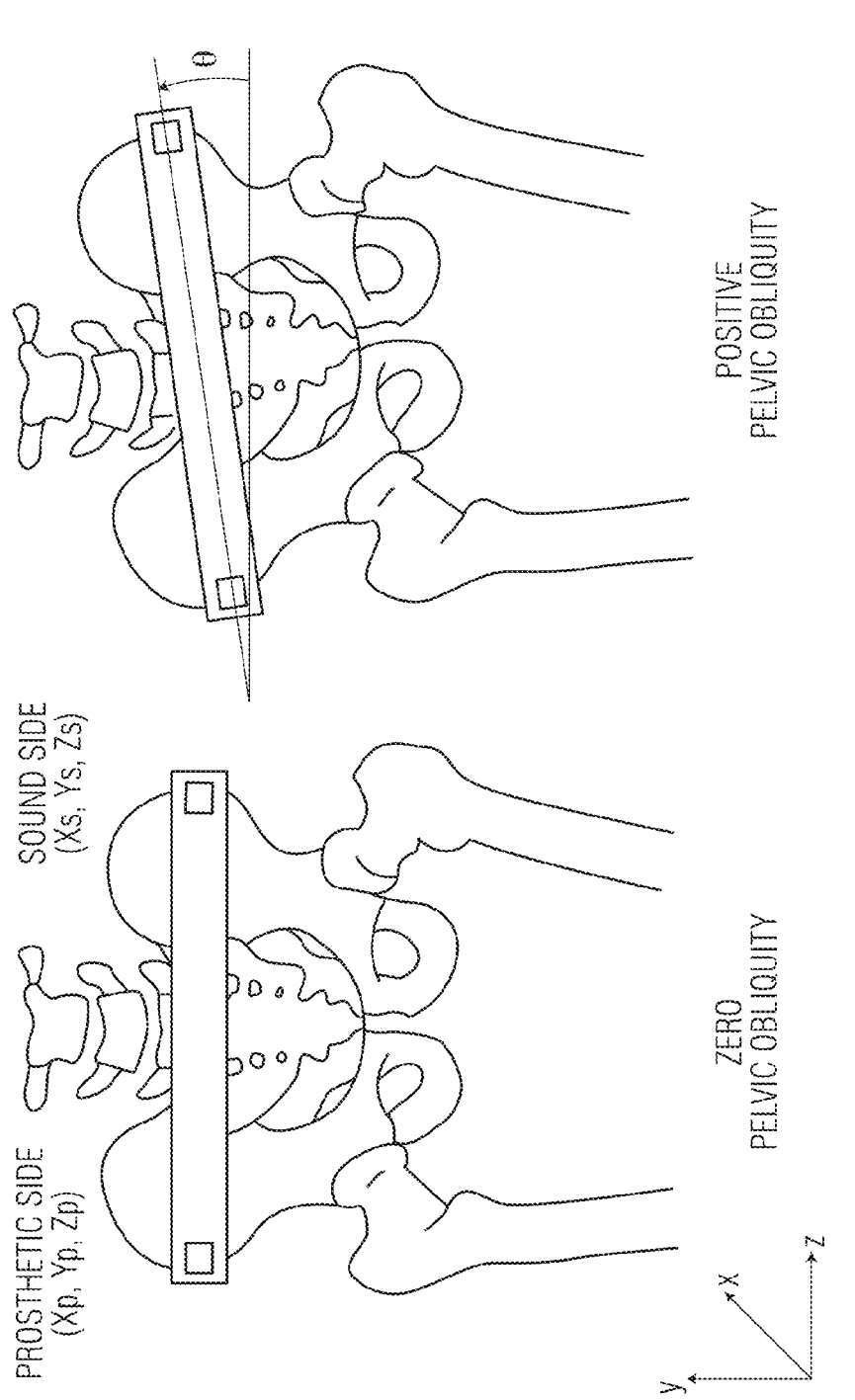
FIGS. 1A to 1C are reference diagrams showing pelvic obliquity, pelvic rotation and pelvic tilt which three axial movements typically occur when moving from a standing position to a prone position.
Figure 1B:
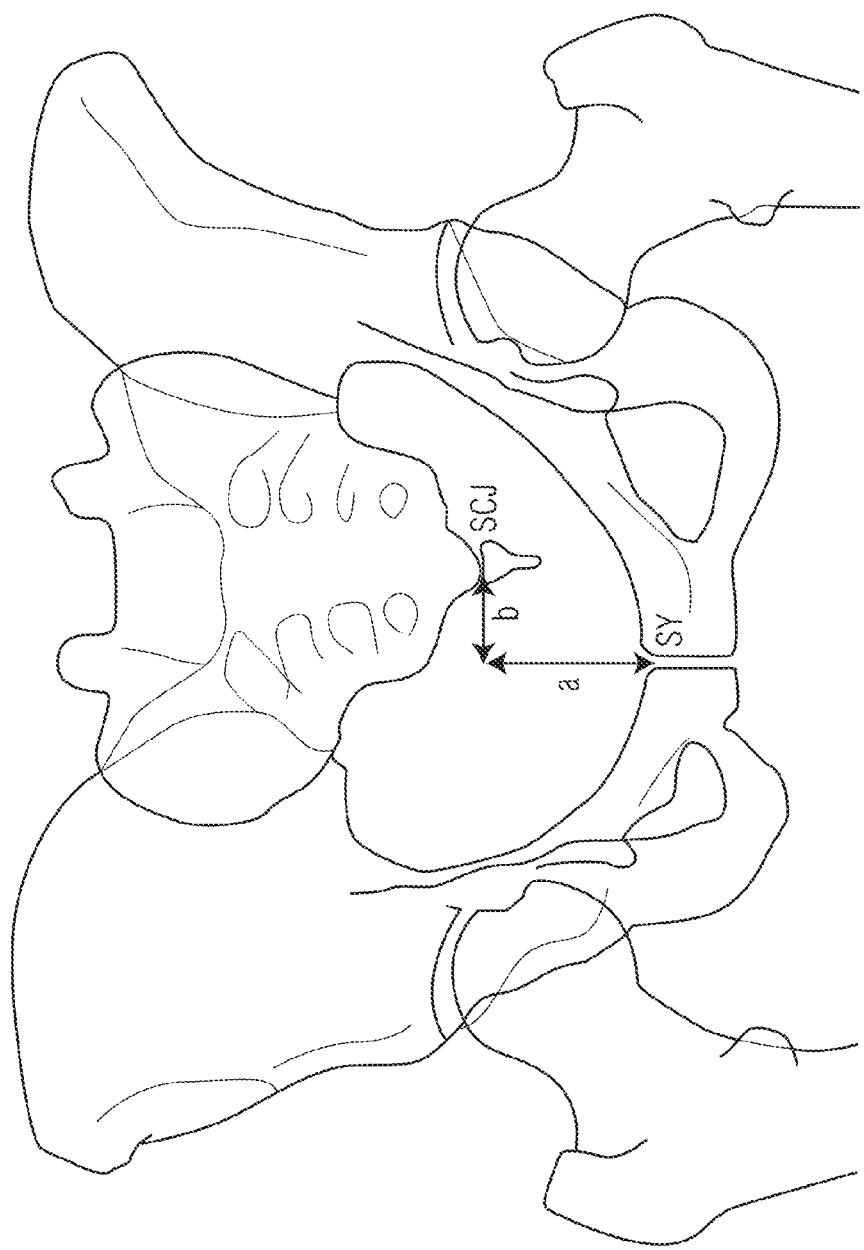
Figure 1C:
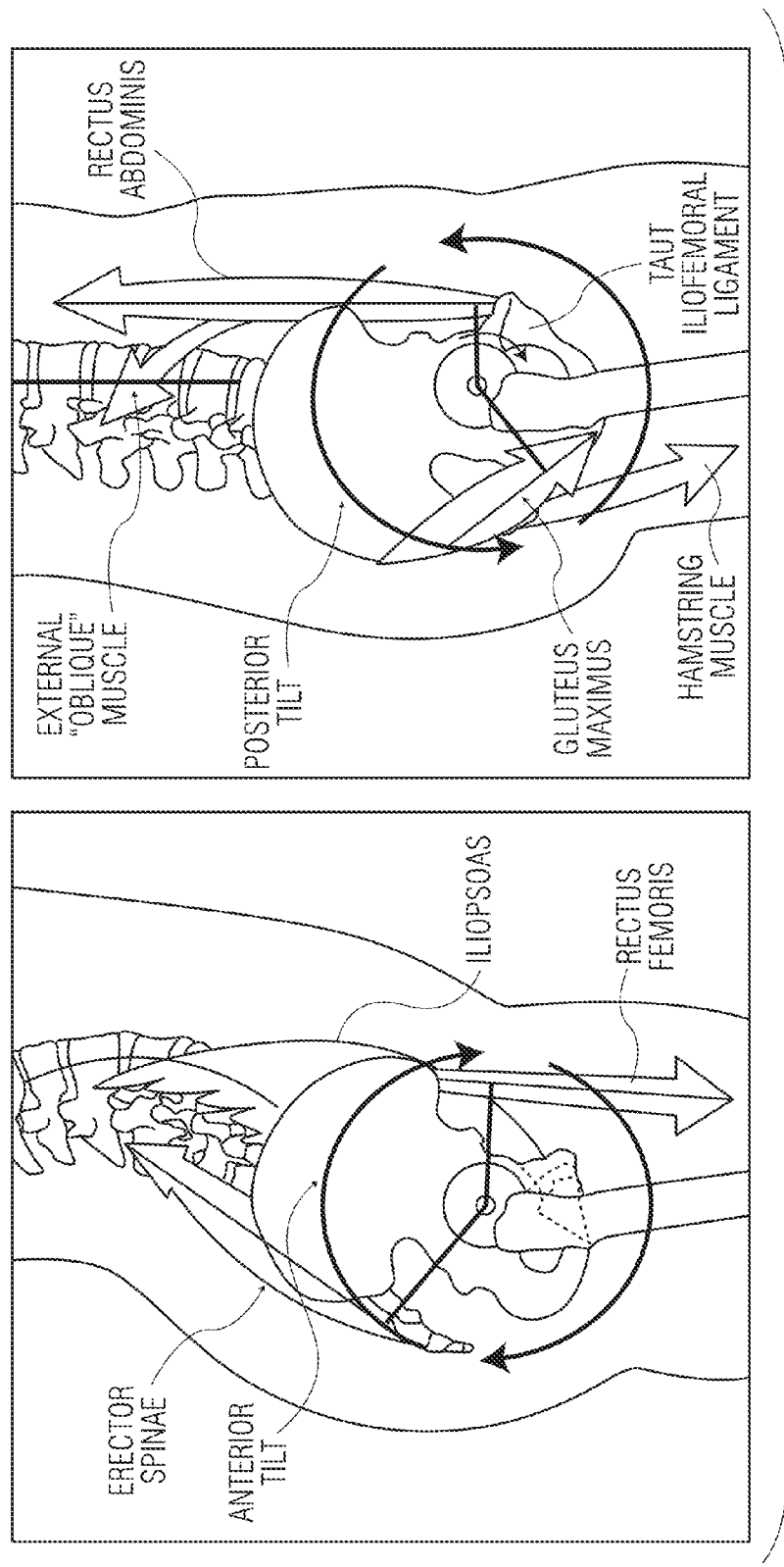

The method for aligning an insertion instrument for an acetabular cup of the present invention will now be described. It is shown in the preferable embodiment of the lateral decubitus position, however, similar method could be used for the supine position. Such an insertion instrument may be a reamer or impactor. For definitional purposes, pelvic obliquity and tilt rotation are shown respectively in FIGS. 1A, 1B and 1C. Initially a pre-operative digital standing A/P (anterior/posterior) (FIGS. 2 and 3) and lateral view x-ray (FIG. 3A) images of a pelvis 10 are taken. A magnification marker (not shown) may be included in these two x-rays.

Figure 3:
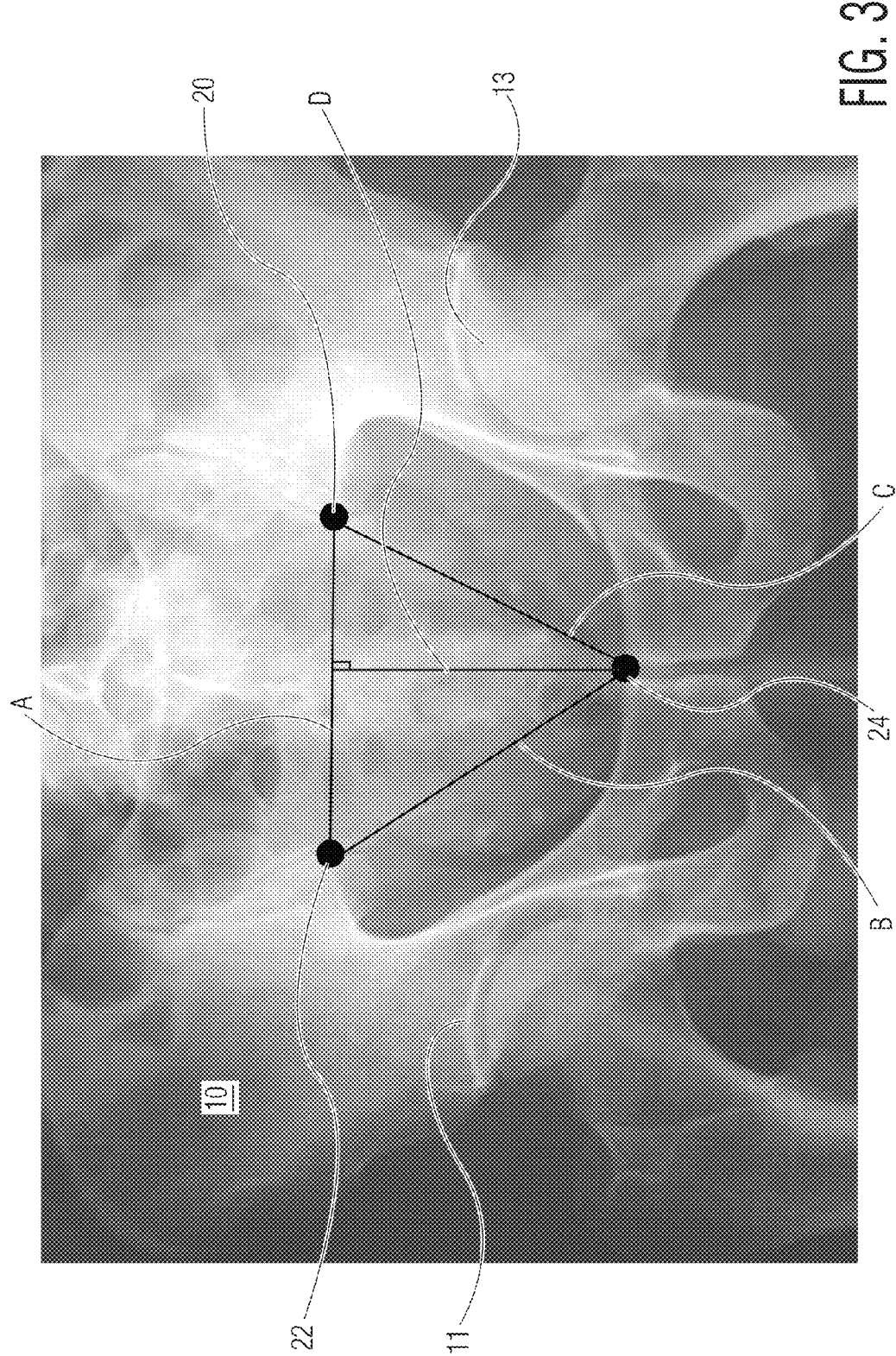
FIG. 3 shows three points on a pelvic anterior/posterior x-ray including the right and left promontory points and the pubic symphysis.

The goal of the invention is that a pre-operative x-rays (FIGS. 3 and 3A) are taken and a plan established for the best acetabular cup position (inclination and version) relative to right and left acetabulum pelvis 10 for the individual patient. The pre-operative A/P plane is reestablished the calculations relative to the intra-op pelvis position (FIG. 3).

The pre-operative cup position plan for inclination and version is then applied to the reestablished plane. In order to do this, at least some of the changes that took place in tilt, obliquity and rotation from their pre-operative position (angular changes) are determined and then used with the acetabular cup impactor. This can be done without placing any additional pins or other elements in contact with the body so other trackers can be attached to the pelvis.

In the preferred embodiment, the x-ray images are taken with the patient standing. A standing image naturally orients the pelvis to the individual patients natural pelvic tilt, obliquity and rotation.

Figure 2:
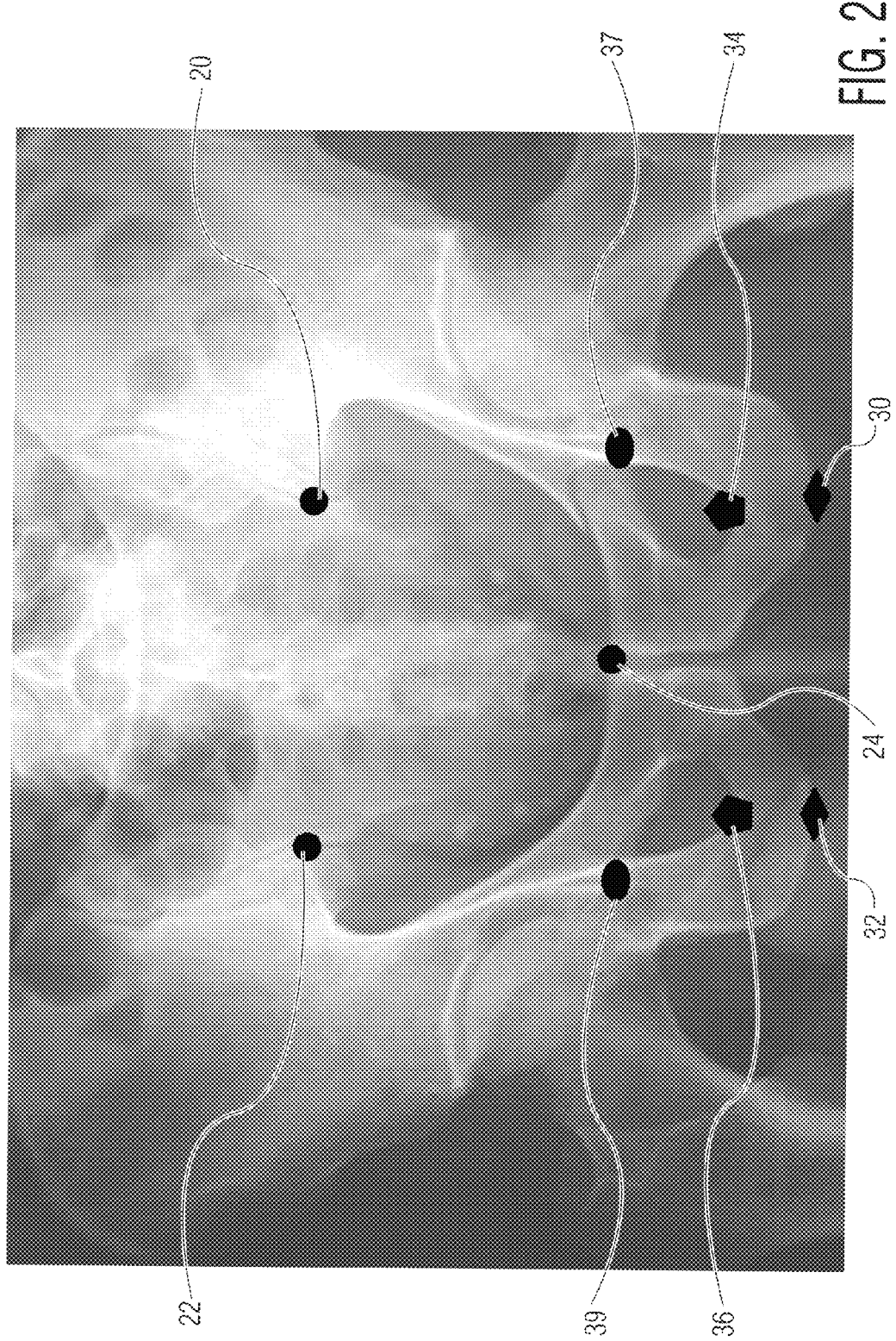
FIG. 2 shows nine possible anatomic landmarks on a pelvic anterior/posterior x-ray.
Figure 3A:
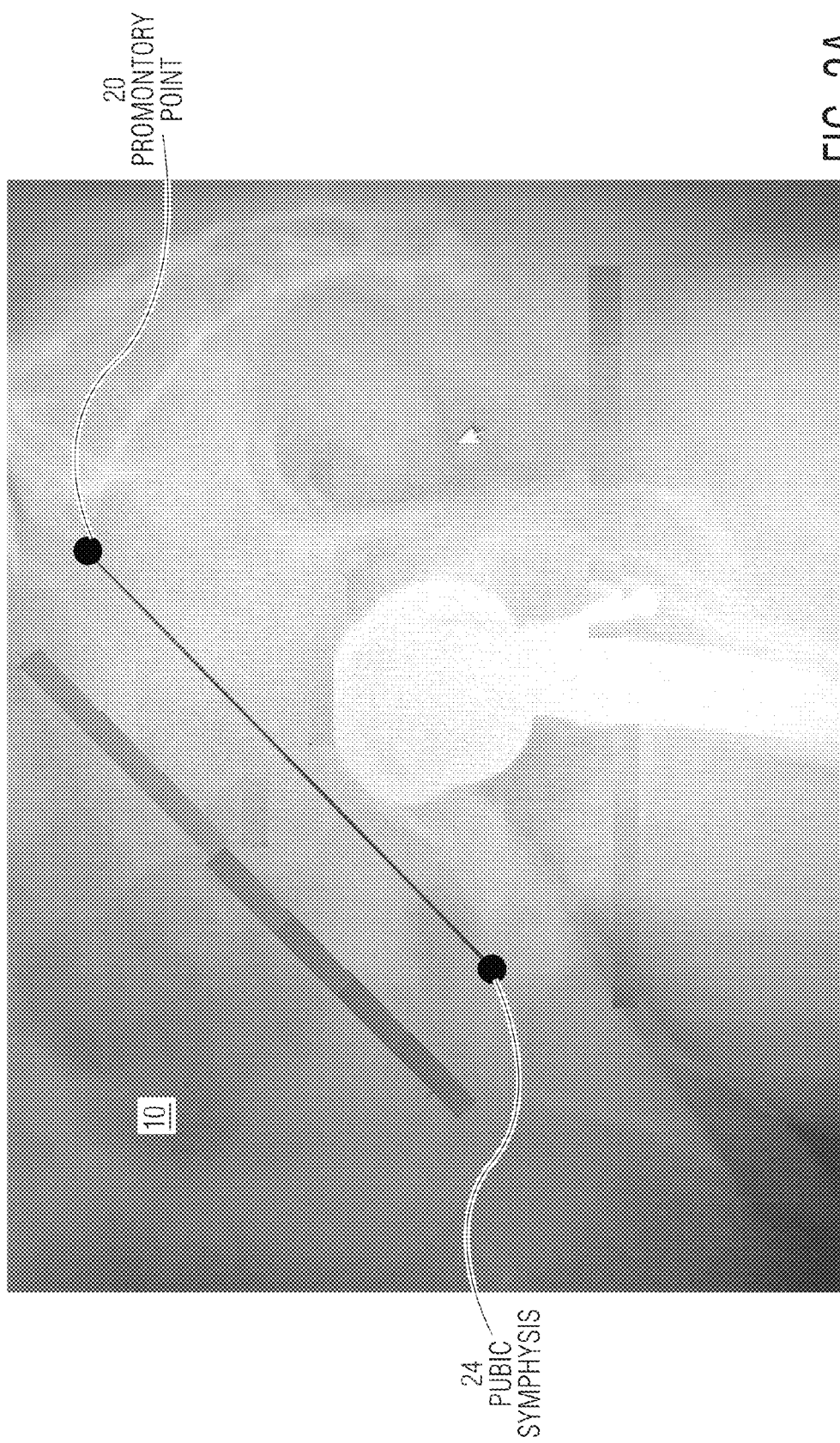
FIG. 3A shows a lateral view of a lateral x-ray showing a left promontory point located directly above the right promontory point and the pubic symphysis.

Referring to FIG. 2 to FIG. 5, the surgeon identifies at least five or more specific points on the images (three on A/P x-ray and two on lateral x-ray). The three points on the A/P x-ray are preferably the left and right promontory 20, 22 and pubic symphysis 24. The two points on the lateral x-ray are the lateral promontory point 22 and the pubic symphysis 24. Other possible pelvic anatomy points are shown in FIG. 2 as the bases of the left and right ischial rings 30, 32, the left and right inside obturator foramen 34, 36 and the left and right acetabular teardrops 37 and 39. It may not be necessary to compare every pre and intra-operative dimension to calculate tilt, rotation and obliquity changes.

Figure 4:
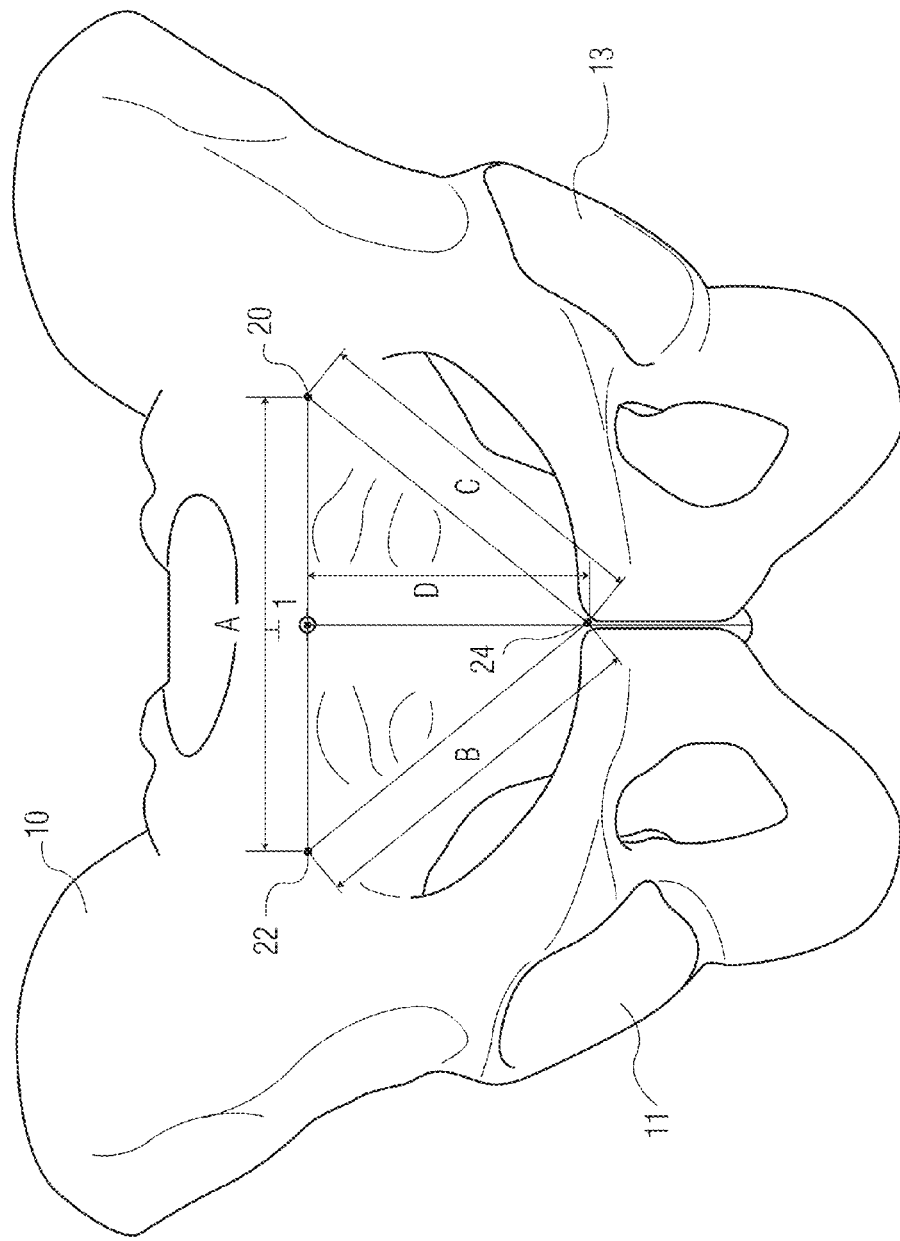
FIG. 4 shows an artist's rendition of an anterior/posterior standing x-ray showing the three points of FIG. 3 and dimensions A, B and C.
Figure 5:
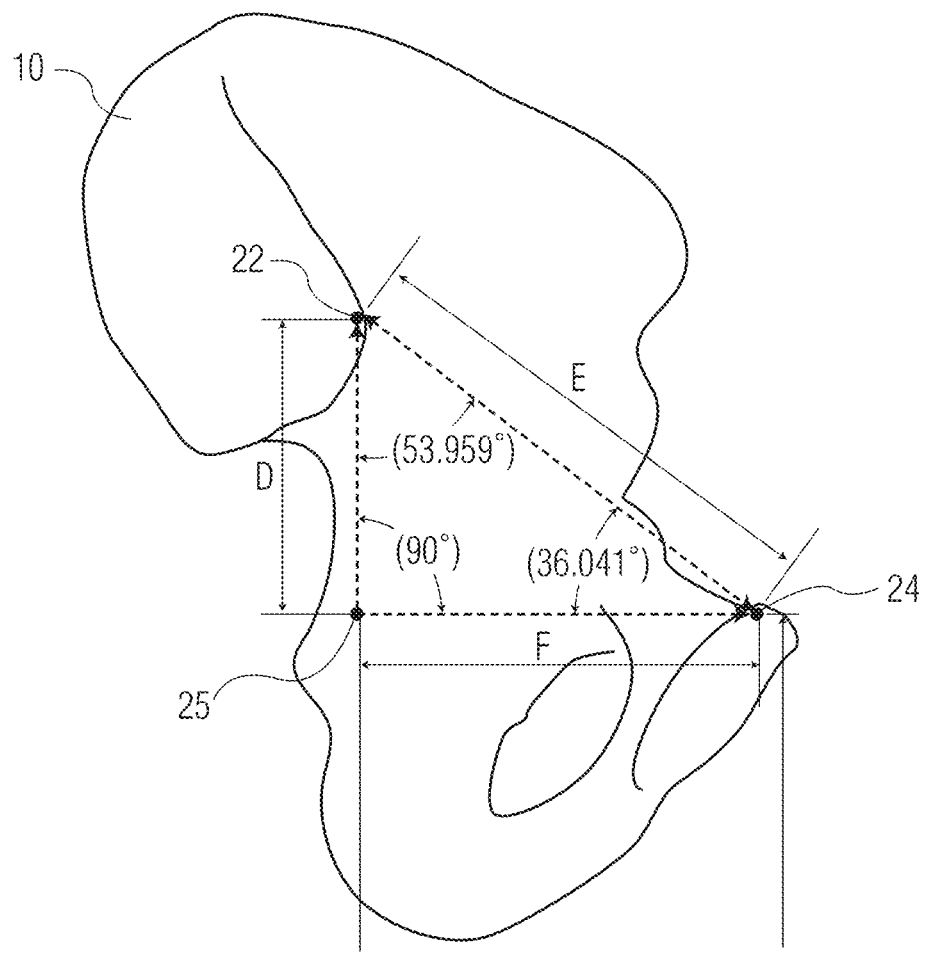
FIG. 5 shows an artist's rendition of a lateral x-ray showing the anatomic points shown in FIG. 3A including the dimensions D, E and F therebetween.

Computer software may be used to calculate lengths and angles between these five points and retains the calculated dimensions to compare to a future correlated intra-operative dimension on intra-operative x-rays. For example, FIG. 4 shows lengths A, B C and D based on points 20, 22 and 24 and FIG. 5 shows lengths D, E and F based on points 22 and 24 and a point 25 at the origin of a right triangle formed by points 22, 24.

Figure 6:
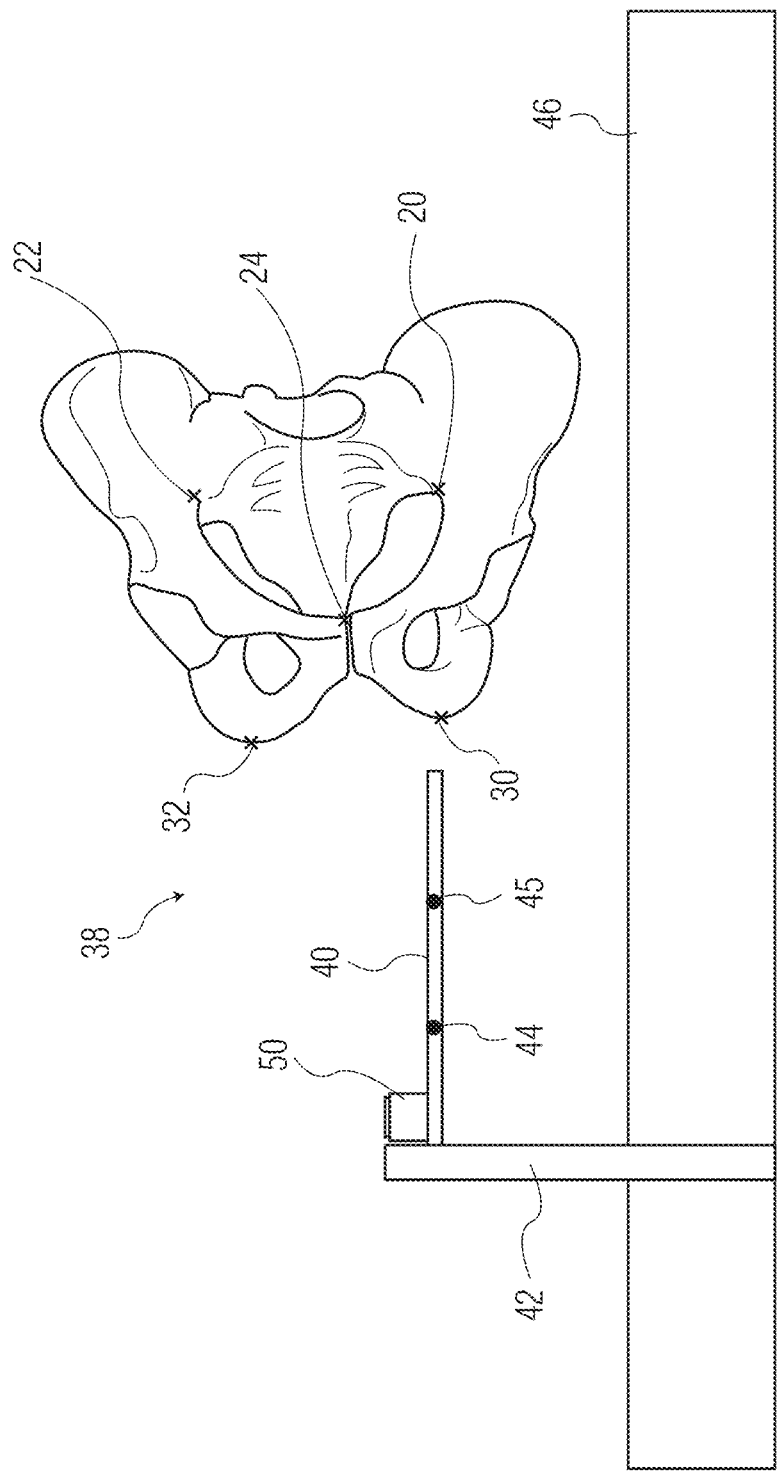
FIG. 6 shows a reference system mounted on an operating table including a radiolucent reference element and two radiopaque markers.
Figure 7:
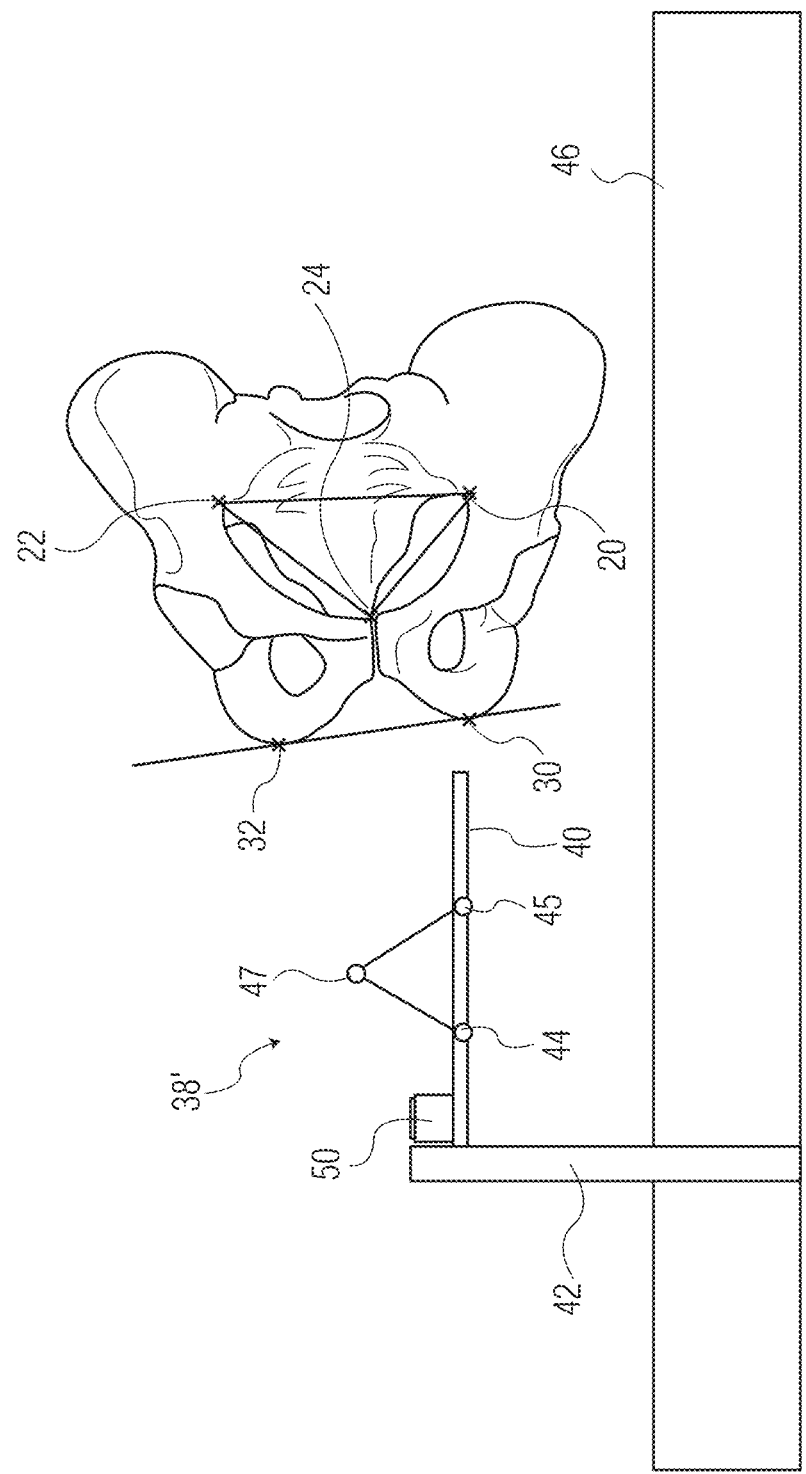
FIG. 7 shows a pelvis area of a patient located on an operating table showing the right and left promontory points, pubic symphysis and the base points of the right and left ischial rings.
Figure 25:
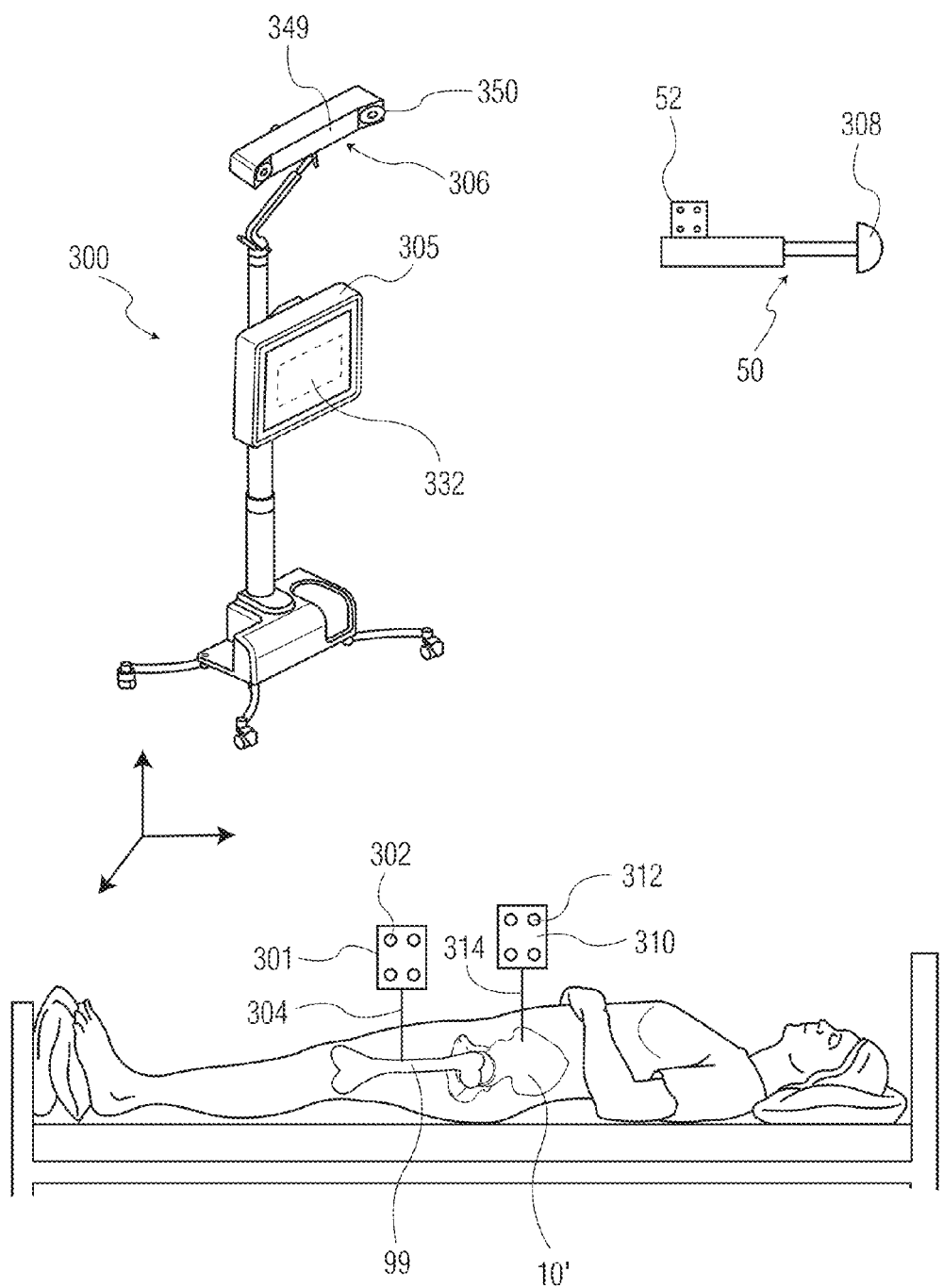
FIG. 25 is a schematic view of a typical operating room navigation or orientation system for use with the method for aligning the acetabular cup described herein.

Referring to FIGS. 6 and 7, the intra-operative routine starts with the patient being placed on an operating table 46 usually on the side opposite the hip being replaced. The surgeon performs the operation up to the point of reaming the acetabulum for acetabular cup. Prior to taking an intra-operative image, a reference plane is established. The reference plane is used to translate the angular changes to angular dimensions for a single measurement orientation system, such as a navigation system, to use to direct the reamer and acetabular cup placement. On orientation system is any system that can be used to track movements for a computer locating system. A camera tracking system including trackers mounted on the body as shown in FIG. 25. Alternately web cameras can be attached to the pelvis and track landmarks in the operating room. Referring to FIGS. 6 and 7, preferably a radiolucent reference system 38 generally denotes as (system 38) with two or three system $38^1$ of FIG. 7, radiopaque markers 44, 45 and 47, is attached to the table. Reference system 38, $38^1$ needs to be located so it is able to be included in the intra-operative x-ray image. Reference system 38, $38^1$ have a horizontal bar 40 which and can be mounted on a post 42 vertically mounted on operating table. The reference element could also be just the post with radiopaque markers, and the post could be a patient positioning post for a peg board. The reference systems 38, $38^1$ could conceivably be the actual operating room table 46. Preferably, a navigation system tracker 50 is then placed on the reference bar 40. Magnification markers could be included in or on reference bar 40. Bar 40 could be made out of radiolucent material with at least one magnification marker imbedded in the bar. The markers could be spherical in shape and the points taken could be the centers of the markers. The bar could also be make out of a semi-radiolucent material such as aluminum as shown in 8D whereas the edge of the bar itself would substitute or having radiolucent markers.

Figure 8:
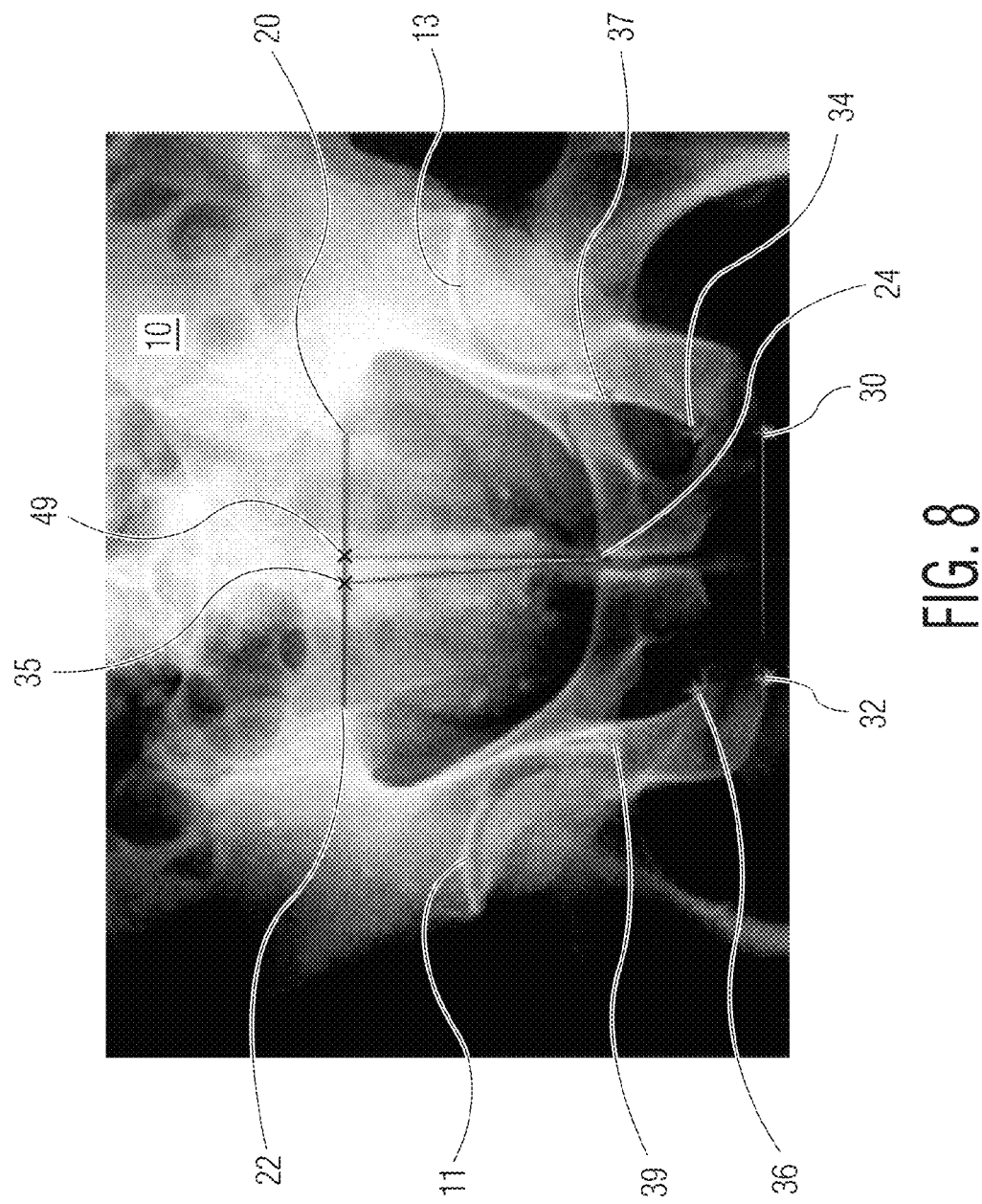
FIG. 8 is an anterior/posterior x-ray showing the anatomic landmark points on the pelvis.
Figure 8A:
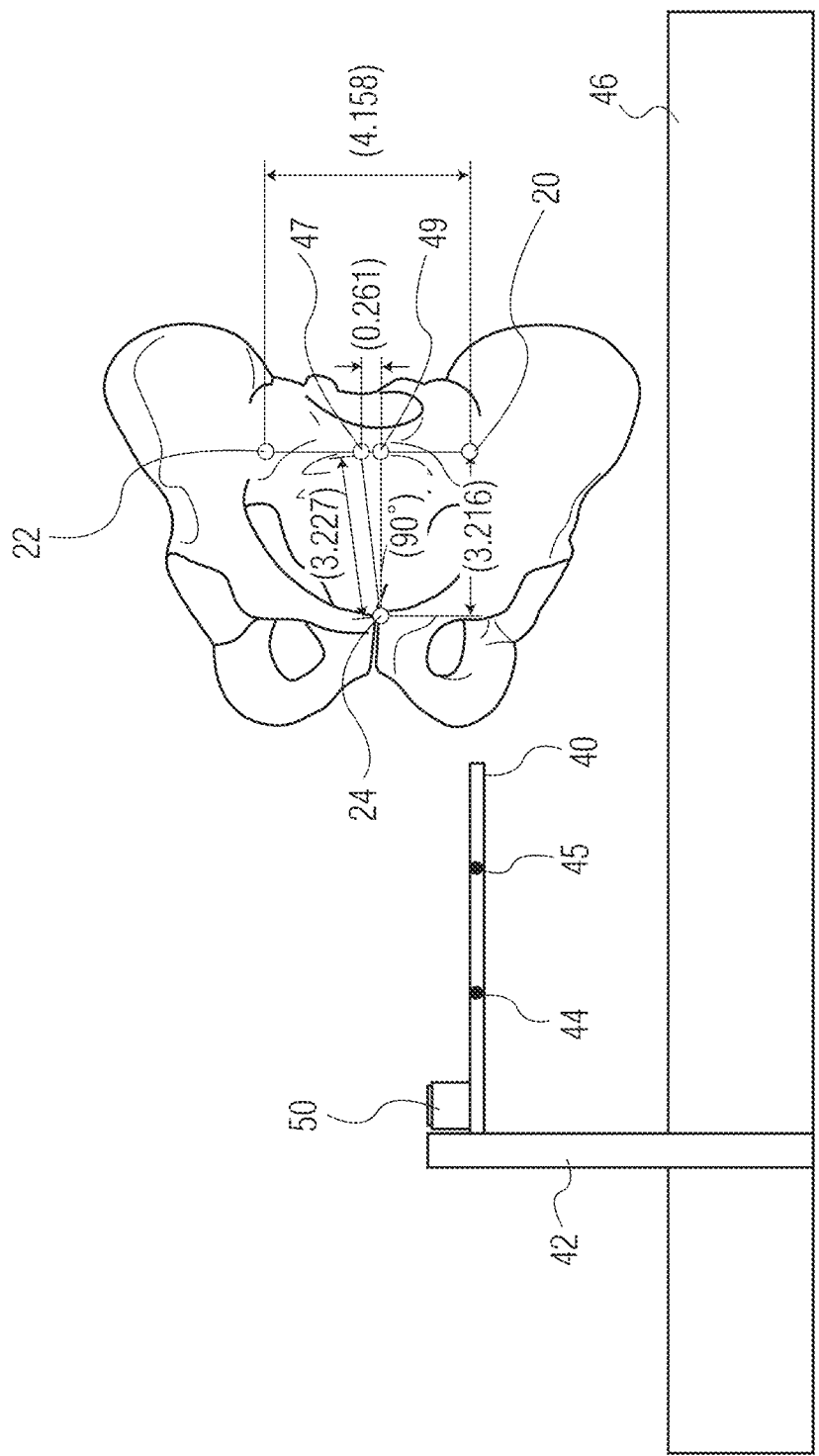
FIG. 8A is an artist's rendition of a pelvis of a patient oriented on an operating table having a reference element mounted thereon with the pelvis in a first orientation having a pelvic tilt.
Figure 8B:
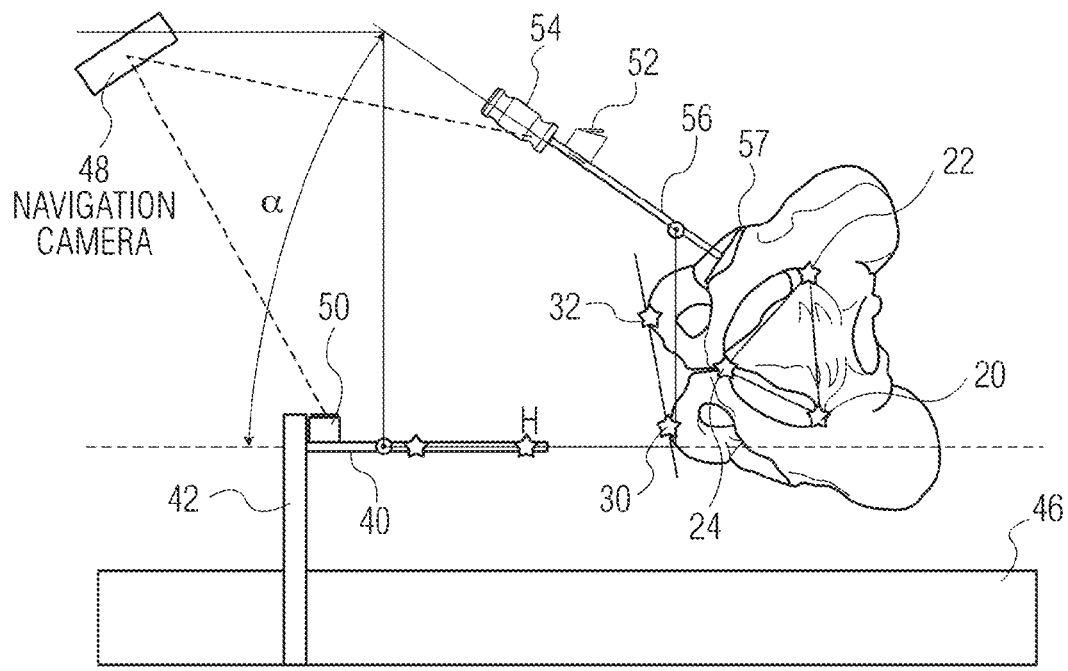
FIG. 8B is an artist's rendition of the pelvis of 8A showing the various components for a reaming operation including the chosen landmarks.
Figure 8C:
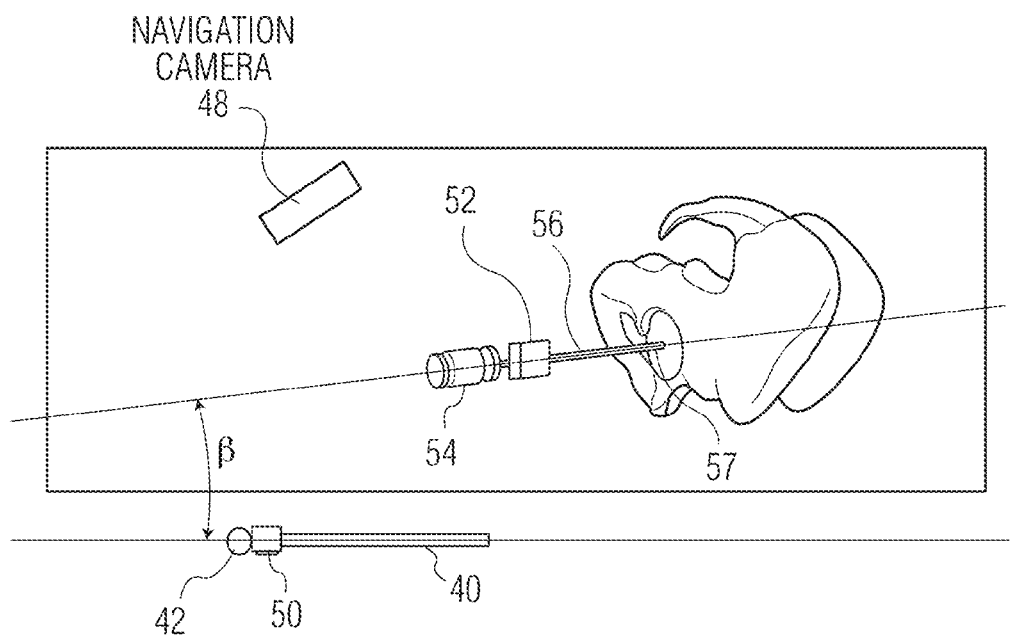
FIG. 8C is a lateral x-ray of the patient's pelvis of FIGS. 8 to 8B.
Figure 8D:
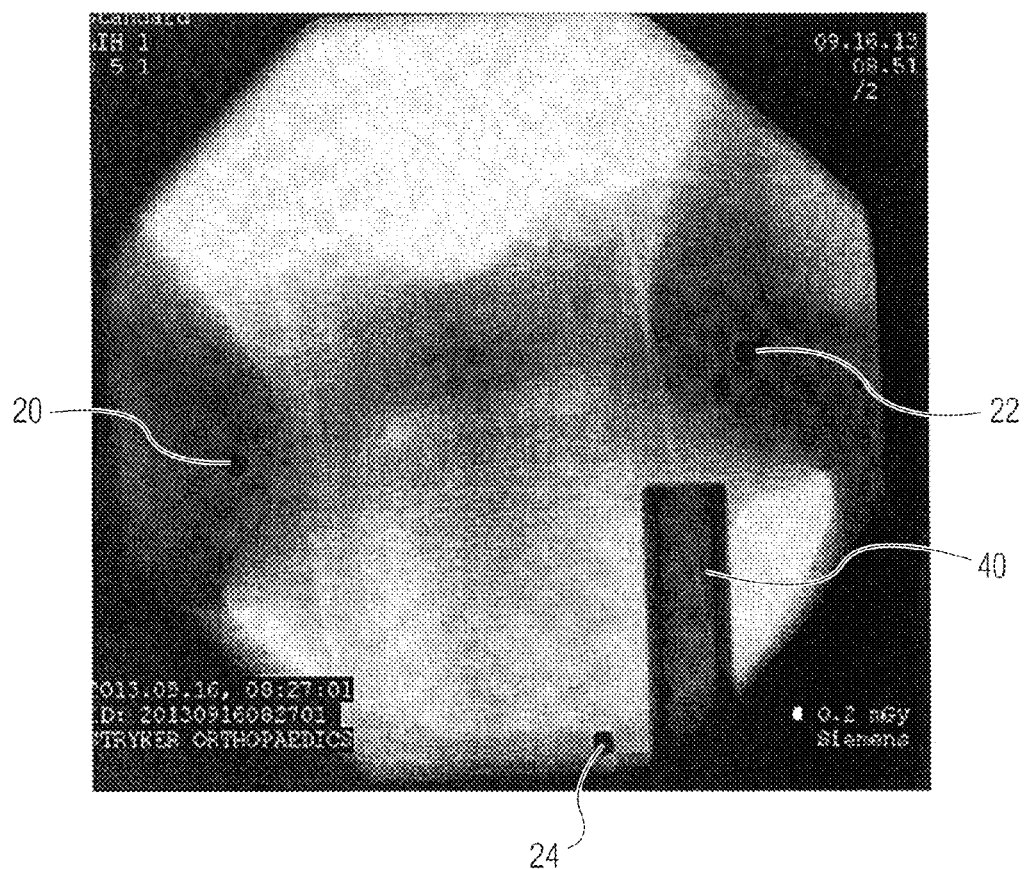
FIG. 8D is a picture of the anterior pelvic x-ray showing the guide bar and the promontory points and the symphysis.

As shown in FIGS. 8A to 8E, at least one intra-operative digital x-ray image (preferably an A/P image FIG. 8) is taken making sure the reference bar 40 is within the image (see FIGS. 8A to 8E). The surgeon identifies at least 5 specific points on the intraoperative A/P image. The preferred embodiment has the surgeon identifying seven points. The promontory points 20, 22 and pubic symphysis point 24 are similar to the pre-operative image. The two ischial ring points 30, 32 are used to detect obliquity change. (Note: Other points that are meant be symmetrical about the pelvic anatomy can be chosen. Examples are: inside left and right obturator foramen 34, 36, and left and right acetabular teardrops 37, 39. The two ischial points or other symmetrical points are chosen to make calculating the obliquity easier. The line between the two promontory points could also be used, negating the need for two other symmetrical points.), and two points on the reference element 40 are used to detect the orientation of the bar to the other points.

Figure 8E:
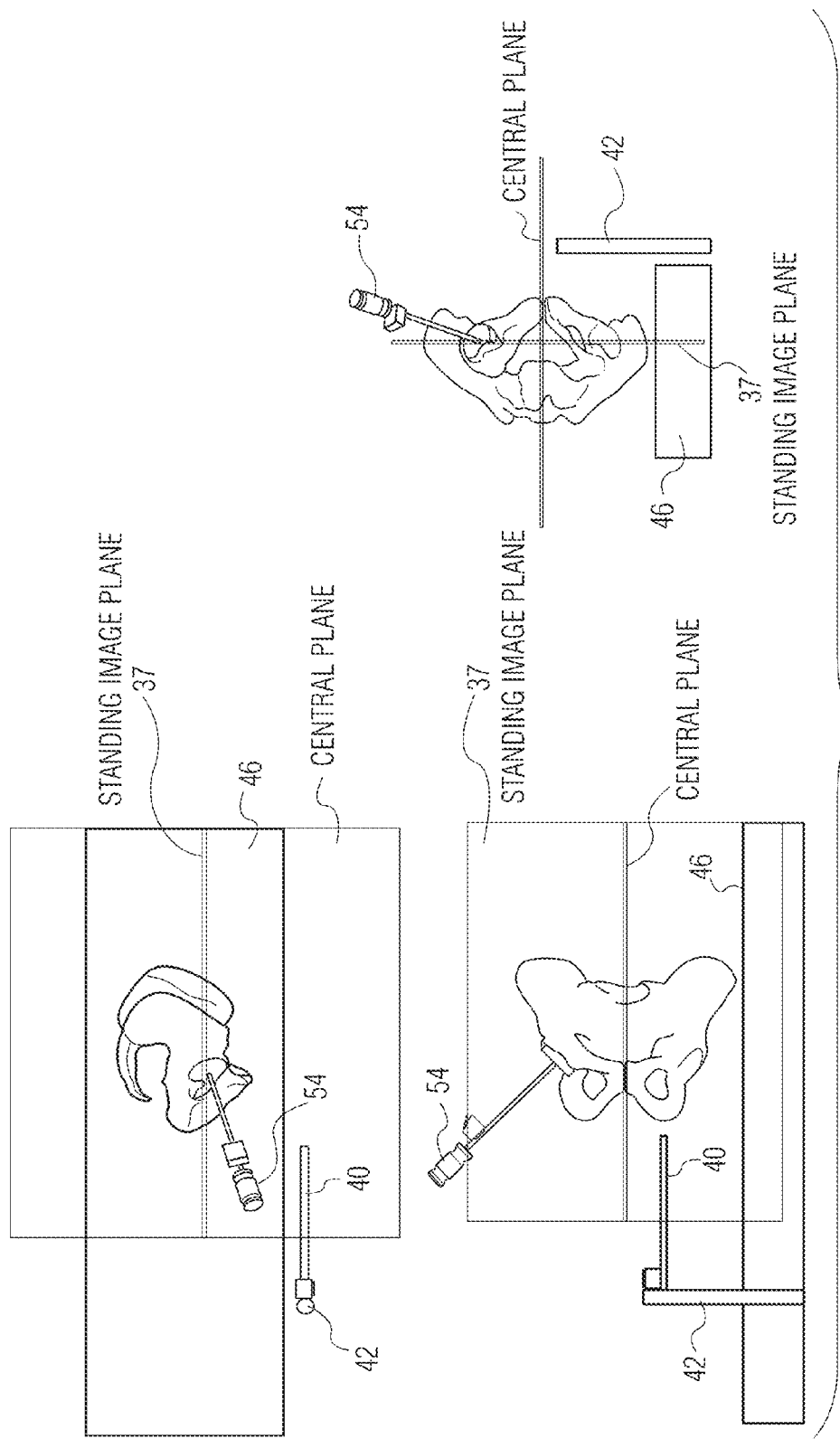
FIG. 8E shows three views of a pelvis, in an idealized position on an operating table on three standing image planes with an acetabular impactor at 45% version.

Software is used to calculate key lengths and angles between points on intraoperative image. Note that the specific points are at the center of the pubic symphysis 24, the two promontory points 20, 22, a point 37 at the center between the promontory points, and a point 49 that is 90° to the line between the promontory points. By determining the angular changes in tilt obliquity and rotation of the pelvis, the software can recreate a virtual standing image in reference to the pelvic position on the table (FIG. 8E).

The software identifies abduction and anteversion angles relative to the reference in order to achieve the pre-operative desired cup position as shown in FIGS. 3 and 4. Referring to FIGS. 5, 6, 7, 8 and 9, the preferred embodiment uses commercially available navigation system is used to determine the position of the cup impaction angle versus the reference bar 40. A tracker 50 is placed on bar 40 and a tracker 52 is placed on a cup impactor 54. Impactor 54 includes shaft 56 extending along axis 59 which engages the inside of an acetabular cup shell or reamer 5 located in acetabulum 11, 13. The impactor is adjusted to the angles α and β calculated by a computer program while looking at a monitor. Preferably, the same monitor as the digital image monitor. Alternate embodiments could obtain the desired angles via manual goniometers or protractors, or via electronic means such as with an inclinometer. Software for the required calculation is commercially available.

The surgeon then reams the acetabulum at indicated calculated angles with a standard acetabular reamer. If the surgeon suspects that the pelvis has moved prior to cup impaction, then an x-ray of the at least five points can be retaken. The surgeon impacts cup at the calculated angles α and β.

The following examples show calculations and workflow of various possible intraoperative pelvic orientations.

EXAMPLE 1

This example shows how the cup impactor is positioned relative to reference bar 40 to obtain the desired inclination and anteversion. The pelvis is shown in a perfect orientation similar to FIG. 8D.

Figure 9:
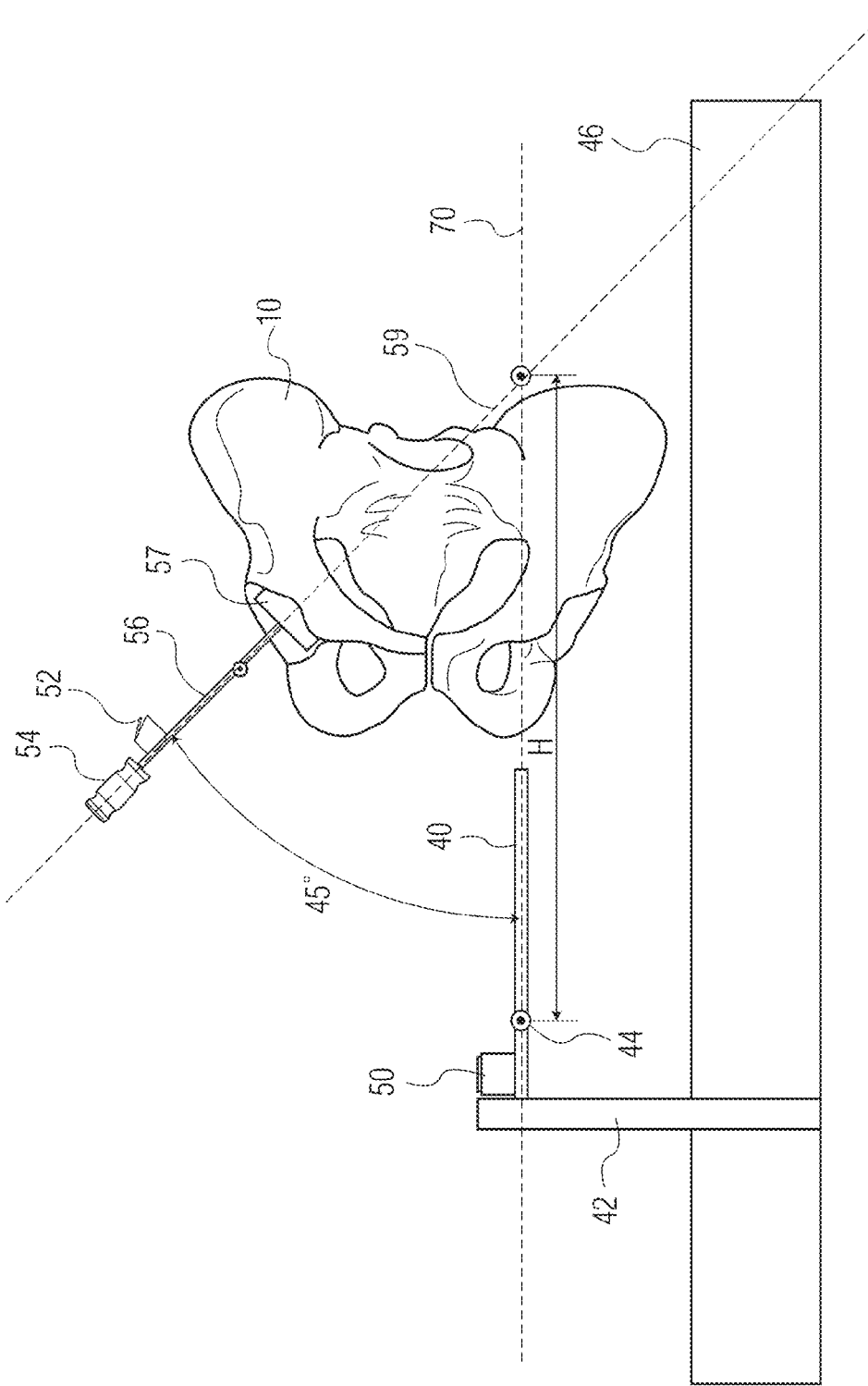
FIGS. 9 and 9A are an artist's idealized rendition of an intra-operative x-ray image taken in the anterior/posterior and lateral views of a pelvis on an operating table in a second position.
Figure 9A:
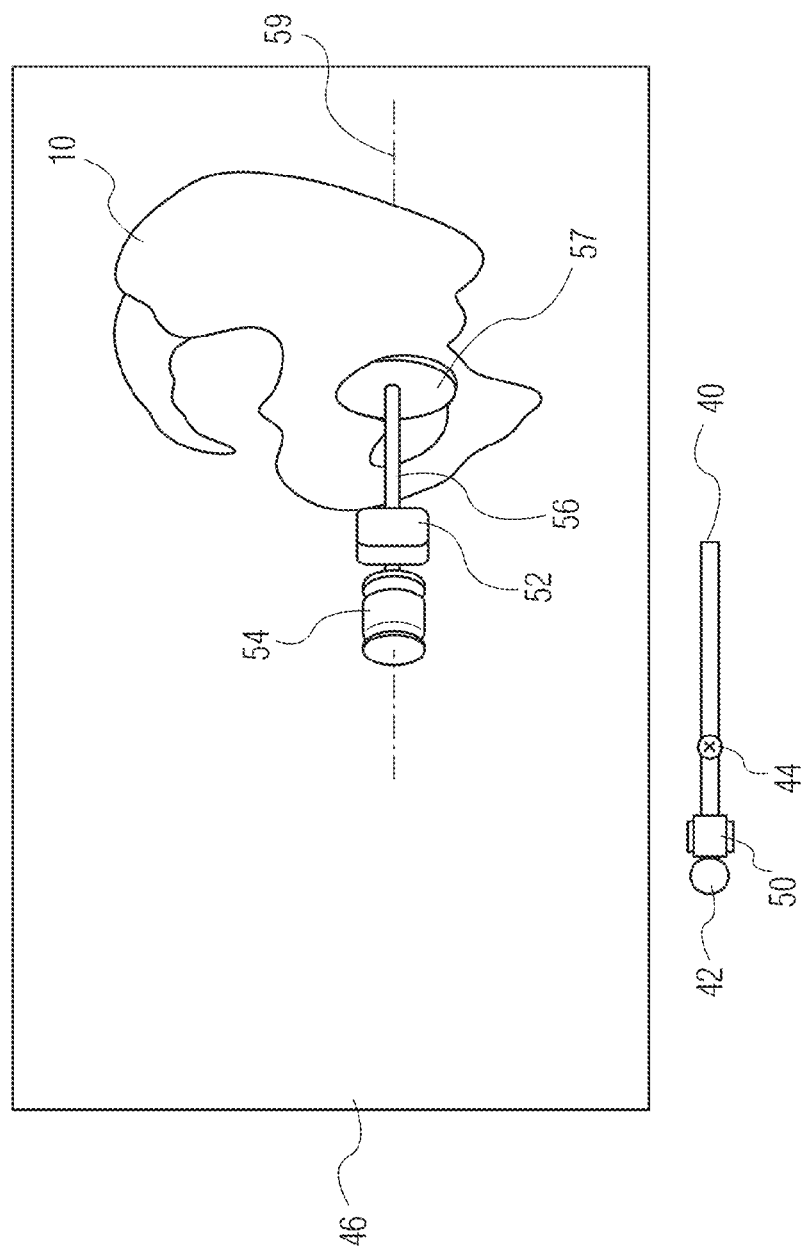

Referring to FIGS. 9 and 9A there is shown a "perfect" pelvic orientation on table 46. Also shown is the acetabular cup impactor 54 with shaft 56 shown at a 45° inclination 0° anteversion and zero tilt, rotation and obliquity with respect to reamer or impactor 57.

As shown in FIGS. 9 and 9A pelvis 10 did not alter position from the A/P image (pelvis in a perfect position) when placed on table 46. The basic pelvis orientation is exactly 90° to the standing x-ray. The plane is normal to the table. This is shown by the 0° alignment between the planes of the two x-rays (pre-standing and intraoperative prone). The plane that the standing x-ray was taken at is shown with the line 59 of FIG. 9. The plane through line 59 is normal to the table. The impactor is placed in the reamed acetabulum and rotated up to 45° in relation to the reference bar 40. In general, the plane that the standing x-ray was taken at is first found, and then impactor 54 is angled for inclination along that plane, and then anteversion is placed normal to the plane by pivoting in the acetabulum (in example 1 this is 0°). The bar 40 defines the plane normal to the intra-operative x-ray view and parallel to the front edge of the table. It is perpendicular to the cross-table x-ray image taken in the operating room. The front edge of the operating room table could also be used as a reference, however, the size of the x-ray image may not be able to capture both the table and the anatomy required in the same shot. Having a reference bar 40 attached to the table allows it to be moved to a position that is within the image and not blocking the anatomic points needed for the calculations. The navigation tracker 50 is attached to whatever the reference is, whether it be the bar or the table itself.

Figure 10:
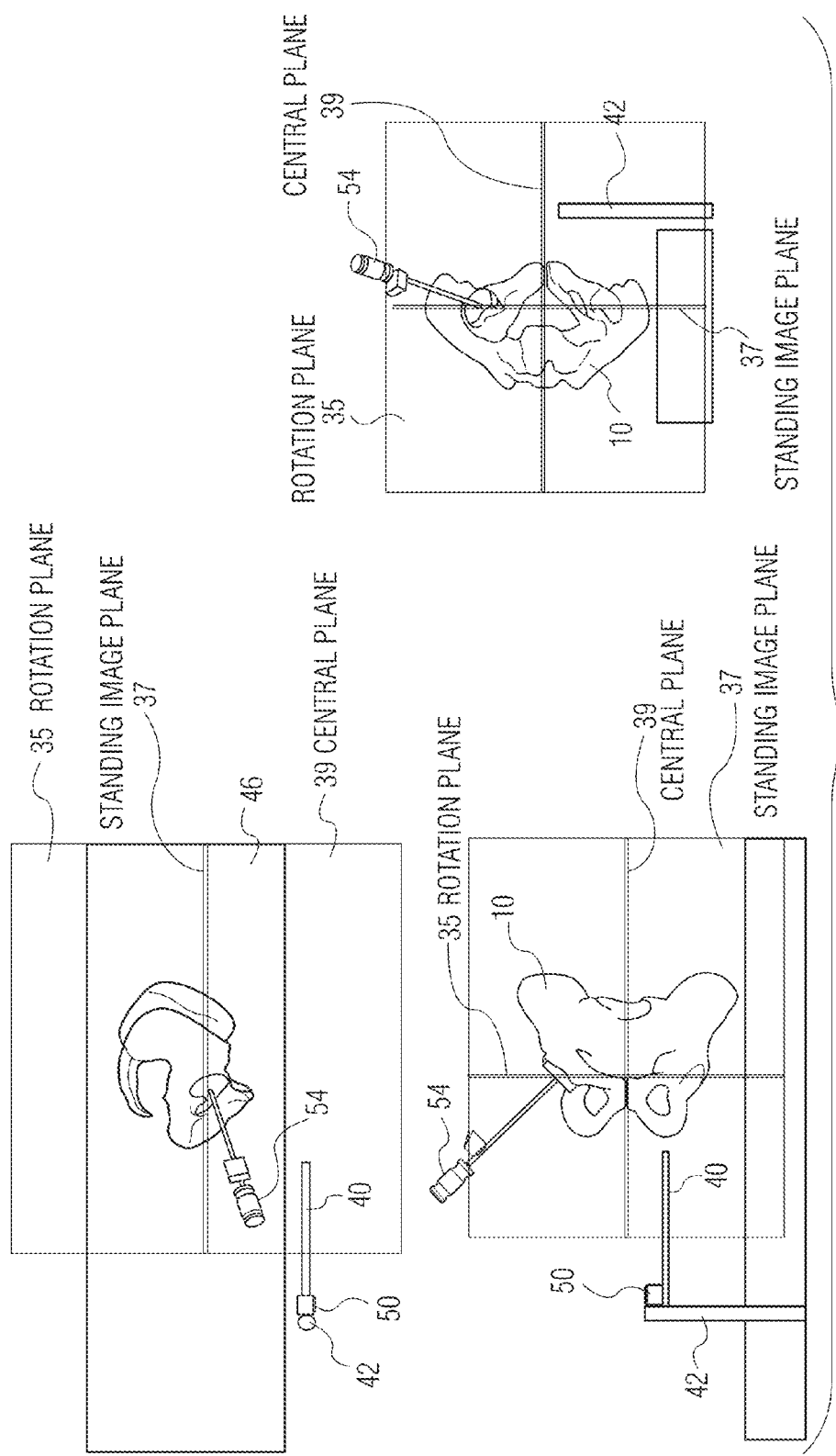
FIG. 10 shows an example of pelvis shift in the standing plan x-ray when a patient is placed on an operating table.

Referring to FIG. 10, the navigation system first recreates the standing x-ray plane 37, defines a central plane 39 then calculates the amount the pelvis has moved off that reference plane. A rotational plane 35 is also shown. Reference bar 40 defines plane normal to x-ray view and parallel to table.

EXAMPLE 2

Figure 10A:
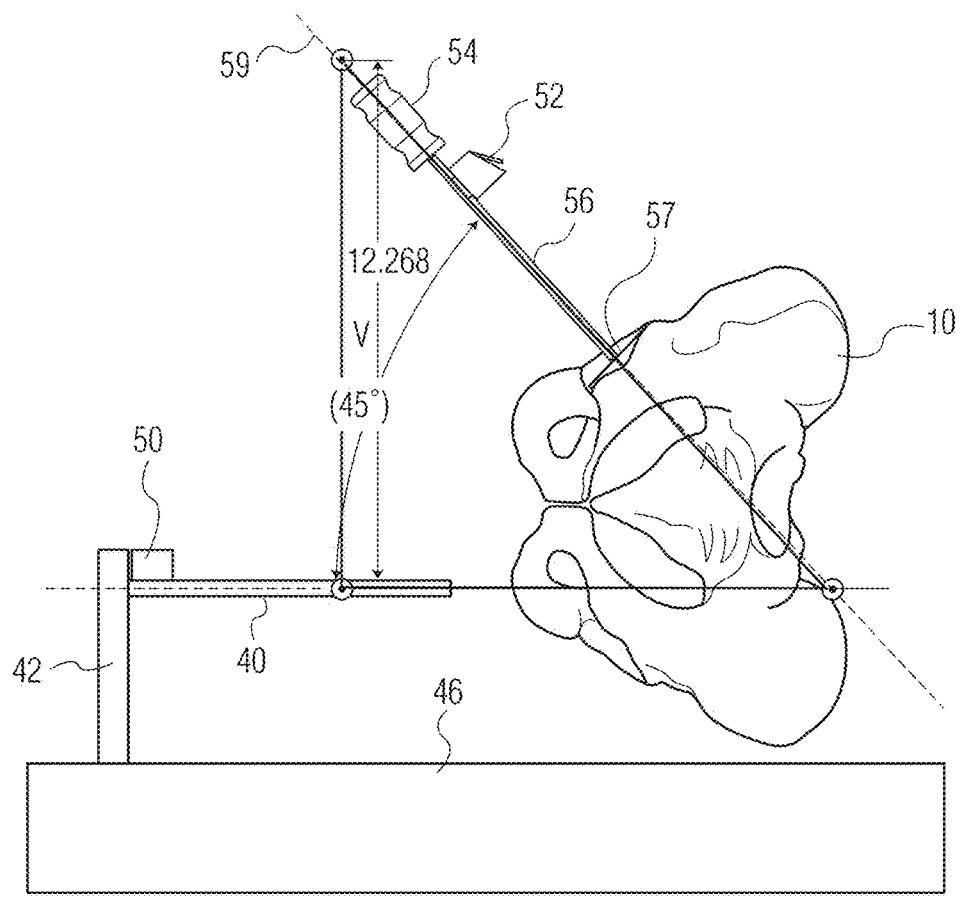
FIGS. 10A and 10B are anterior and posterior intra-operative views of a pelvis on an operating table showing 45° inclination and 20° anteversion.
Figure 10B:
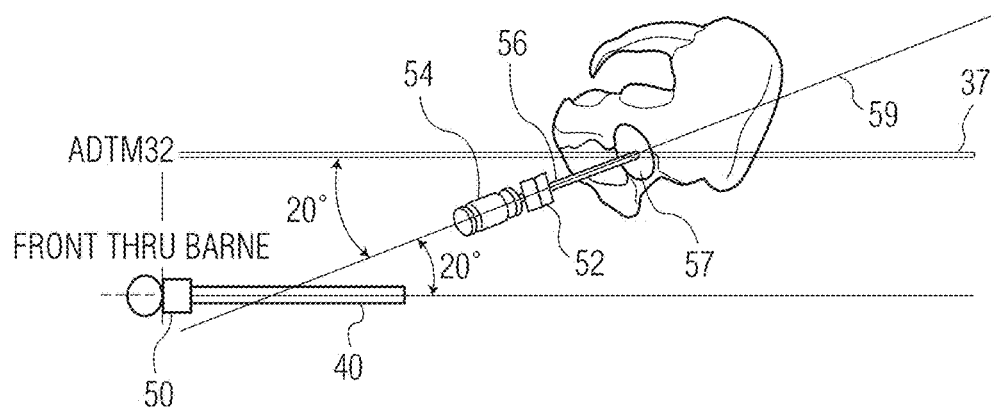

Referring to FIGS. 10A and 10B, similar "perfect" pelvic orientation on the OR table as with Example 1. Standing x-ray plane is normal to the table shown with acetabular cup impactor at a now desired 45° inclination (FIG. 10A) and 20° anteversion (FIG. 10B). The cup impactor 54 would be oriented 45° from the reference bar 40 and 20° off the reference bar 40. The two navigation trackers 50, 52, one of the reference bar, and one on the impactor helps facilitate finding these angles for the impactor. The orientation is now 45 DEG INCLINATION, 20 ANTEVERSION, 0 TILT, 0 ROTATION and 0 OBLIQUITY.

EXAMPLE 3

Figure 11A:
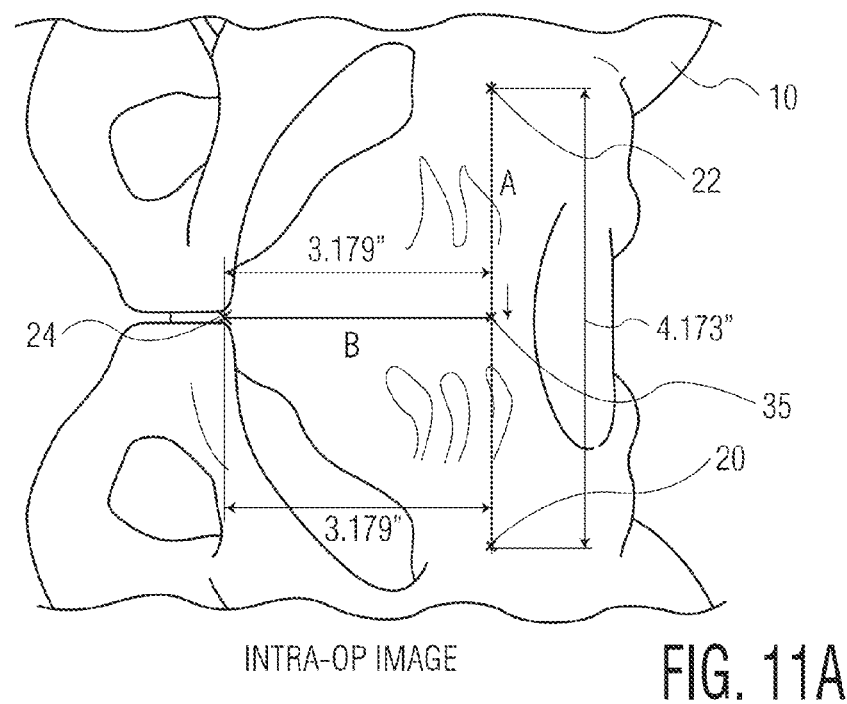
FIG. 11A shows the pelvis when there is a 10° tilt.
Figure 11B:
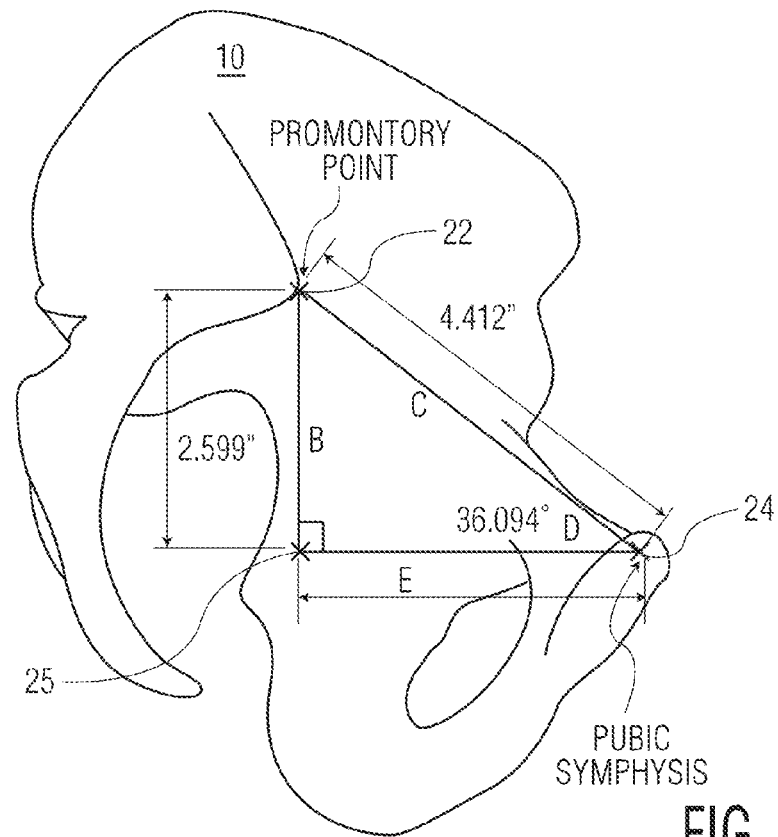
FIG. 11B shows the lateral view of FIG. 11

Here the cup impactor orientation is 45° INCLINATION, 20° ANTEVERSION, AND THE PELVIC ORIENTATION IS 10° TILT (to be confirmed below), 0° ROTATION and 0° OBLIQUITY. Dimensions for calculations for determining amount of tilt are pre-op images are shown in FIGS. 11, 11A and 11B. Intra-op image: A/P image shown in FIG. 11A: May have tilt. This is to be verified by the calculation outlined below. A Pre-op A/P, preferably standing image is taken and shown in FIG. 11. An Intra-operative A/P image is taken and shown in FIG. 11A. The 3.179 dimension between points 24 and 35 is compared to the pre-op dimension of 2.599 between points 24 and 49. Since the 3.179 is greater than 2.599, it indicates that the pelvis has tilted forward (positive tilt) by a certain amount. Dimensions for calculations for determining amount of tilt: A pre-operative lateral image is shown in FIG. 11B with lengths B, C, and E and angle D.

Table 1 refers to the dimensions of FIGS. 11A and 11B.

TABLE 1

| Letter | Name Given | Feature length/angle | Pre-op | Intra-op |
|---|---|---|---|---|
| A | Promontory Line | Between Promontory points | 4.173 | 4.173 |
| B | Normal Line | On A/P Image: (90 deg) between Prom Line and Pub Sym. On Lateral Image: vertical distance between Prom pts and Lat Image Horizontal Line | 2.599 | 3.179 |
| C | Lateral Image Hypotenuse | Promontory to Pub Sym | 4.412 | N/A as no lat image taken but 4.412 remains the same |
| D | Lateral Image Tilt Angle | Angle between Hypotenuse and line parallel to floor | 36.094 deg | To be calculated |
| E | Horizontal Line | Pre-op line parallel to the floor or OR table | Not important as no rotation | N/A |
|  | Tilt Angle | Relative change in pelvic tilt from the pre-op angle D to the intra-op angle D |  |  |

Figure 11C:
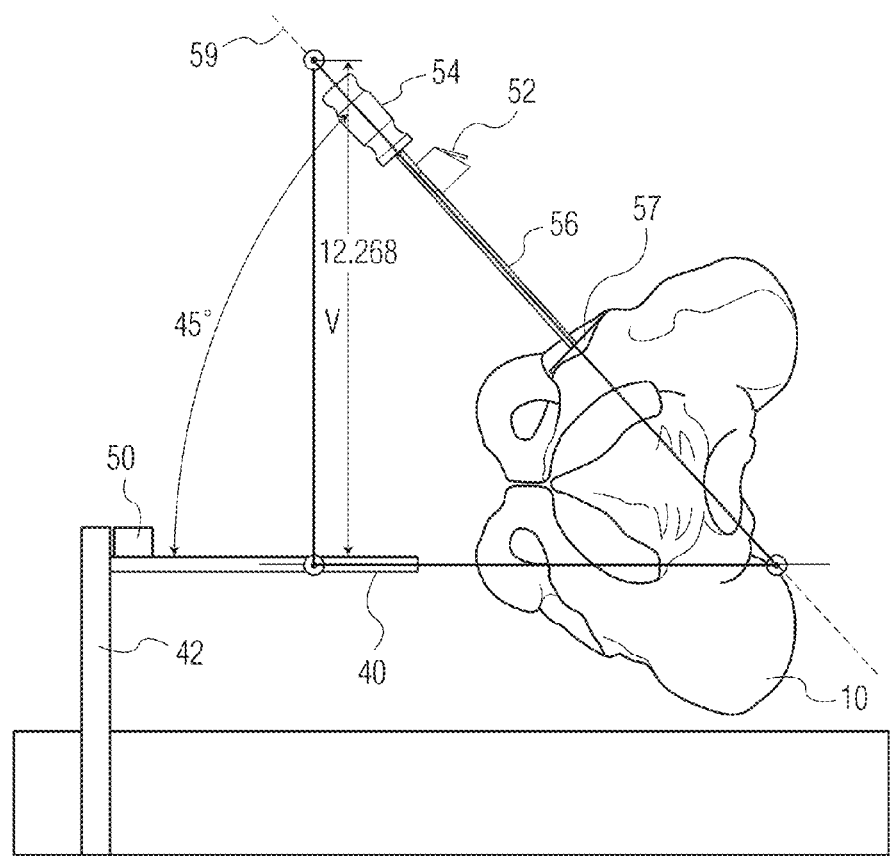
FIGS. 11 through 11D show the reorientation of the acetabular cup impactor/reamer from a pre-operative plan based on a standing x-ray to an intra-operative plan accounting for movement of the pelvis with 10° tilt.
Figure 11D:
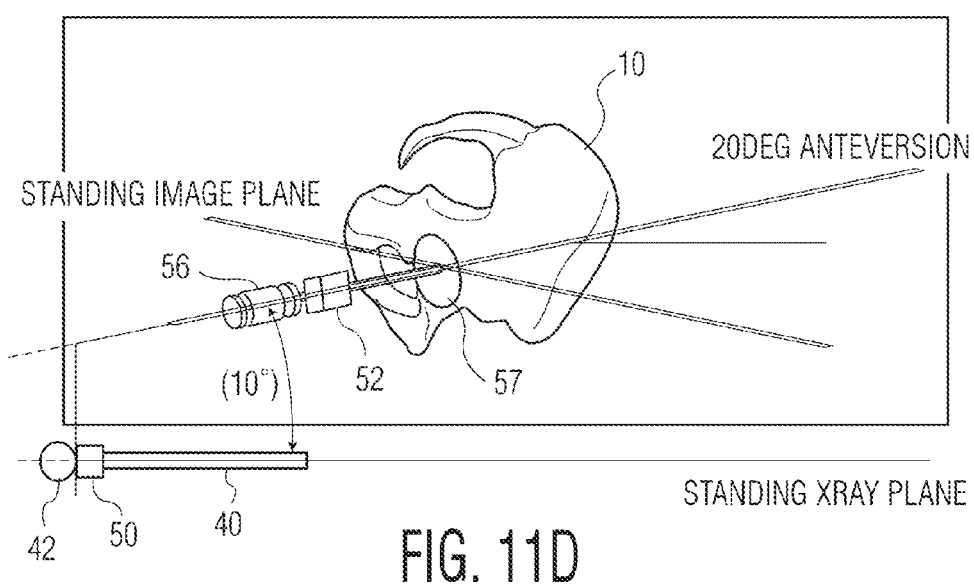

From FIGS. 11A and 11B: Sin angle D=3.179/4.412
Angle=46.098 deg (intra-op angle D)
Tilt angle=angle of intra-op image minus angle of standing image
Tilt angle=46.098−36.094
Tilt angle~10 degrees
FIGS. 11C and 11D show what angles the navigation would set the impaction at.
Inclination=45 deg (remains unchanged)
Version=20 deg anteversion minus 10 deg positive tilt=10 deg as shown

EXAMPLE 4

Figure 12:
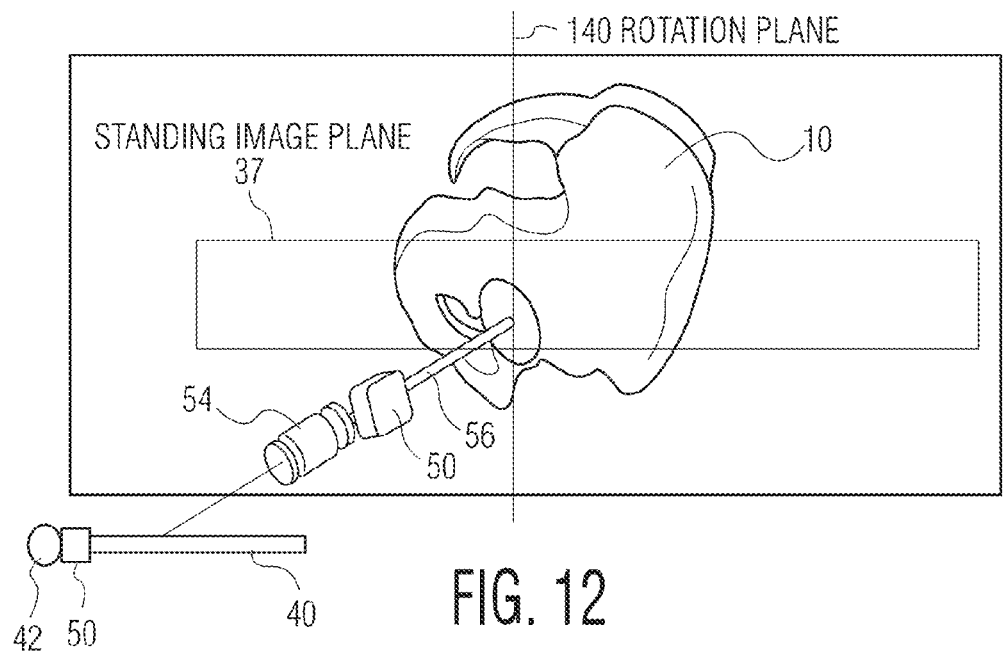
FIGS. 12 through 12L show the repositioning of an acetabular cup impactor/reamer from an inter-operative plan of 45° inclination and 20° anteversion with 8° rotation of the pelvis when placed on an operating table as set forth in example 4 of the present application.
Figure 12A:
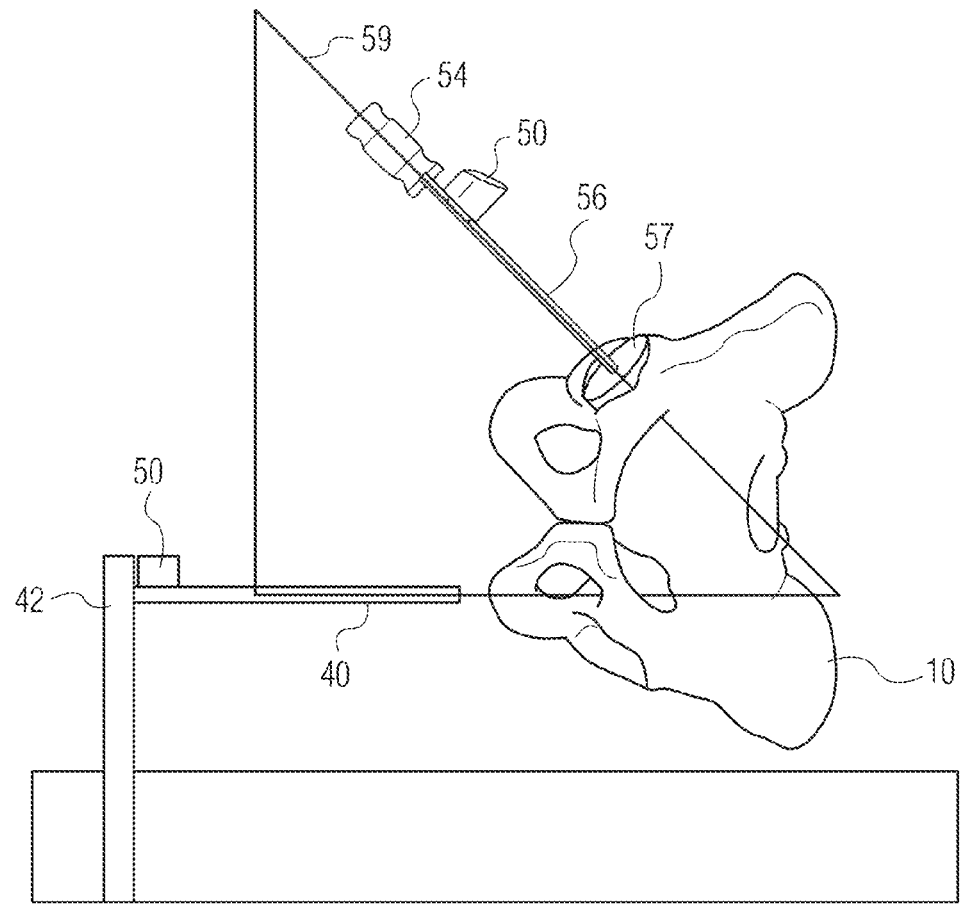
Figure 12D:
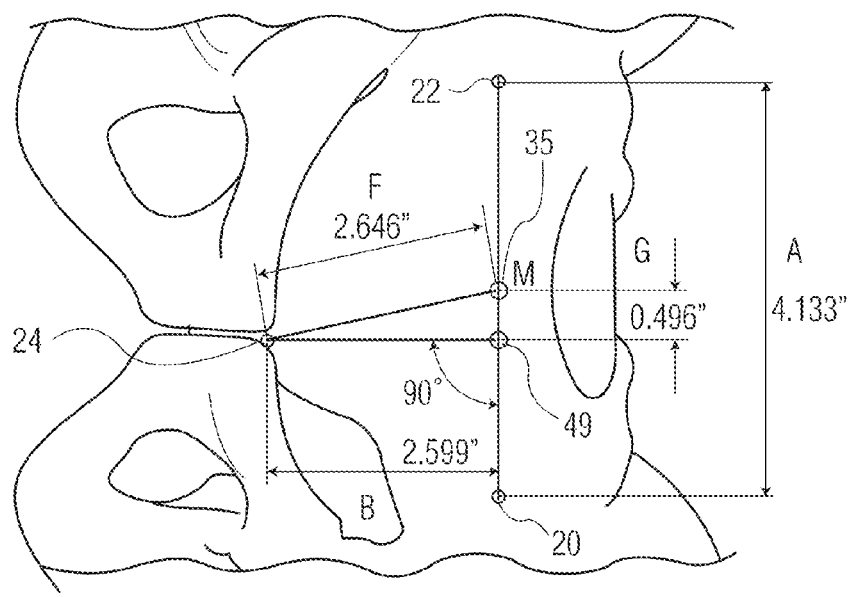
Figure 12E:
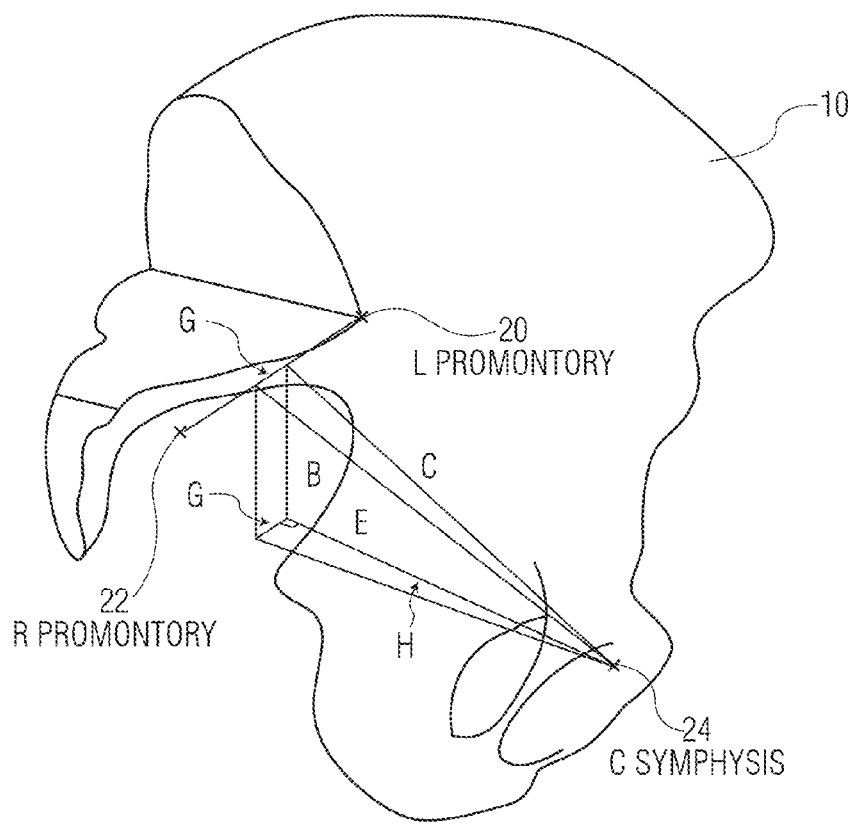

The cue orientation pelvic orientation in this example is 45 DEG INCLINATION, 20° ANTEVERSION, and the intra-operative pelvic orientation is 0° TILT, 8° ROTATION (to be confirmed below) and 0° OBLIQUITY. FIGS. 12 and 12A show an inter-operative top view (FIG. 12) and front view (FIG. 12A) of what a pelvis at 8 deg of Rotation looks like. FIG. 12 shows standing x-ray plane 37 and rotational plane 140. Calculations for determining amount of rotation: Previously (similar to FIGS. 11 and 11C) taken pre-operative images are shown in FIGS. 12B and 12C. FIGS. 12D and 12E are A/P Intra-operative images which show the pelvis may have rotated. This is to be verified. The following table 2 refers to the dimensions in FIGS. 12B to 12E.

TABLE 2

| Letter | Name Given | Feature length/angle | Pre-op | Intra-op |
|---|---|---|---|---|
| A | Promontory Line | Between Promontory points | 4.173 | 4.133 |
| B | Normal Line | On A/P Image: (90 deg) between Prom Line and Pub Sym. On Lateral Image: vertical distance between Prom pts and Lat Image Horizontal Line | 2.599 | 2.599 |
| C | Lateral Image Hypotenuse | Promontory to Pub Sym | 4.412 | N/A as no lat image taken but remains the same |

TABLE 2-continued

| Letter | Name Given | Feature length/angle | Pre-op | Intra-op |
|---|---|---|---|---|
| D | Lateral Image Tilt Angle | Angle between Hypotenuse and line parallel to floor | 36.094 deg | N/A as no lat image taken but remains the same |
| E | Horizontal Line | Pre-op line parallel to the floor or OR table | Not important | To be calculated |
| F | Midpoint Line | Line between Prom Line Midpoint and Pub Sym | Not important | Not important |
| G | Rotational Offset Distance | Distance between Normal Line and Midpoint Line on Promontory Line | 0 | 0.496 |
| H | Rotational Angle | Angle of Pelvic Rotation of Intra-op relative to Pre-op | 0 | To be calculated |

Rotational Angle

Referring to FIG. 12E to find the Rotation Angle (H), first find length E.

$$B^2 + E^2 = C^2$$

$$E^2 = C^2 - B^2$$

$$E^2 = (4.412)^2 - (2.599)^2$$

$$E = 3.565$$

Figure 12F:
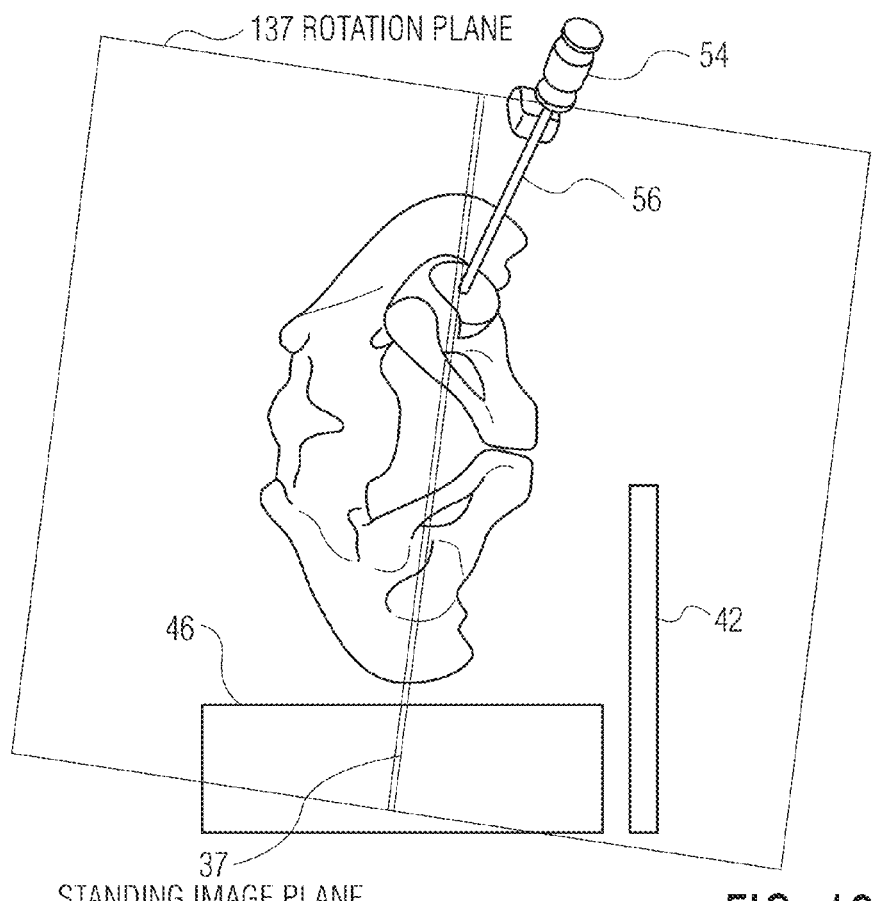
Figure 12G:
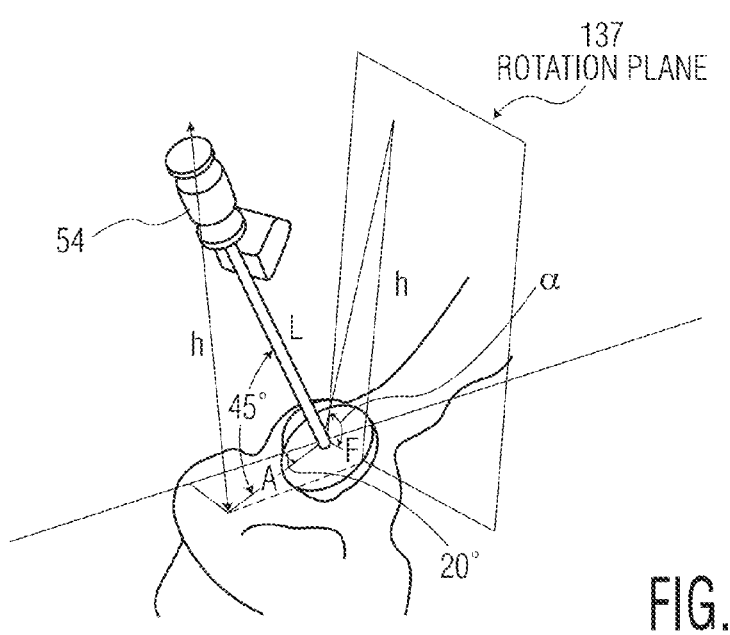

The Lateral Image Horizontal Line dimension E found above, 3.565", is now used to help calculate the amount of intra-operative pelvic rotation. The Rotational Offset Distance (0.496"), FIG. 12D, was found on the intra-op digital image device. Using these two numbers, the Rotational Angle can be found.
Sin H=0.496/3.565
Rotational Angle H=7.997 deg
The pelvis has rotated nominally 8 degrees
Note:
A less optimal way of determining the degree of rotation would be to compare the pre-op Promontory Line distance (4.173) to the intra-op distance (4.133). The 4.133 distance is a projection of the 4.173 distance at the rotation angle.
  Cos rotation angle=4.133/4.173
Rotation angle=7.939 degrees
FIG. 12F shows what 8 degrees of rotation looks like from a side view with sanding x-ray plane 37 and rotation plane 137.
  Calculations for finding the impactor angles to be used by Navigation are shown in FIGS. 12G to 12J.
  Step 1: Project the impactor angle position (45/20) onto the plane of angle change. In this case it is the Rotation Plane shown in FIG. 12G.

$$TAN\ 45° = \frac{h}{R}$$

$$SIN\ 45° = \frac{h}{L}$$

$$COS\ 45° = \frac{R}{L}$$

$$SIN\ 20° = \frac{B}{R} \qquad F = SIN\ 20°\ R$$

$$F = (SIN\ 20°)(COS\ 45°)L$$

$$TAN\ \alpha = \frac{h}{F}$$

$$TAN\ \alpha = \frac{\sin 45°\ L}{(\sin 20°)(\cos 45°)L}$$

$$\alpha = 71.118°$$

Figure 12H:
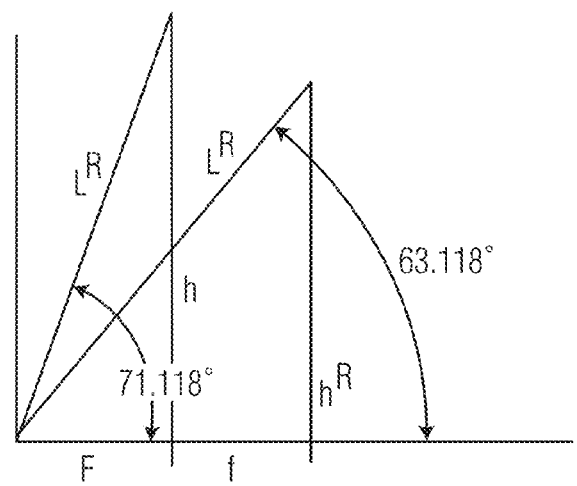

Step 2: Rotate 8° as shown in FIG. 12H (71.118−8°).

$$\cos 71.118° = \frac{F}{L^R}$$

$$\cos 63.118° = \frac{(F+f)}{L^R}$$

$$\frac{F}{\cos 71.118°} = \frac{(F+f)}{\cos 63.118°}$$

$$\frac{F}{.3236} = \frac{F}{.4521} + \frac{f}{.4521}$$

$$F = .7157F + .7157f$$

$$.2843F = .7157f$$

$$f = .3973F$$

Figure 12I:
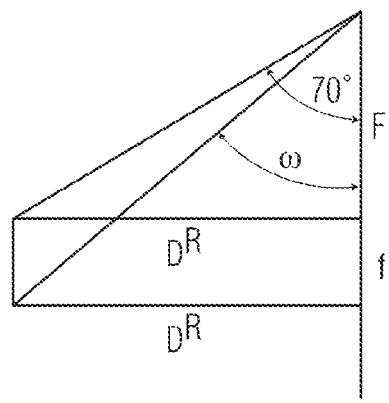

Step 3: As shown in FIG. 12I.
From Before:

$$F = (\cos 70°)(\cos 45°)L$$

$$f = .3973F$$

$$F + f = (\cos 70°)(\cos 45°)L + .3973(\cos 70°)(\cos 45°)L$$

$$F + f = .3378L$$

$$TAN\ 70° = \frac{D^R}{F}$$

$$TAN\ \omega = \frac{D^R}{F+f}$$

$$TAN\ \omega = \frac{TAN\ 70°\ F}{.3378L}$$

$$TAN\ \omega = \frac{(TAN\ 70°)(COS\ 70°)L(COS\ 45°)L}{.3378L}$$

$$TAN\ \omega = 1.9670 \quad \omega = 63.052° = 90° - 63.052° = 26.947°$$

Figure 12J:
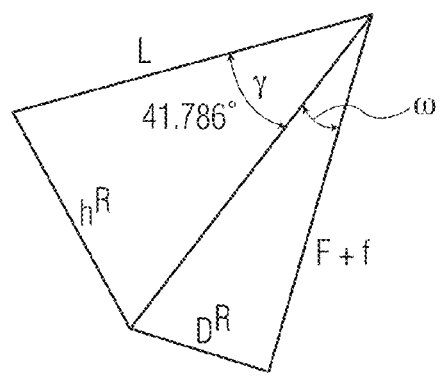

Step 4: Find cup impactor inclination angle as shown in FIG. 12J.

$$TAN\ 63.118° = \frac{h^R}{(F+f)}$$

From Before: $F + f = .3378L$ $$SIN\ \gamma = \frac{h^R}{L}$$

-continued $$\text{SIN } \gamma = \frac{(\text{TAN } 63.118°)(.3378)L}{L}$$

$$\text{SIN } \gamma = .6663$$

$$\gamma = 41.786°$$

Figure 12K:
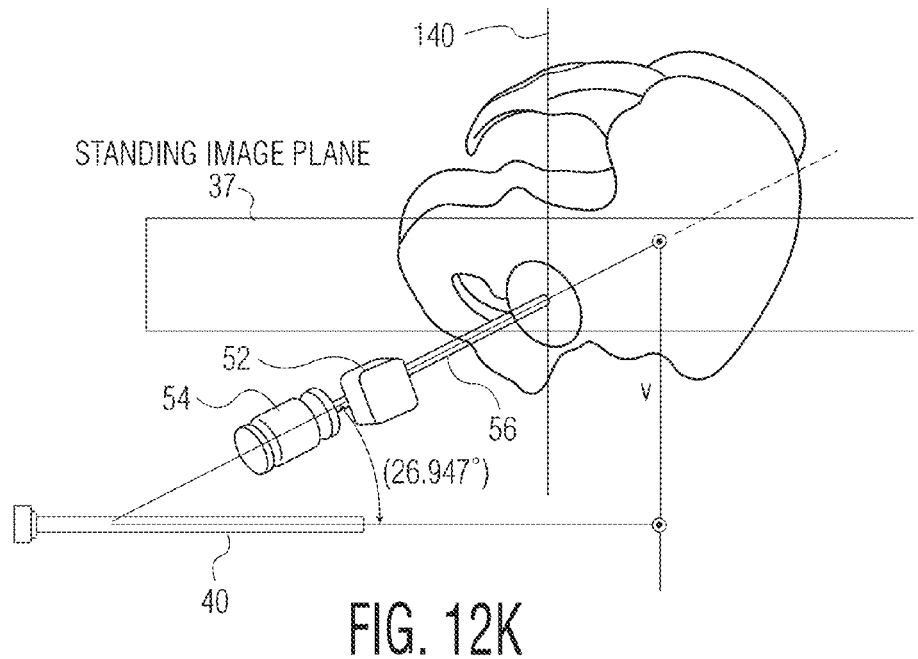
Figure 12L:
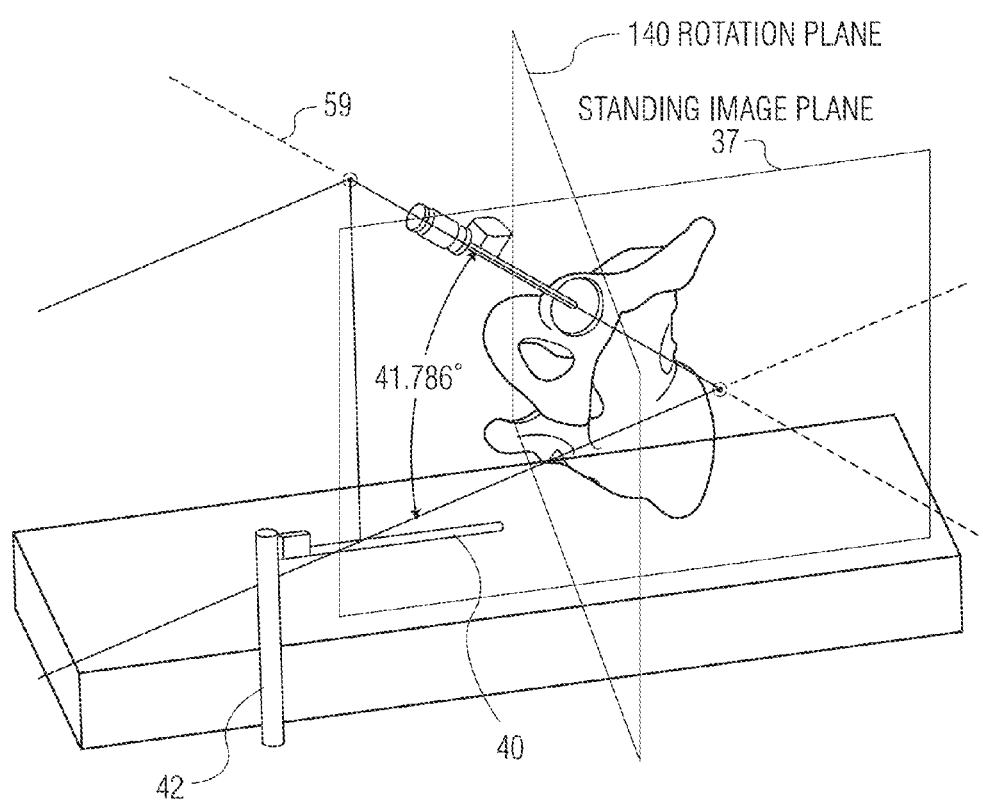

The following angular values are used for the navigation system to effectively impact a cup at a desired standing position of 45°/20° (inclination/anteversion) and are shown in FIGS. 12K and 12L. FIG. 12L shows standing plane 37 and rotated plane 140.
Navigation version angle=26.947 deg
Navigation inclination angle=41.786 deg

EXAMPLE 5

Figure 13B:
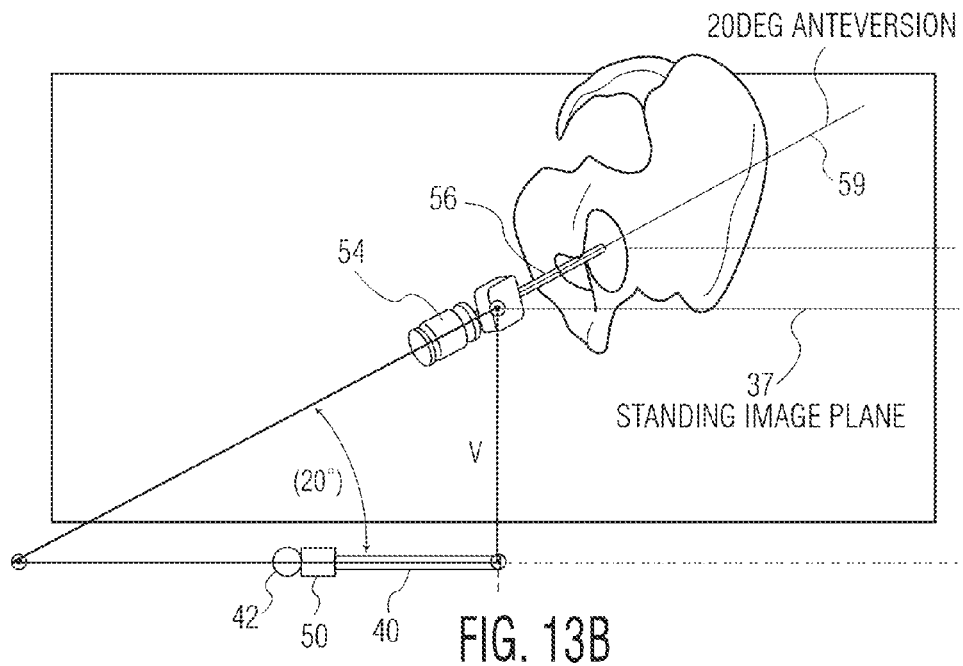
FIGS. 13 through 13G shows the repositioning of an acetabular cup impactor or reamer from a pre-operative plan based on a standing x-ray with 45° inclination and 20° anteversion desired based on the standing x-ray with the pelvis being rotated in 10° of obliquity as set forth in example 5 of the present application.
Figure 13C:
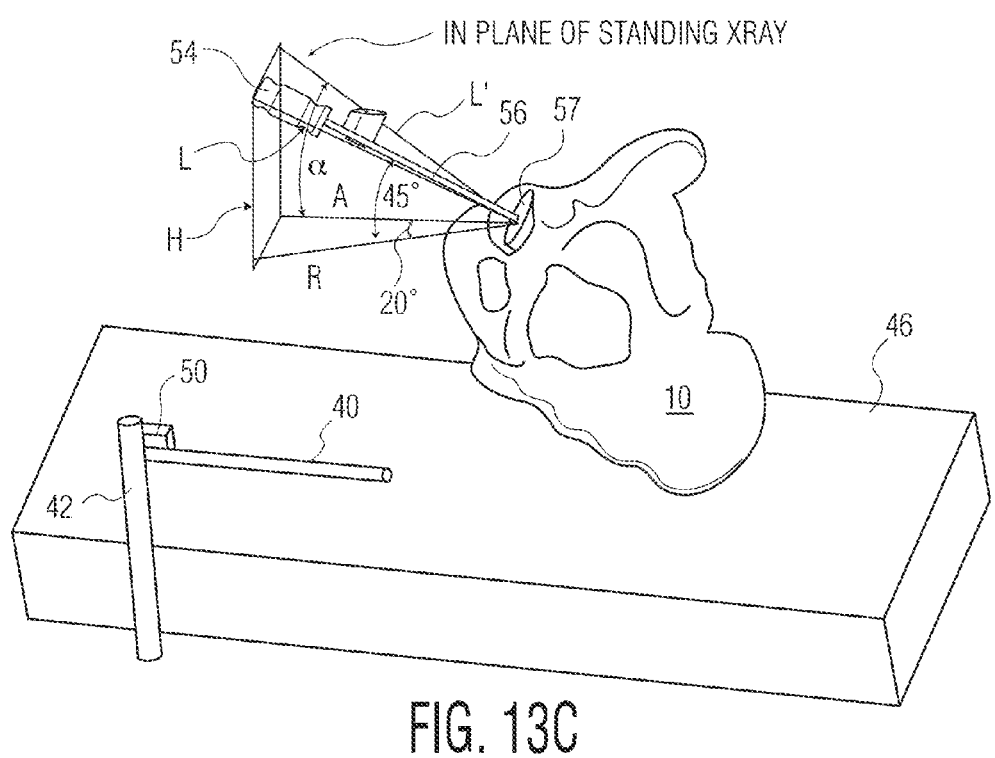

Here the cup impactor orientation is 45° INCLINATION, 20° ANTEVERSION, AND THE PELVIC ORIENTATION IS 0° TILT, 0° ROTATION, and 10° OBLIQUITY (to be confirmed below). FIGS. 13 and 13A show a top view and front view of what a pelvis at 10 deg of Obliquity looks like. To find obliquity changes, two points are identified on the intra-op pelvis (refer to FIG. 9) to determine the angle of obliquity. The pelvis obliquity has changed by 10 degrees from the perfect position of 90 degrees.
Calculations for finding the impactor angles to be used by Navigation
Step 1: As shown in FIG. 13B, project pre angle change impactor inclination angle onto plane of angle change. In this case it is the Standing Image Plane 37 shown in FIG. 13. Calculation angles are shown in plane of standing x-ray in FIG. 13C.
Referring to FIG. 13C, project onto plane 37 (standing x-ray) that the change in angle will take place.

$$\cos 45° = \frac{R}{L} \quad R = \cos 45° \, L$$

$$\cos 20° = \frac{A}{R} \quad A = (\cos 20°)(\cos 45°)L$$

$$\sin 45° = \frac{H}{L} \quad H = \sin 45° \, L$$

$$\tan \gamma = \frac{H}{A} = \frac{\sin 45°}{(\cos 20°)(\cos 45° \, L)}$$

$$\gamma = 46.7808°$$

Figure 13D:
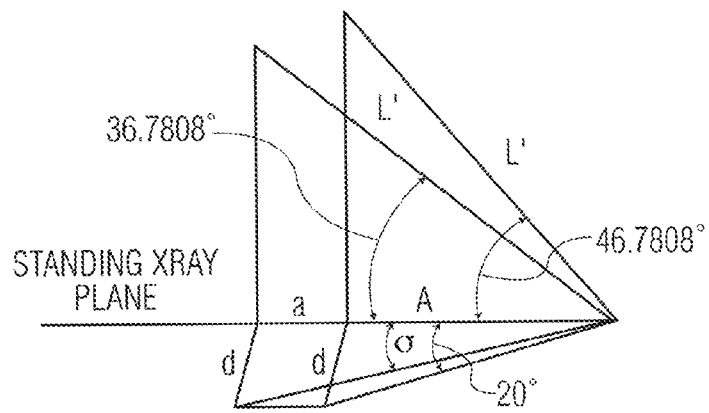

Step 2: Rotate 10 deg of Obliquity in plane of rotation (Standing Image Plane).
Step 3: Calculate impactor version angle as shown in FIG. 13D.

$$\cos 46.7808° = \frac{A}{L^1} \quad L^1 = \frac{A}{\cos 46.7808°}$$

$$\cos 36.7808° = \frac{(A+a)}{L^1} \quad L^1 = \frac{(A+a)}{\cos 36.7808°}$$

$$\frac{A}{.6848} = \frac{A}{.8009} + \frac{a}{.8009}$$

$$A = .8550A + .8550a$$

$$.1450A = .8550a$$

$$a = .1695A$$

From Before:

$$a = (\cos 20°)(\cos 45°)L$$

$$a = 0.1126L$$

$$\text{so: } A = 0.6644L$$

$$A + a = 0.7771L$$

Solve for σ

$$\tan \sigma = \frac{d}{.7771L}$$

$$\tan 20° = \frac{d}{.6644L}$$

$$d = .2418L$$

$$\tan \sigma = \frac{.2418L}{.7771L} \quad \sigma = 17.283°$$

Figure 13E:
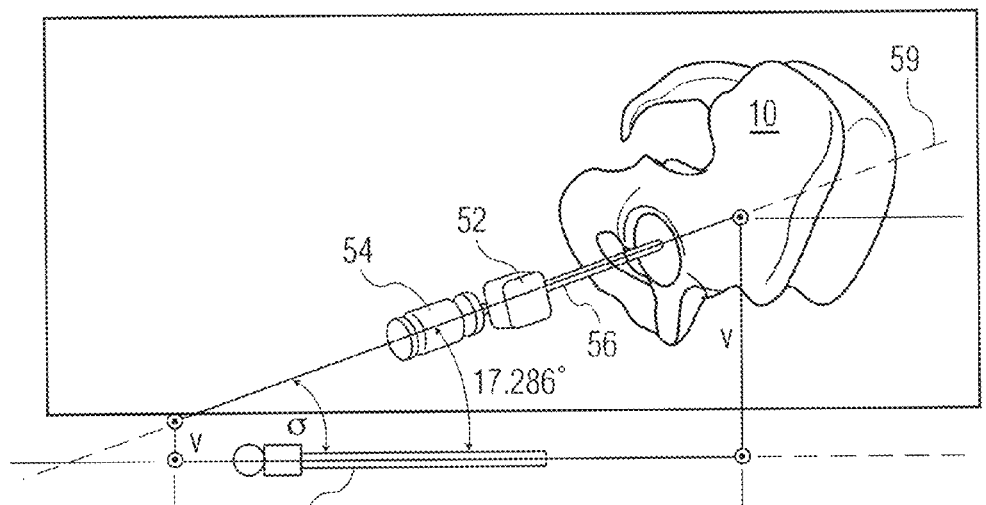
Figure 13F:
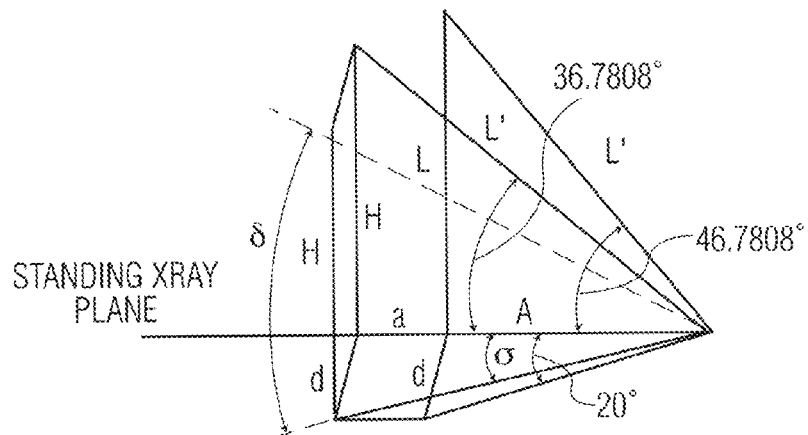
Figure 13G:
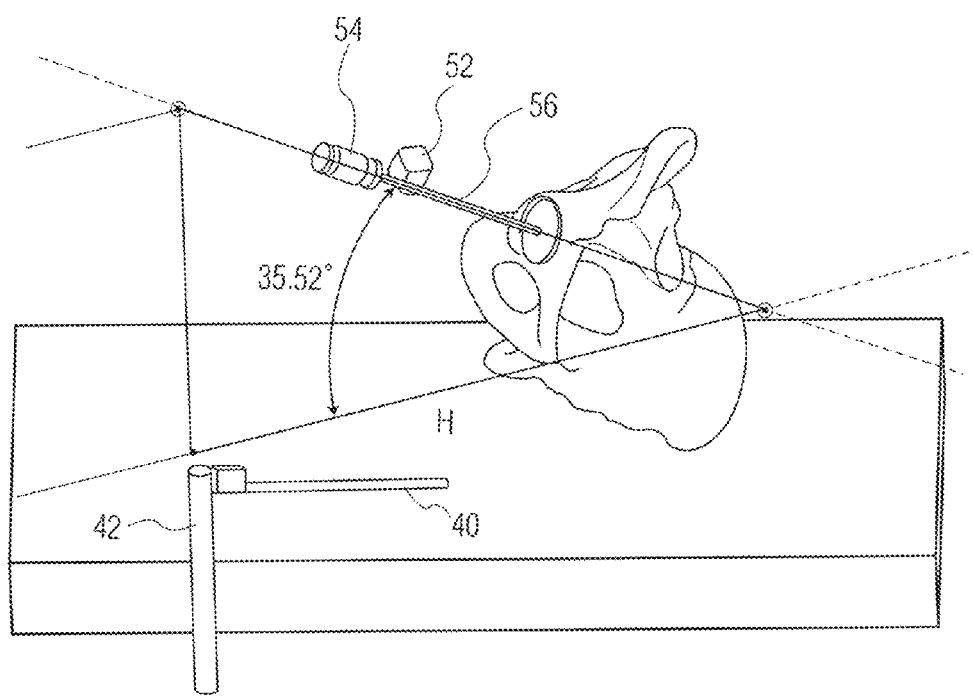

The new position of the impactor handle is 17.286 degrees off the reference. This is one of the input angles needed for navigation and is shown in FIG. 13E.
Now calculate the inclination angle of the impactor as shown in FIG. 13F.

$$\tan 36.7808° = \frac{H}{(A+a)}$$

From Before: $(A + A) = .7771L$ $$\sin \delta = \frac{H}{L}$$

$$\sin \delta = \frac{(\tan 36.7808°).7771 \, L}{L}$$

$$\delta = 35.5166° \text{ shown in FIG. } 13G$$

The following angular values are used for the navigation system to effectively impact a cup at 45/20. Navigation version angle=17.283 deg; Navigation inclination angle=35.520 deg.

EXAMPLE 6

Figure 14:
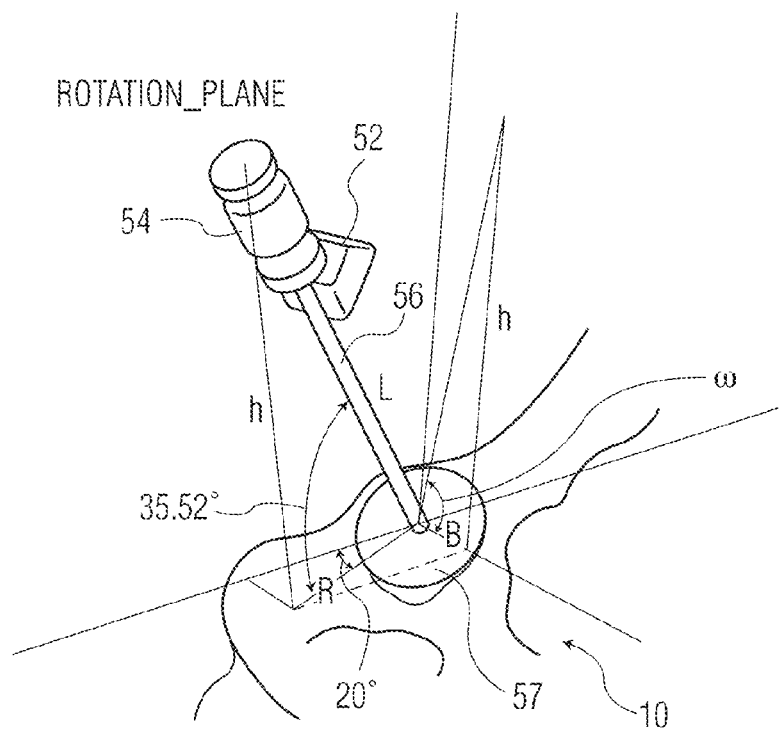
FIGS. 14 through 14E shows the repositioning of an acetabular cup impactor/reamer where the desired orientation is 45° inclination and 20° anteversion based on a standing x-ray with 10° of obliquity imparted to the pelvis when being placed on an operating table as set forth in example 6 of the present application.

Here the cup impactor orientation is 45 DEG INCLINATION, 20° ANTEVERSION, AND THE PELVIC ORIENTATION IS 0° TILT, 8° ROTATION (to be confirmed below) and 10° OBLIQUITY (to be confirmed below). Calculations for determining amount of Obliquity and Rotation: Use the method in Example 4 to calculate the amount of Rotation, and use the method in Example 5 to calculate the amount of Obliquity. Calculations for finding the impactor angles to be used by Navigation:
Step 1:
Use the method in Example 5 to find the following angles for the cup impactor for 10 deg Obliquity:
Cup impactor version=17.283 deg
Cup impactor inclination=35.516 deg
Step 2:
Now project these onto the plane for rotation, rotate 8 deg, and project back to plane that impactor is on (See FIG. 14).
FIG. 14 shows the cup impactor position prior to rotating 8 degrees $$\text{COS } 35.516 = \frac{A}{L} \quad A = (\text{COS } 35.516)L$$

$$\text{SIN } 35.516 = \frac{h}{L} \quad h = (\text{SIN } 35.516)L$$

$$\text{COS}(90° - 17.283°) = \frac{B}{A}$$

$$(\text{COS } 72.717)(\text{COS } 35.516)L = B$$

$$.2418\ L = B$$

$$\text{TAN } \omega = \frac{h}{B} = \frac{(\text{SIN } 35.516)L}{(\text{COS } 72.717)(\text{COS } 35.516)L}$$

$$\omega = 67.400°$$

Figure 14A:
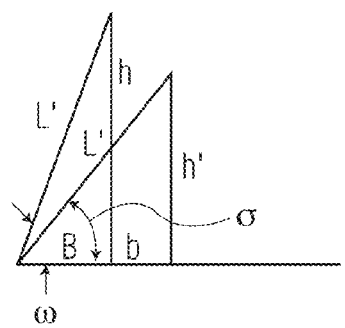

Now rotate 8 degrees as shown in FIG. 14A

$$\sigma = \omega - 8°$$

$$\sigma = 67.400 - 8°$$

$$\sigma = 59.400°$$

Figure 14B:
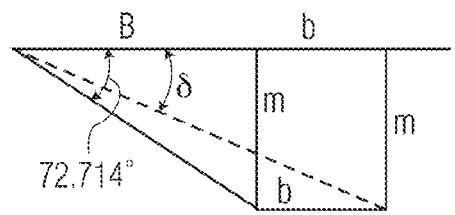
Figure 14C:
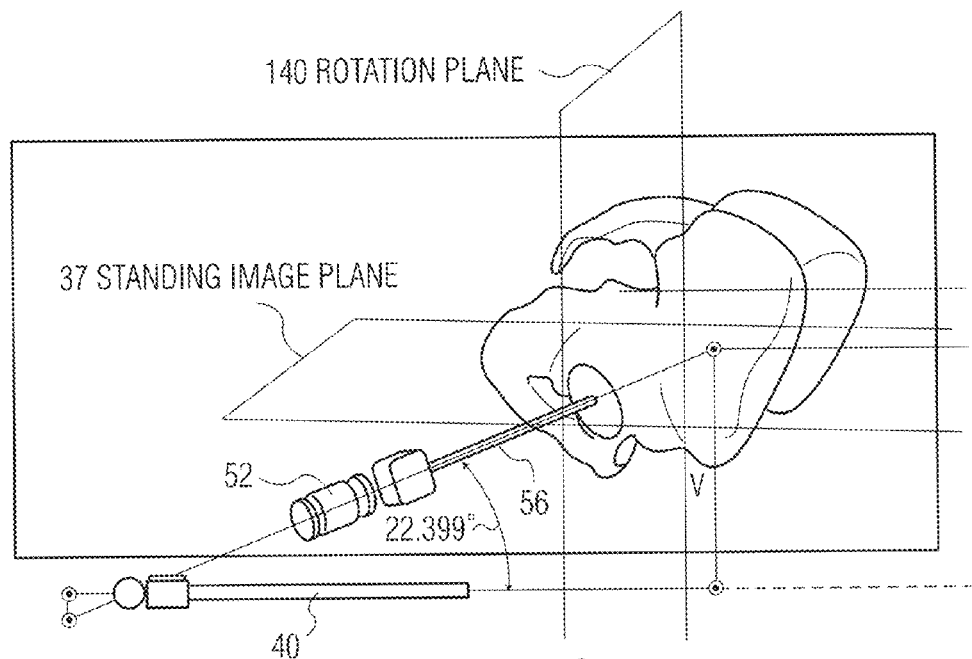

Now project back to plane of impactor as shown in FIGS. 14A, 14B and 14C.

$$\text{TAN } 72.717 = \frac{m}{B}$$

$$\text{TAN } \delta = \frac{m}{(B + b)}$$

$$\text{TAN } (72.717)B = \text{TAN } \delta(B + b)$$

$$\text{COS } 67.400 = \frac{B}{L^1} \quad L^1 = \frac{B}{\text{COS } 67.400}$$

$$\text{COS } 59.400 = \frac{B + b}{L^1} \quad L^1 = \frac{(B + b)}{\text{COS } 59.400}$$

$$\frac{B}{\text{COS } 67.400} = \frac{(B + b)}{\text{COS } 59.400}$$

$$\frac{B}{.3843} = \frac{B}{.5090} + \frac{b}{.5090}$$

$$B = .7549A + .7549b$$

$$.2451BA = .7549b$$

$$b = .3246B$$

$$\text{TAN } \delta = \frac{m}{(B + b)}$$

$$\text{TAN } 72.717 = \frac{m}{B}$$

$$\text{TAN}(72.717)B = \text{TAN } \delta(B + b)$$

$$\text{TAN}(72.717)B = \text{TAN } \delta(B + .3246\ B)$$

$$3.2139\ B = \text{TAN } \delta(1.3246\ B)$$

$$2.4263 = \text{TAN } \delta$$

$$\delta = 67.601°$$

Navigated impactor version $90° - 64.601° = 22.399°$

Figure 14D:
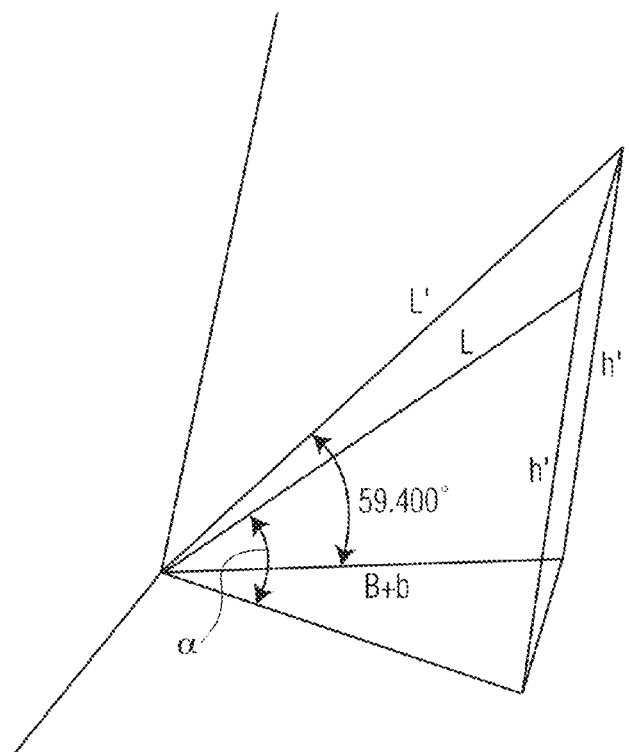

Find impactor inclination (shown in FIG. 14D).

$$\text{TAN } 59.400 = \frac{h^1}{(B + b)}$$

$$\text{SIN } \alpha = \frac{\text{TAN } 59.400(B + b)}{L}$$

-continued

From Before: $.2418\ L = B$ and $b = .3246B$ $$b = .3216(.2418)L$$

$$b = .0785\ L$$

$$B + b = .2418\ L + .0785\ L$$

$$= .3203\ L$$

$$\text{SIN } \alpha = \frac{\text{TAN } 59.400(.323)L}{L}$$

$$\alpha = 32.798°$$

The following angular values are used for the navigation system to effectively impact a cup at 45/20.
Navigation version angle=22.399 deg (FIG. 14C)
Navigation inclination angle=32.798 deg (FIG. 14E)

EXAMPLE 7

Here the cup impactor orientation is 45° INCLINATION, 20° ANTEVERSION, AND THE PELVIC ORIENTATION IS 10° TILT (to be confirmed below), 8° ROTATION (to be confirmed below) and 10° OBLIQUITY (to be confirmed below).

Calculations for determining amount of Obliquity and Rotation:
Use the method in Example 3 to calculate the amount of Tilt
Use the method in Example 4 to calculate the amount of Rotation
Use the method in Example 5 to calculate the amount of Obliquity
Calculations for Finding the Impactor Angles to be Used by Navigation:
Step 1:
Use the methods in Example 6 to find the impactor angles to be used for Navigation after applying 8 deg of Rotation and 10 deg of Obliquity.
Cup impactor version=22.399 deg
Cup impactor inclination=32.798 deg
Step 2:
Apply 10 deg of Tilt.

Figure 15:
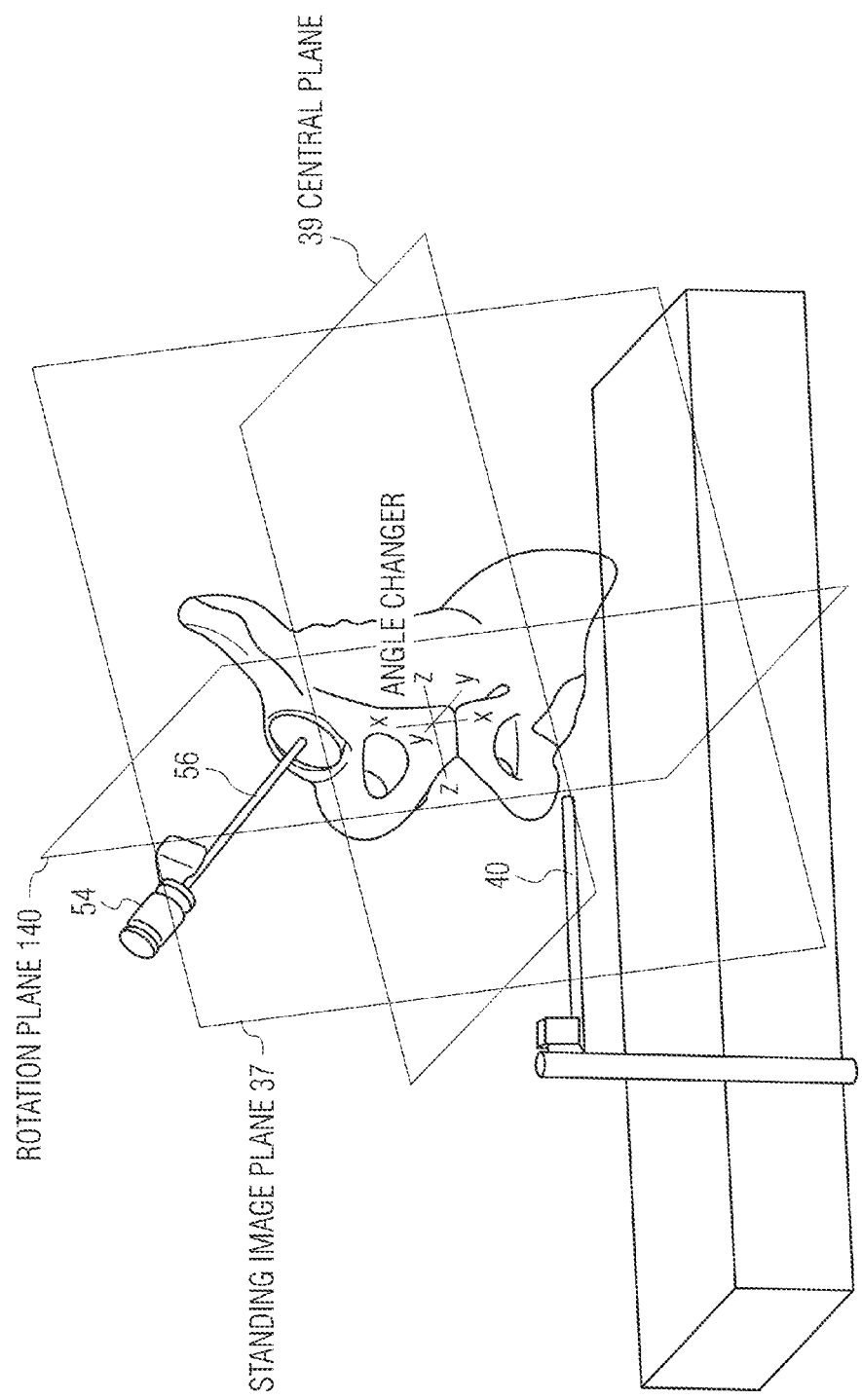
FIGS. 15 through 15D of the present application show the repositioning of an acetabular cup impactor from a desired 45° inclination and 20° anteversion based on a standing x-ray to a pelvis oriented on an operating table with 10° tilt, 8° rotation and 10° obliquity change from the standing x-ray as set forth in example 7, with FIGS. 15 and 15A showing the standing x-ray anterior/posterior plane, the central plane and a rotational plane of the pelvis along with the x, y and z vectors laying on each of the planes.

FIG. 15 shows the three basic x, y and z directions that angle changes can take place: Tilt, Obliquity, and Rotation. The three directions are along the three basic vector directions of a coordinate system. In Example 6, Rotation and Obliquity were applied 90 degrees to each other. Following this approach, Tilt would be rotated around the third vector Y (perpendicular to the page) of the coordinate system. In FIG. 15, Tilt changes would take place in the Central Plane 39 by rotating on the axis perpendicular (normal) to the Central Plane. The practical issue with this is that the pelvis would be lifting off the OR table in doing this. FIG. 15A illustrates the extreme example of the pelvis with the same Rotation and Obliquity as FIG. 15, but with 180 deg of Tilt applied.

The pelvis is no longer laying on the operating room table with the legs resting along the plane of the table. In this position, the portion of the legs near the pelvis would be lifted off the table. This is not a realistic situation as the patient, no matter what the pelvic tilt, is laying flat on the table. Although this example is extreme, it demonstrates that any pelvic tilt angle applied to the coordinate system would lift the legs up off the table. Calculations could be performed to project the cup inclination and version angles found in Example 6 along the Central Plane 39, rotate the Tilt amount in this plane, and reproject as per the above examples. However, a more practical method would be to perform the calculations as per Example 6, and simply rotate these results by the Tilt angle amount found as per Example 3.

Method to apply 10 deg of Tilt:

Step 1:

Find the amount of Tilt as per Example 3.

Step 2:

Perform calculations as per Example 6 for Rotation and Obliquity. Navigation angles found in Example 6 are shown in FIGS. 15B and 15C.

To apply 10 degrees of positive Tilt, simply subtract 10 degrees from 22.402 deg to yield 12.402 degrees. The cup impactor inclination angle of 32.798 deg remains the same.

This example uses the apparent obliquity change when looking across the reference from the front of the OR table. In reality, the pelvis has obliquely changed in the direction of the pelvic tilt. In this example, the obliquity would be 10 degrees off the front of table plane. The calculations below show what the actual obliquity would be (see FIG. 15D).

$$TAN\ 10° = \frac{d}{h}$$

$$COS\ 10° = \frac{d}{L}$$

$$TAN\delta = \frac{L}{h}$$

$$TAN\ \delta = \frac{TAN\ 10°}{COS\ 10°}$$

$$\delta = 10.15°$$

Figure 15D:
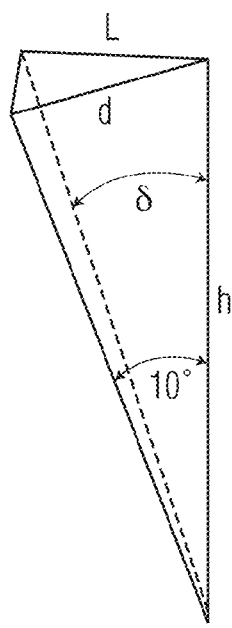

The plane defined by the front of the table would be a plane thru d and h of FIG. 15D. The plane defined by the tilt plane in the direction of the standing x-ray image plane would be defined by L and h. The actual obliquity would be 10.15 degrees not 10 degrees. However, the difference of 0.15 degrees is inconsequential in practice for cup positioning in hip surgery and that using 10 degrees for the calculations would be acceptable. Either method could be used.

Figure 16:
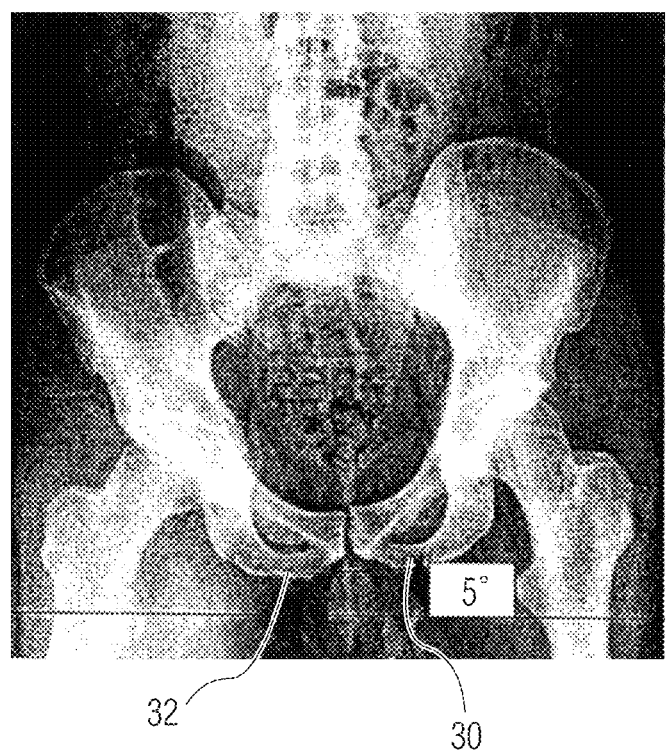
FIG. 16 shows a preoperative image showing an individual with one leg shorter than the other (non-zero pelvic tilt in the x-ray)
Figure 20:
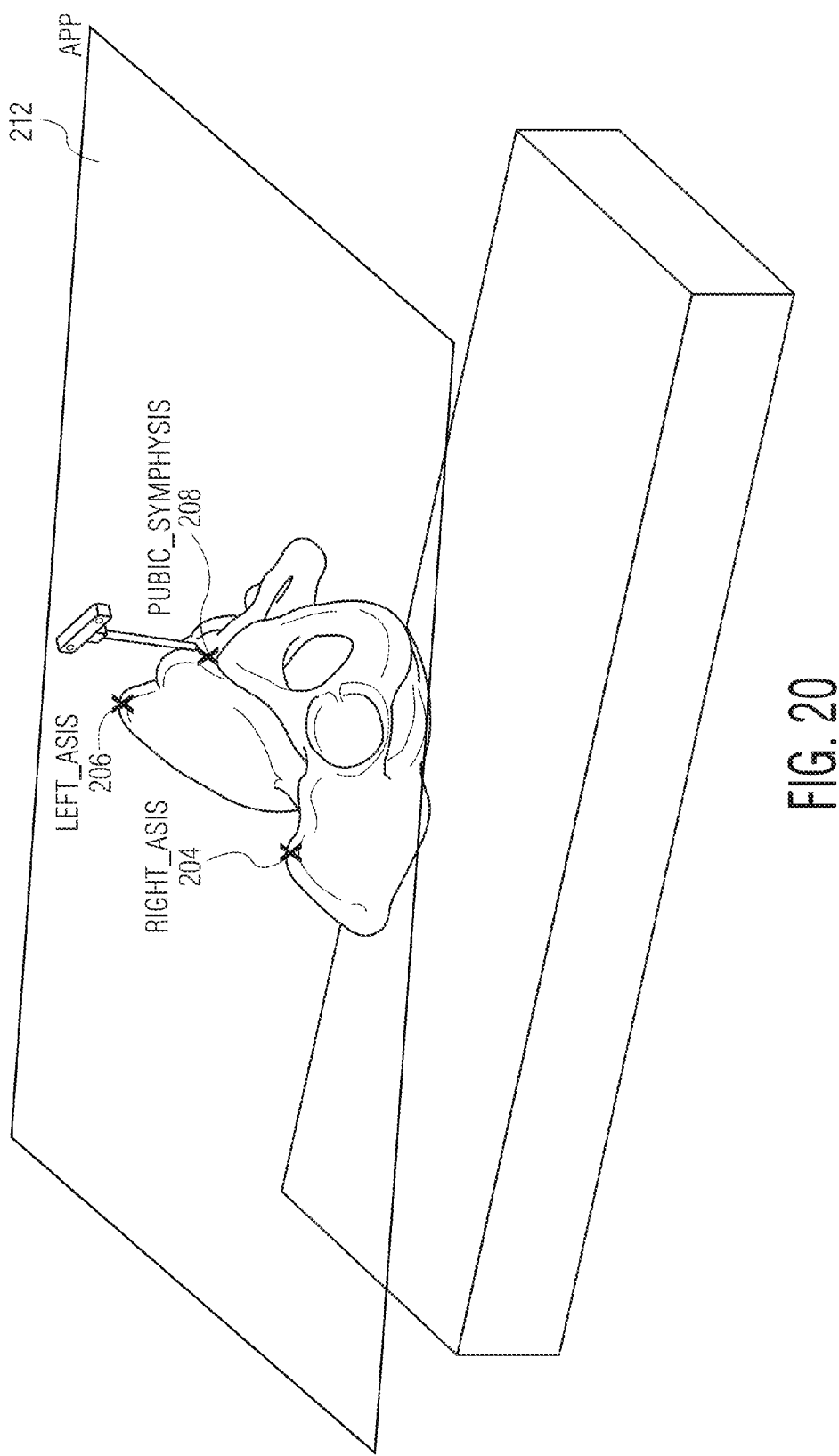
FIG. 20 schematically shows an image of a pelvis located in the supine position on an operating table with three points defining the anterior pelvic plane, the three points being the left anterior superior iliac spine, the right anterior superior iliac spine and the pubic symphysis.
Figure 21:
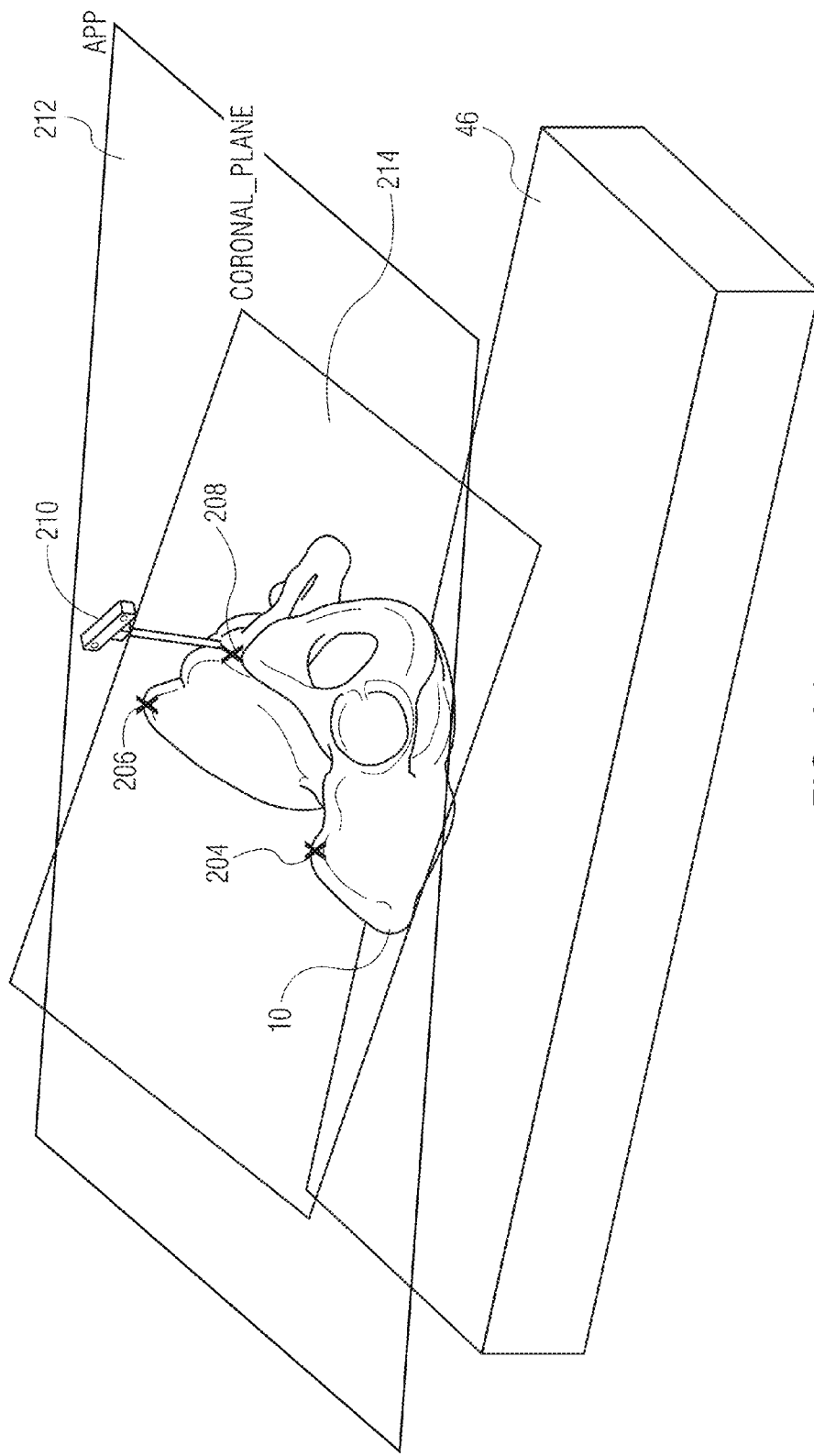
FIG. 21 is a schematic view showing the pelvis located on an operating table in a supine position showing in the navigation system tracker, the coronal plane and the anterior pelvic plane.

The pre-operative image may show a leg shortening that needs correction as shown in FIG. 16. Note that the pelvis is in the pre-operative x-ray shown in FIG. 16 is not parallel to the floor (the line joining points 30 and 32 is not parallel). A line through points 30 and 32 is angled at 5° from horizontal. The surgeon may want to correct for this. If a check for obliquity is taken in this image, it would show that the pelvis is 5 degrees off. The method of measurements set forth above allows for correcting this. To correct for the 5 degrees, a measurement for obliquity as shown in FIG. 20 would be taken. But suppose the surgeon wants to keep the 5 degrees of obliquity, then the extra 5 degrees is added/subtracted from the intra-operative obliquity measurement and used to calculate the impactor inclination angle.

It is assumed that the intra-operative image is taken perpendicular (normal) to reference bar 40. Normally, this is a good assumption, but in practice, it may be a few degrees off from being perpendicular. This could be accounted for in two ways:

The two or more radiopaque points in the reference bar could be at precise distance apart from each other. Any angular differences in the image would result in a difference in measurement between the points which can be calculated in the computer.

The preferred reference bar is radiolucent, and has two radiopague spheres (44, 45) embedded in reference bar 40 3 inches apart. Any angular differences in the image would result in a difference in measurement between spheres 44 and 45. An image that is taken perpendicular to bar 40 would show a 3 inch measurement between the radiopaque spheres. However, an image at a 10 degree angle to the bar would show a distance of 2.954 inches long. So in practice, an image would be taken and the actual distance on the image compared against the known distance of 3 inches. It would be discovered that the image is being taken at an angle to the reference at that time. The x-ray direction could then be changed to account for it, or the calculated 10 degree angle could be used as a modifier to the follow-up dimensions to be used for obliquity, tilt, and rotation.

If for some reason it is suspected that the x-ray emitter is also taken at an angle to the floor, as in pointing more to the floor or away, another option would be to include a third radiopaque marker in the reference bar that could be used for angular corrections.

Using the above methodology to determine the pelvis location intra-operatively can have benefits beyond cup placement. Another use would be for drilling along a certain direction in times where it is desirable to place a screw in the area having the most bone. An example of this would be in a severe revision situation whereas bone erosion can comprise desirable areas to have fixation.

Alternately, a navigation tracker could be placed on the x-ray emitter itself and used to make automatic corrections. If for some reason it is suspected that the x-ray emitter is also taken at an angle to the floor, as in pointing more to the floor or away, another option would be to include a third radiopaque marker in the reference that could be used for angular corrections. The navigation tracker could be used for this as well.

This invention describes the benefits of taking a pre-operative standing image vs. a pre-operative supine image. A standing image takes into account the normal pelvic position for each individual patient as opposed to a laying down/supine image which can alter the pelvis position similar to laying down on the operating table.

However, the invention does not exclude supine images, both pre-operative and intra-operative. For example, for the direct anterior surgical approach, the patient is supine on the table. It could be argued that the pelvis may have similar angular changes for the supine pre-operative x-ray image to the intra-operative supine position on the table, and therefore, in a way, recreating a natural standing pelvic position due to the similar angular changes.

At a minimum, the two A/P promontory points and the public symphysis point needs to be taken. If only these three points are taken, the line between the promontory points could help dictate the obliquity angle, and an assumption could be made that the x-ray emitter is parallel to the operating table and floor, and therefore, any line parallel to the floor on the image could be the reference. This also assumes that the image detector is parallel to the operating table and/or floor.

A common operating room table can be adjusted in two ways: trendelenburg (about the long axis of the table) and lateral tilt (about the short axis of the table). It is conceivable that the table could be adjusted to account for pelvic obliquity and rotation prior to an intro-operative image to account for any angular changes. This would be an attempt to adjust the table in order to place the pelvis at the "perfect" position 90° to the floor as described above, and therefore a surgeon could simply use the impactor at the 45°/20° position to the floor. There are two major issues with this that this invention addresses. First, there are only two adjustments with the table, not three. There is not an adjustment for tilt and therefore the surgeon would need to somehow adjust for this. Second, multiple intra-operative images would have to be taken in order to get the exact position needed for the pelvis. For instance, the table would have to be tilted to remove any intra-operative pelvic rotation. An image would be taken, and a guess as to how much the table would be adjusted to remove rotation. Another image taken, and further adjustment until the pubic symphysis is directly positioned over the sacrum. This would be a visual positioning, as well as adjusting for obliquity with trendelenburg table adjustments.

Figure 17:
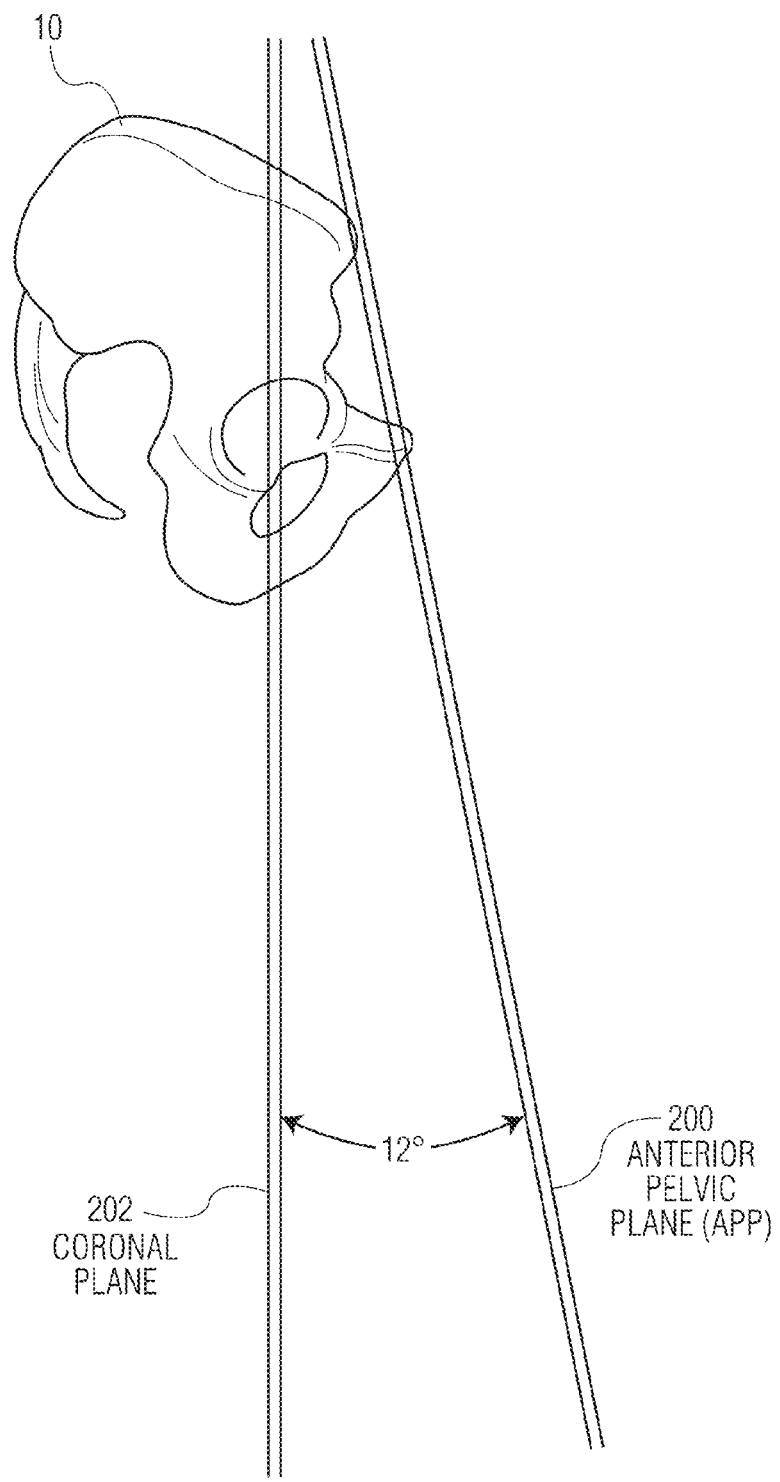
FIG. 17 is a preoperative standing lateral x-ray image showing the coronal plane and the anterior pelvic plane.
Figure 18:
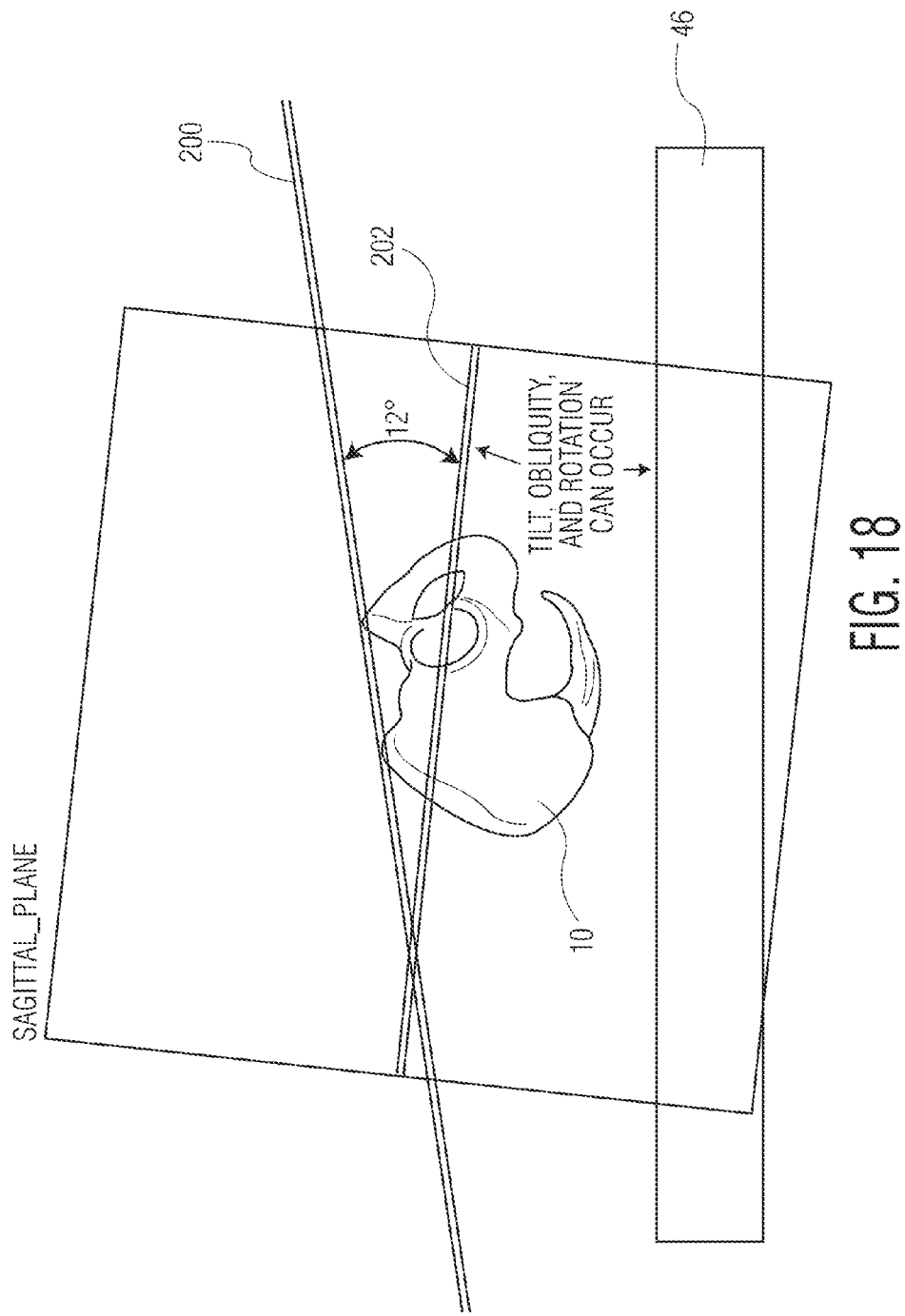
FIG. 18 is a schematic view showing an operating table with a pelvis positioned thereon in a supine position including the coronal plane, anterior pelvic plane, and sagittal plane.
Figure 19:
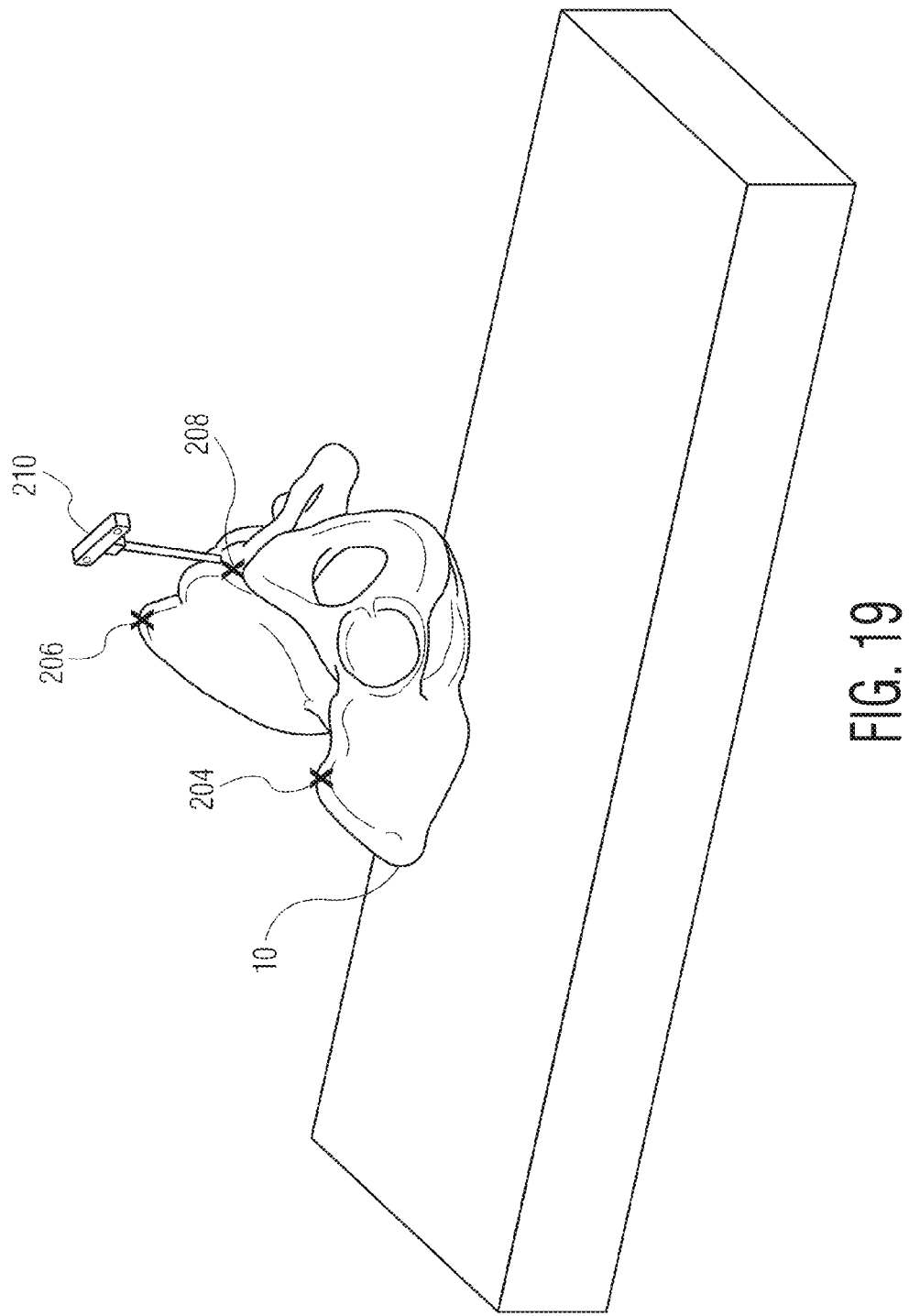
FIG. 19 shows a navigation system tracker mounted on the pelvis of the patient while laying on the operating table in the supine position.

An alternative method is shown in FIGS. 17-24. This method requires only a single x-ray of the patient and works best when used in an anterior approach for acetabular prosthetic joint replacement. In an anterior approach the patient is supine i.e., laying on his or her back. Referring to FIGS. 17 to 19 there is shown schematically a standing lateral image of pelvis 10 showing an anterior pelvic plane 200, which plane is defined by three points; namely, the pubic synthesis 208, the right anterior superior iliac spine 204, and the left anterior superior iliac spine 206, which can be seen on the schematic of FIG. 19. In FIG. 17a coronal plane 202 is located perpendicular to the floor on which the patient is standing and the natural pelvic tilt angle (here shown as 12°) between the coronal plane and the anterior pelvic plane (APP) can be easily measured or calculated. Natural pelvic tilt (the angle between the APP and coronal plane can vary from 20° to 20°. Typically the x-ray of pelvis 10 is a digital x-ray allowing software to calculate any required planes or distances.

When performing the operation, the patient with pelvis 10 is placed in a supine i.e. laying on the patients back on the operating table 46. Note that pelvis 10 can exhibit some tilt, obliquity in rotation after being placed on the table 46. As shown in FIG. 19, the right anterior superior iliac spine 204, the left anterior superior iliac spine 206, and the pubic synthesis 208 shown on pelvis 10 can be accessed in the supine.

A tracker 210 may be brought into contact with each of the points 204, 206, and 208 to locate them in the operating room orientation tracking system. Such a system may be a typical optical tracking system located in the operating theatre. After locating points 204, 206 and 208, the tracker 210 then may be fixedly mounted on the pelvis to track any changes in position which may occur during the implantation of an acetabular cup. As indicated above, the three points 204, 206, and 208 are used to determine the anterior pelvic plane. Since the pelvic tilt angled between the anterior pelvic plane 212 and the coronal plane 214 is known from the standing x-ray, the orientations of the two planes can be reproduced.

Figure 22:
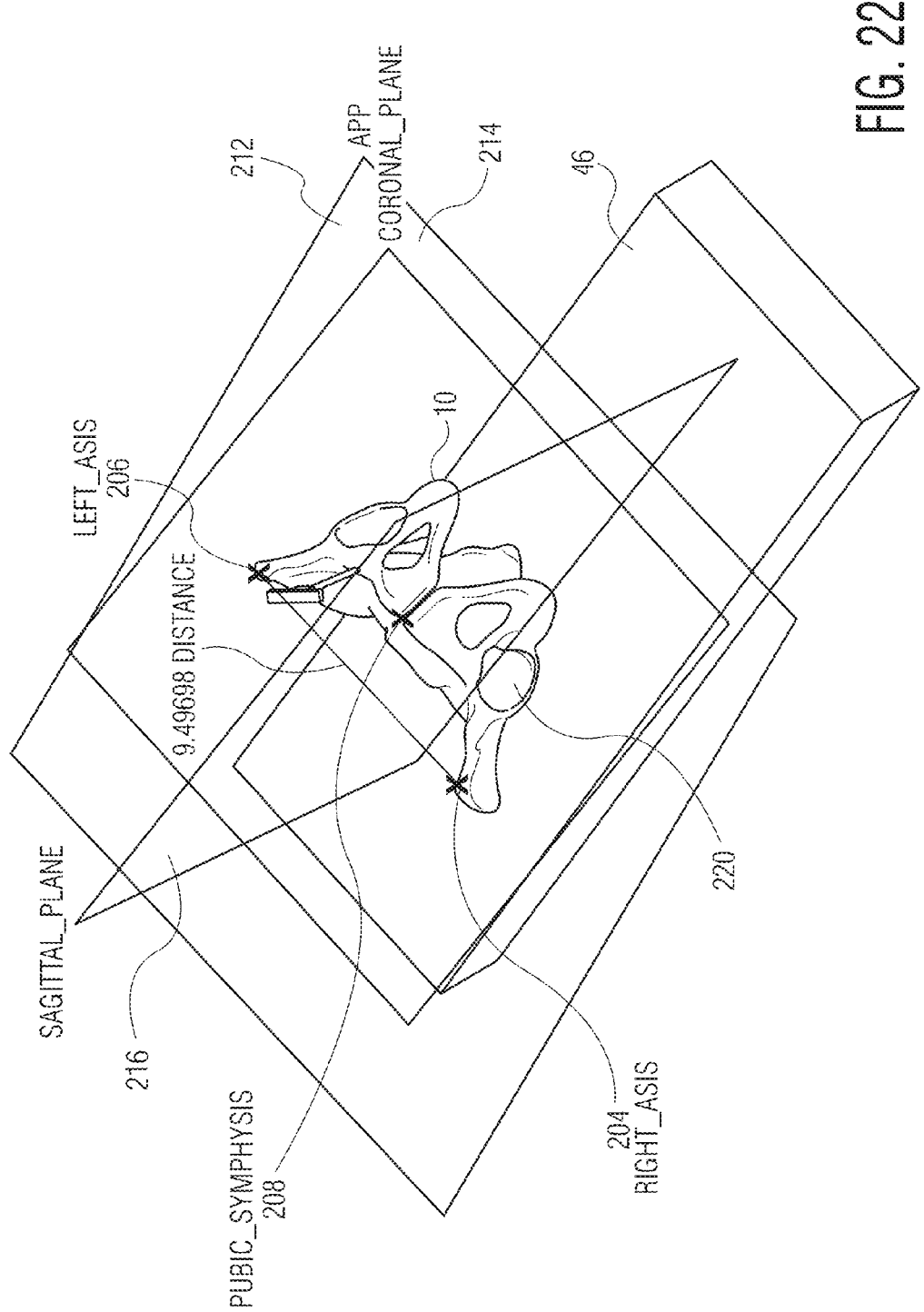
FIG. 22 is a schematic view similar to FIG. 21 also showing a sagittal plane extending perpendicularly to the coronal plane through the midpoint between the anterior superior iliac spines.
Figure 23:
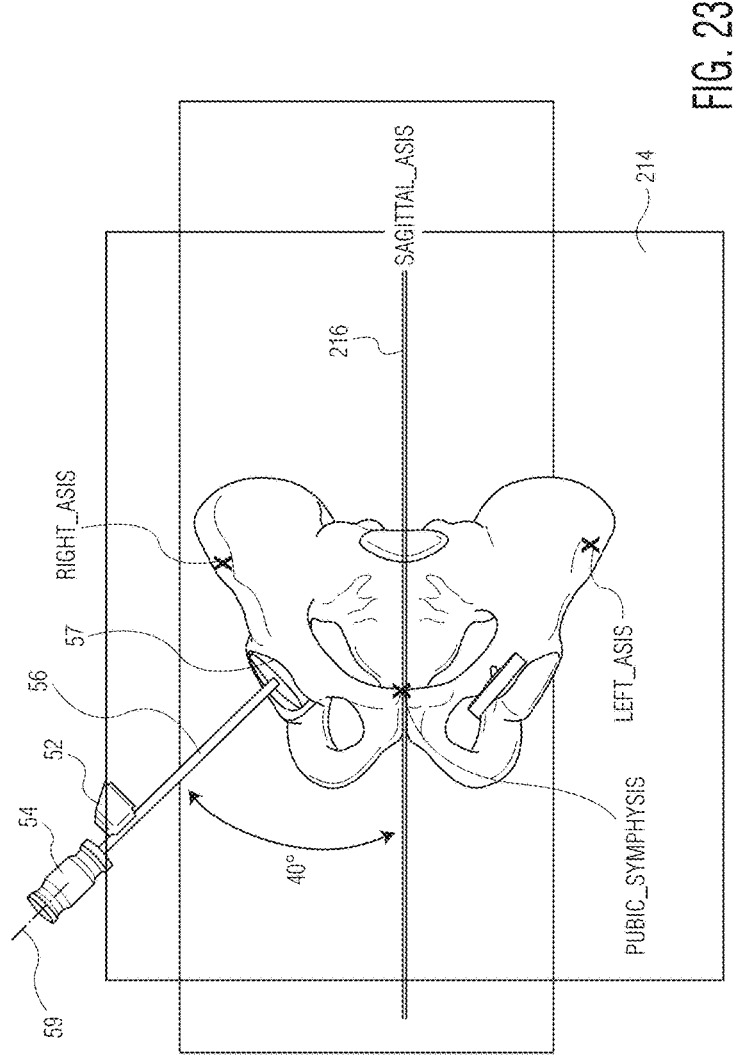
FIG. 23 is a schematic top view of an operating table with the pelvis positioned in the supine position showing an acetabular alignment instrument located at an abduction angle in the coronal plane.

Referring to FIG. 22, a sagittal plane 216 is drawn through the midpoint between the right and the left anterior superior iliac spines 204, 206 with the sagittal plane 216 being perpendicular to coronal plane 214. Since at this point in the method the locations of the sagittal plane 216 and the coronal plane 214 are known, a predetermined abduction in version (anteversion) angles can be measured with respect to the center of the acetabulum 220. Thus, FIGS. 23 and 24 show an arbitrary example of 40° in abduction in the coronal plane of an acetabular insertion instrument, such as an impactor or a reamer, which is in all respects is similar to that described above with respect to the other embodiments.

Figure 24:
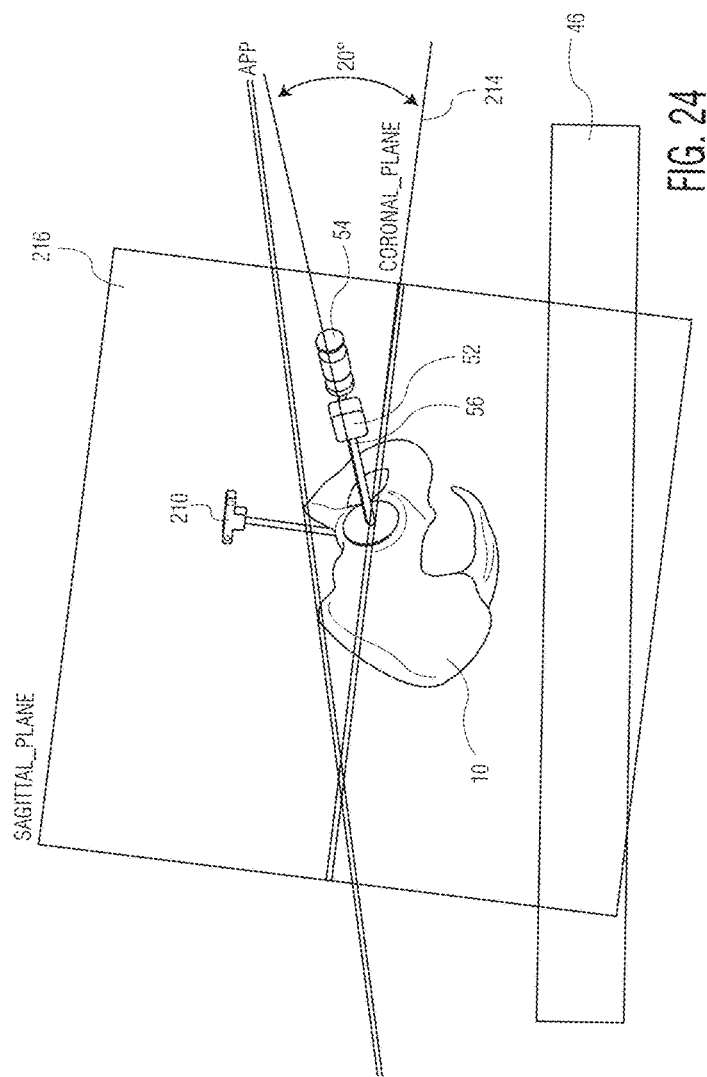
FIG. 24 shows a schematic side view of a pelvis positioned on the operating table in the supine position with a version angle shown for an acetabular cup alignment instrument with 20° of version.

FIG. 24 shows a version angle of 20° from the coronal plane in the sagittal plane with the same instrument.

The advantage of this alternate method for use, preferably in the supine position, is that no interoperative x-rays are required. Thus, only a single, one, individual, digital standing x-ray of a patient need be taken when using the direct anterior or anterolateral approach in replacing an acetabular cup (both approaches are performed with the patient in the supine position, i.e., laying on his or her back on the operating table). While this alternate process is best used with the patient in the supine position, it may also be used with other operative approaches.

FIG. 25 shows a typical operating room navigation or orientation system generally denoted as 300. The relative position of the patient's bones, such as the patient's femur 99 and the patient's pelvis 10', can be determined and tracked by attaching reference bodies or trackers 301, 310, which include reflective markers 302, 312. Reference bodies or trackers 301, 310 can be attached to bones or tools by using pins or screws (304, 314) or various quick release mechanisms. In the embodiment of FIGS. 17-24 only tracker 310 is attached to the pelvis. Tracker 301 is not required. Tracker 301 can be used to locate points 204, 206 and 208 as discussed above with tracker 310 attached to pelvis 10'. The tracked objects and their relative positions can be displayed on a screen 332 that is connected to the computer system 305. In an embodiment, the display 332 is a touch screen which can also be used for data entry. The position measurement and alignment system 306 includes a positioner 50 used to align the acetabular cup insertion positioning instrument or an acetabular reamer. The positioner 50 has the reference body or position tracker 52 thereon and an acetabular reamer or cup holder 308. The user interface screen or monitor 332 is used to display the position of the acetabular cup holder or reamer 50 with regard to stored patient digital x-ray and other data. The reference body 52 is tracked in space by a camera system 349 which includes light-emitting spheres 350. Thus positioner 50 can be tracked during the surgery in a known manner to set the desired angles with respect to pelvis 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for aligning an acetabular cup insertion instrument using an operating room digital x-ray system and an operating room navigation or orientation tracking system, the method comprising:

taking a single lateral pre-operative x-ray digital image and an anterior-posterior pre-operative x-ray digital image of a standing patient's pelvis;

determining on the pre-operative digital x-ray images a natural pelvic tilt angle by defining an anterior pelvic plane (APP) and determining an angle between the APP and a coronal plane perpendicular to a surface on which the patient is standing;

wherein the APP is defined on the anterior-posterior pre-operative digital x-ray image by first, second and third points on the pelvis; the first, second and third points are a pubic symphysis, a left anterior superior iliac spine and a right anterior superior iliac spine;

calculating lengths and angles between each of the APP points in the anterior-posterior pre-operative digital x-ray, and calculating the angle between the APP and the coronal plane, and a distance between the point of the pubic symphysis and a promontory point in the lateral pre-operative digital x-ray image;

placing the patient on a surface of an operating room table in a supine position;

wherein the operating room table has a tracking element or navigation tracking system;

placing a position tracking device on the patient's pelvis to intra-operatively track movement of the pelvis during surgery; wherein the position tracking device is used to intra-operatively locate the first, second and third points defining the pubic symphysis, and the left and right anterior superior iliac spines when the patient is in a supine position on the operating room table;

thereafter using the operating room navigation or the orientation tracking system to intra-operatively relocate the points defining the APP in an anterior-posterior intra-operatively digital x-ray image and a distance between the point of the pubic symphysis and a promontory point in an lateral intra-operative digital x-ray image;

thereafter locating the coronal plane by using the determined natural pelvic tilt angle and APP plane in the lateral intra-operative digital x-ray image;

calculating lengths and angles between each of the APP points in the anterior-posterior intra-operative digital x-ray, and calculating the angle between the APP and the coronal plane, and a distance between the point of the pubic symphysis and a promontory point in the lateral intra-operative digital x-ray image;

comparing dimensional differences between the points and angles on the pre-operative standing x-ray images and the intra-operative supine x-ray images to calculate the intra-operative pelvic angular deviation and position changes in orientation relative to the pre-operative pelvic position and to calculate a desired correcting anteversion angle with respect to the coronal plane; and using the operating room navigation or the orientation tracking system to orient the acetabular cup insertion instrument having a position tracking device mounted thereon at the desired correcting predetermined anteversion angle with respect to the coronal plane.

2. The method for aligning an acetabular cup insertion instrument as set forth in claim 1, further comprises defining a sagittal plane through a mid-point between the left and right anterior superior iliac spines and perpendicular to the coronal plane.

3. The method for aligning an acetabular cup insertion instrument as set forth in claim 2, further comprising orienting the cup insertion instrument at a predetermined abduction correcting angle with respect to the sagittal plane.

4. The method as set forth in claim 3, wherein the predetermined desired cup abduction and anteversion angles are about 30 to 50 degrees and 10 to 30 degrees respectively.

5. The method as set forth in claim 1, wherein the orientation of the cup insertion instruments is directed by a computer using digital image analysis software receiving input from the operating room digital x-ray system and the operating room position tracking system.

6. A method for aligning an acetabular cup insertion instrument using an operating room digital x-ray system and an operating room navigation or orientation tracking system, the method comprising:

taking a single lateral pre-operative x-ray digital image and an anterior-posterior pre-operative x-ray digital image of a standing patient's pelvis;

determining on the pre-operative digital x-ray images a natural pelvic tilt angle by defining an anterior pelvic plane (APP) and determining an angle between the APP and a coronal plane perpendicular to a surface on which the patient is standing;

wherein the APP is defined on the anterior-posterior pre-operative digital x-ray image by first, second and third points on the pelvis; the first, second and third points are a pubic symphysis, a left anterior superior iliac spine and a right anterior superior iliac spine;

defining, on the pre-operative digital x-ray images, a sagittal plane through a mid-point between the left and right anterior superior iliac spines and perpendicular to the coronal plane;

calculating lengths and angles between each of the APP points in the anterior-posterior pre-operative digital x-ray, and calculating the angle between the APP and the coronal plane, and a distance between the point of the pubic symphysis and a promontory point in the lateral pre-operative digital x-ray image;

placing the patient on a surface of an operating room table in a supine position;

wherein the operating room table has a tracking element or navigation tracking;

placing a position tracking device on the patient's pelvis to intra-operatively track movement of the pelvis during surgery; wherein the position tracking device is used to intra-operatively locate the first, second and third points defining the pubic symphysis, and the left and right anterior superior iliac spines when the patient is in supine position on the operating room table;

thereafter using the operating room navigation or the orientation tracking system to intra-operatively relocate the points defining the APP in an anterior-posterior intra-operative digital x-ray image and a distance between the point of the pubic symphysis and a promontory point in an lateral intra-operative digital x-ray image;

thereafter locating the coronal plane by using the determined natural pelvic tilt angle and APP plane in the lateral intra-operative digital x-ray image;

calculating lengths and angles between each of the APP points in the anterior-posterior intra-operative digital x-ray, and calculating the angle between the APP and the coronal plane, and a distance between the point of the pubic symphysis and a promontory point in the lateral intra-operative digital x-ray image;

comparing dimensional differences between the points and angles on the pre-operative standing x-ray images and the intra-operative supine x-ray images to calculate the intra-operative pelvic angular deviation and position changes in orientation relative to the pre-operative pelvic position and to calculate a desired correcting anteversion angle with respect to the coronal plane and a desired correcting abduction angle with respect to the sagittal plane; and using the operating room navigation or the orientation tracking system to orient the acetabular cup insertion instrument having a position tracking device mounted thereon at the desired correcting predetermined anteversion angle with respect to the coronal plane, and the desired correcting predetermined abduction angle with respect to the sagittal plane.

7. The method as set forth in claim 6, wherein the predetermined desired cup abduction and anteversion angles are about 30 to 50 degrees and 10 to 30 degrees respectively.

8. The method as set forth in claim 6, wherein the orientation of the cup insertion instruments is directed by a computer using digital image analysis software receiving input from the operating room digital x-ray system and the operating room navigation or the orientation tracking system.

* * * * *